US008629132B2

(12) United States Patent
Lee et al.

(10) Patent No.: US 8,629,132 B2
(45) Date of Patent: Jan. 14, 2014

(54) KINASE INHIBITORS

(75) Inventors: Jaekyoo Lee, North Andover, MA (US);
Ho-Juhn Song, Andover, MA (US);
Jong Sung Koh, Seoul (KR); Hee Kyu Lee, Gunpo Si (KR); Youngsam Kim, Seoul (KR); Hong Woo Kim, Cambridge, MA (US); Sunhwa Chang, Cheonan-si (KR); Sun-Hee Lim, Cheonan-si (KR); Jang-Sik Choi, Cheonan-si (KR); Jung-Ho Kim, Cheonan-si (KR); Se-Won Kim, Cheonan-si (KR)

(73) Assignees: Genosco, Buena Park, CA (US);
Oscotec, Inc., Cheonan (KR)

( * ) Notice: Subject to any disclaimer, the term of this patent is extended or adjusted under 35 U.S.C. 154(b) by 435 days.

(21) Appl. No.: 12/945,629

(22) Filed: Nov. 12, 2010

(65) Prior Publication Data
US 2011/0281841 A1    Nov. 17, 2011

Related U.S. Application Data

(60) Provisional application No. 61/261,100, filed on Nov. 13, 2009.

(51) Int. Cl.
| A61K 31/33 | (2006.01) |
| A61K 31/55 | (2006.01) |
| A61K 31/535 | (2006.01) |
| A61K 31/501 | (2006.01) |
| C07D 413/06 | (2006.01) |
| C07D 403/04 | (2006.01) |
| C07D 243/08 | (2006.01) |

(52) U.S. Cl.
USPC .......... 514/210.21; 514/210.2; 514/218; 514/235.8; 514/236.5; 514/252.19; 514/275; 540/575; 544/122; 544/295

(58) Field of Classification Search
USPC .......... 514/210.21, 252.11, 210.2, 252.19, 514/218, 275, 236.5, 235.8; 540/575; 544/122, 295
See application file for complete search history.

(56) References Cited

U.S. PATENT DOCUMENTS

2007/0020253 A1    1/2007    Williams et al.

FOREIGN PATENT DOCUMENTS

| JP | 39005040 B | * | 4/1964 |
| WO | WO 01/60816 A1 | | 8/2001 |
| WO | WO 2007/042299 A1 | | 4/2007 |
| WO | WO-2007/138277 | | 12/2007 |
| WO | WO-2007/149427 | | 12/2007 |
| WO | WO 2009/032694 A1 | | 3/2009 |

OTHER PUBLICATIONS

Notification of Transmittal of the International Search Report and the Written Opinion of the International Searching Authority, or the Declaration, International Search Report and Written Opinion in International Application No. PCT/US10/56583, 12 pages, mailed Jan. 20, 2011.
Supplemental European Search Report mailed Jun. 11, 2013, in corresponding European Patent Application No. 10830814.9.

* cited by examiner

*Primary Examiner* — James O Wilson
*Assistant Examiner* — Ebenezer O Sackey
(74) *Attorney, Agent, or Firm* — Edwards Wildman Palmer LLP; Kongsik Kim; Mark D. Russett

(57) ABSTRACT

The present invention provides a new group of protein kinase inhibitors, pyrropyrimidine and pyrazolopyrimidine derivatives, and pharmaceutically acceptable salts and prodrugs thereof that are useful for treating cell proliferative disease and disorder such as cancer, autoimmune diseases, infection, cardiovascular disease and neurodegenerative disease and disorder. The present invention provides methods for synthesizing and administering the protein kinase inhibitor compounds. The present invention also provides pharmaceutical formulations comprising at least one of the protein kinase inhibitor compounds together with a pharmaceutically acceptable carrier, diluent or excipient therefor. The invention also provides useful intermediates generated during the syntheses of the pyrropyrimidine and pyrazolopyrimidine derivatives.

10 Claims, No Drawings

KINASE INHIBITORS

RELATED APPLICATION

This application claims the benefit of U.S. Provisional Application No. 61/261,100 filed on Nov. 13, 2009. The entire teachings of the above application are incorporated herein by reference.

BACKGROUND OF THE INVENTION

Protein kinases include a large set of structurally related phosphoryl transferases which catalyze the transfer of the terminal phosphate from ATP to the hydroxyl group of tyrosine, serine and/or threonine residues of proteins. Protein kinases are categorized into families by the substrates they phosphorylate, for example, protein tyrosine kinases (PTK) and protein serine/threonine kinases.

Phosphorylation via protein kinase(s) results in a functional change of the target protein (substrate) by changing enzyme activity, cellular location or association with other proteins. Protein kinases play vital role, not only in controlling cell growth and differentiation, but also in regulating a wide variety of cellular signal transduction pathways in which protein kinases effectively regulate production of growth factors and various cytokines such as tumor necrosis factor (TNF)-α. Examples of protein-tyrosine kinases include SYK, PYK2, FAK, ALK, AXL, CSF1R, FLT3, JAK2 (JH1domain-catalytic), JAK3 (JH1domain-catalytic), KIT, KIT (D816V), KIT (V559D, T670I), PDGFRB, RET, TYK2 and ZAP70. Examples of protein-serine/threonine kinases include PIM1, AURKA, AURKB, BMPR2, JNK1, JNK2, JNK3, LKB1, LRRK2, LRRK2(G2019S), MLK1, PAK-4, PLK4, RSK2 (Kin.Dom.1-N-terminal), SNARK, SRPK3 and TAK1.

Mis-regulation of these protein kinases has been implicated in numerous diseases and disorders such as central nervous system disorders (e.g., Alzheimer's disease), inflammatory and autoimmune disorders (e.g., asthma, rheumatoid arthritis, Crohn's disease, and inflammatory bowel syndrome, and psoriasis), bone diseases (e.g., osteoporosis), metabolic disorders (e.g., diabetes), blood vessel proliferative disorders, ocular diseases, cardiovascular disease, cancer, restenosis, pain sensation, transplant rejection and infectious diseases. Although biological and clinical importance of protein kinases has been recognized in the field, a continuing need exists for compounds which inhibit protein kinases to provide an effective and safe clinical therapy for the diseases associated with or mediated by protein kinases. A need also exists for methods of administering such compounds, pharmaceutical formulations and medicaments to patients or subjects in need thereof.

SUMMARY OF THE INVENTION

The present invention provides a compound of Formula I, or individual stereoisomers, mixture of isomers, or pharmaceutically acceptable salt thereof,

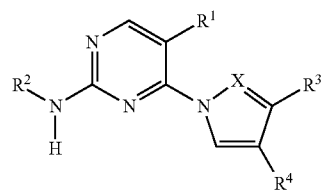

Formula I wherein:

X is CH or N;

$R^1$ is selected from H, halo, CN, $C_1$-$C_{10}$ alkyl or halo($C_1$-$C_4$) alkyl, wherein $C_1$-$C_{10}$ alkyl, or halo($C_1$-$C_4$)alkyl is optionally substituted;

$R^2$ is aryl, cycloalkyl, arylalkyl, or heterocyclyl, wherein the aryl, cycloalkyl, arylalkyl, or heterocyclyl is optionally and independently substituted at one or more carbon atoms with 1-4 $R^5$ or $R^{5a}$ groups; and wherein aryl and heterocyclyl having one or more nitrogen atoms is optionally and independently substituted at one or more nitrogen atoms with 1-4 $R^6$ or $R^{6a}$ groups;

$R^3$ is independently halo, CN, or $R^7$; and $R^4$ is selected from $(CH_2)_n$OH, $(CH_2)_n$NR$^{11}$R$^{12}$, C(O)NHR$^7$, C(O)NR$^{11}$R$^{12}$, C(O)OR$^7$, C(O)R$^7$, C(O)NR$^7$R$^7$, C(O)NR$^7$R$^8$, $(CH_2)_n$NR$^7$R$^7$, $(CH_2)_n$NR$^7$R$^8$, $(CH_2)_n$CN, $(CH_2)_n$SR$^7$, $(CH_2)_n$S(O)$_n$R$^7$, or $(CH_2)_n$S(O)$_n$NR$^7$R$^7$, wherein each n is independently 1 or 2;

wherein:

Each $R^5$ is independently selected from halo, $CF_3$, SR$^7$, OR$^7$, OC(O)R$^7$, O(CH$_2$)$_n$NR$^7$R$^7$, O(CH$_2$)$_n$NR$^{11}$R$^{12}$, O(CH$_2$)$_n$R$^7$, O(CH$_2$)$_n$C(O)NR$^{11}$R$^{12}$, O(CH$_2$)$_n$C(O) NR$^7$R$^7$, NR$^7$R$^7$, NR$^7$R$^8$, NHC(O)NH$_2$, C(O)OR$^7$, NO$_2$, CN, C(O)R$^7$, OSO$_2$CH$_3$, S(O)$_n$R$^7$, S(O)$_n$NR$^7$R$^7$, NR$^7$C (O)NR$^7$R$^7$, NR$^7$C(O)R$^7$, NR$^7$C(O)OR$^7$, NR$^7$S(O)$_n$R$^7$, or NR$^{11}$R$^{12}$, wherein each n is independently 1 or 2;

Each $R^{5a}$ is independently selected from amino, halo, hydroxy, $C_1$-$C_{10}$ alkyl, $C_2$-$C_{10}$alkenyl, $C_3$-$C_{10}$ alkynyl, $C_3$-$C_{12}$cycloalkyl, $C_5$-$C_{10}$cycloalkenyl, alkoxy, haloalkyl, aryl, heteroaryl, or heterocyclyl, wherein the $C_1$-$C_{10}$ alkyl, $C_2$-$C_{10}$alkenyl, $C_3$-$C_{10}$ alkynyl, $C_3$-$C_{12}$cycloalkyl, $C_5$-$C_{10}$cycloalkenyl, alkoxy, haloalkyl, aryl, heteroaryl, or heterocyclyl is optionally and independently substituted with 1 to 3 groups selected from halo, hydroxy, alkyl, $R^9$, or $R^{10}$;

Each $R^6$ is independently $R^7$, C(O)CH$_2$CN, C(O)R$^7$, C(O) OR$^7$, CO$_2$($C_1$-$C_6$alkyl), C(O)NR$^7$R$^7$, SO$_2$NR$^7$R$^7$, or SO$_2$R$^7$;

Each $R^{6a}$ is independently hydroxy, $C_1$-$C_{10}$ alkyl, $C_2$-$C_{10}$ alkenyl, $C_3$-$C_{10}$ alkynyl, $C_3$-$C_{12}$ cycloalkyl, $C_5$-$C_{10}$ cycloalkenyl, haloalkyl, wherein each $R^{6a}$ group is optionally and independently substituted with 1-3 groups selected from hydroxy, aryl, alkyl, halo, $R^9$, or $R^{10}$;

Each $R^7$ is independently H, $C_1$-$C_{10}$alkyl, $C_2$-$C_{10}$alkenyl, $C_3$-$C_{10}$alkynyl, $C_3$-$C_{12}$ cycloalkyl, $C_5$-$C_{12}$cycloalkenyl, aryl, aryl($C_1$-$C_4$)alkyl, haloalkyl, heteroaryl, or heterocyclyl, wherein the $C_1$-$C_{10}$alkyl, $C_2$-$C_{10}$alkenyl, $C_3$-$C_{10}$alkynyl, $C_3$-$C_{12}$ cycloalkyl, $C_5$-$C_{12}$cycloalkenyl, aryl, aryl($C_1$-$C_4$)alkyl, haloalkyl, heteroaryl, or heterocyclyl is optionally and independently substituted with 1-4 groups selected from aryl, cycloalkyl, heteroaryl, heterocyclyl, alkyl, halo, amino, hydroxy, $R^9$, or $R^{10}$;

Each $R^8$ is independently C(O)R$^7$, C(O)OR$^7$, C(O)NR$^7$R$^7$, or S(O)$_n$R$^7$, wherein n is 1 or 2;

Each $R^9$ is independently $CF_3$, $SR^7$, $OR^7$, $NR^7R^7$, $NR^{11}R^{12}$, $C(O)NR^7R^7$, $C(O)NR^{11}R^{12}$, $S(O)_nNR^7R^7$, or $S(O)_nR^7$, wherein each n is independently 1 or 2;

Each $R^{10}$ is $C(O)O(C_1-C_6)$alkyl, or halo$(C_1-C_4)$alkyl; and $R^{11}$ and $R^{12}$, taken together with the nitrogen atom to which they are bonded form:

i) a 3-8 membered saturated or partially saturated ring having no heteroatom other than the nitrogen atom to which $R^{11}$ and $R^{12}$ are bonded, wherein said 3-8 membered saturated or partially saturated ring is optionally and independently substituted with 1-4 groups selected from $R^5$ or $R^{5a}$ at one or more substitutable carbon atoms;

ii) a 5-8 membered saturated or partially saturated ring having 1-3 heteroatoms, in addition to the nitrogen atom to which $R^{11}$ and $R^{12}$ are bonded, wherein said 1-3 heteroatoms are independently selected from nitrogen, oxygen, sulfur, sulfone or sulfoxide, and wherein said 5-8 membered saturated or partially saturated ring having 1-3 heteroatoms is optionally and independently substituted with 1-4 groups selected from $R^5$ or $R^{5a}$ at one or more substitutable carbon atoms and at one or more substitutable nitrogen atoms with $R^6$ or $R^{6a}$;

iii) a 9-10 membered saturated or partially saturated bicyclic ring having no heteroatom other than the nitrogen atom to which and $R^{12}$ are bonded, wherein said 9-10 membered saturated or partially saturated bicyclic ring having no heteroatom is optionally substituted with 1-4 groups independently selected from $R^5$ or $R^{5a}$ at one or more substitutable carbon atoms;

iv) a 9-10 membered saturated or partially saturated bicyclic ring having 1-5 heteroatoms, in addition to the nitrogen atom to which $R^{11}$ and $R^{12}$ are bonded, wherein said heteroatoms are independently selected from nitrogen, oxygen, sulfur, sulfoxide, sulfone, carboxamide or sulfoxamide; or v) a 6-14 membered saturated or partially saturated bridged ring having 1-3 heteroatoms in addition to the nitrogen atom to which $R^{11}$ and $R^{12}$ are bonded, wherein said 1-3 heteroatoms are independently selected from nitrogen, oxygen, sulfur, sulfone, or sulfoxide, and wherein said 6-14 membered saturated or partially saturated bridged ring having 1-3 heteroatoms is optionally and independently substituted with 1-4 groups selected from $R^5$ or $R^{5a}$ at one or more substitutable carbon atoms and at one or more substitutable nitrogen atoms with $R^6$ or $R^{6a}$;

or a pharmaceutically acceptable salt thereof.

In certain aspects, $R^1$ is selected from H, F, Cl, Br, $CF_3$, or $CH_3$. $R^1$ is optionally substituted.

In certain aspects, $R^2$ is aryl, cycloalkyl, arylalkyl, or heterocyclyl. The aryl, cycloalkyl, arylalkyl, or heterocyclyl is optionally and independently substituted at one or more carbon atoms with 1-4 $R^5$ or $R^{5a}$ groups. In one embodiment, $R^2$ can be an aryl and the aryl optionally substituted at one or more carbon atoms with 1-4 $R^5$ or $R^{5a}$ groups. The aryl of $R^2$ can be heteroaryl containing one or more heteroatoms independently selected from nitrogen, oxygen, sulfur, sulfoxide, or sulfone. The heteroaryl and heterocyclyl of $R^2$ can have one or more nitrogen atoms optionally and independently substituted with 1-4 $R^6$ or $R^{6a}$ groups. The aryl group of $R^2$ can be, for example, a 5-6 membered monocyclic aryl group having 0-3 heteroatoms independently selected from nitrogen, oxygen, or sulfur; an 8-10 membered bicyclic aryl group having 0-5 heteroatoms independently selected from nitrogen, oxygen, sulfur, sulfoxide, or sulfone; an 8-10 membered partially unsaturated bicyclic aryl group having 0-5 heteroatoms independently selected from nitrogen, oxygen, sulfur, sulfoxide, or sulfone; or an 8-10 membered partially unsaturated bicyclic aryl group having a carboxamide or sulfoxamide.

In one embodiment, the aryl of $R^2$ is a 5-6 membered monocyclic aryl group such as phenyl, pyrimidinyl, or pyridyl optionally and independently substituted with 1, 2, or 3 groups selected from methyl, ethyl, phenyl, 2-hydroxyethoxy, isopropyl, methoxy $OC_6H_5$, $OCH_2C_6H_5$, $OCH_2CH_2NR^{11}R^{12}$, $OCH_2CH_2NR^7R^7$, $OCH_2C(O)NR^{11}R^{12}$, $OCH_2C(O)NR^7R^7$, $CF_3$, $OSO_2CH_3$, $SO_2CH_3$, $SO_2NHCH_3$, or $NR^{11}R^{12}$.

In another embodiment, $R^2$ is an 8-10 membered bicyclic aryl group having 0-5 heteroatoms independently selected from nitrogen, oxygen, sulfur, or sulfoxide. The bicyclic aryl of $R^2$ is selected from indolyl, indazolyl, naphthyl, or quinolinyl optionally and independently substituted with 1, 2 or 3 groups selected from alkyl, alkoxy, halo, aryl, heteroaryl, cycloalkyl, $CF_3$, $OCF_3$, $C(O)$alkyl, $C(O)$aryl, $S(O)_2$alkyl at the substitutable carbon atoms or nitrogen atom, wherein alkyl, aryl, or heteroaryl is optionally substituted with hydroxy, amino or sulfone.

In another embodiment, $R^2$ is an 8-10 membered partially saturated bicyclic aryl group having 0-5 heteroatoms independently selected from nitrogen, oxygen, sulfur, sulfoxide, or sulfone. For example, the 8-10 membered partially saturated bicyclic group is dihydrobenzodioxinyl, tetrahydronaphthyl, or dihydroindenyl optionally and independently substituted with 1, 2, or 3 groups selected from alkyl, aryl, heteroaryl, alkoxy, halo, $CF_3$, $OCF_3$, or $SO_2CH_3$ at substitutable carbon atoms.

In certain aspects, $R^3$ is H, methyl, cyclopropyl, isopropyl, furanyl, $CF_3$ or phenyl.

In one embodiment, $R^4$ is $C(O)OR^7$ and $R^7$ is independently H, $C_1-C_{10}$ alkyl, $C_2-C_{10}$ alkenyl, $C_3-C_{10}$ alkynyl, $C_3-C_{12}$ cycloalkyl, $C_5-C_{12}$ cycloalkenyl, aryl, haloalkyl, heteroaryl, or heterocyclyl. $C_1-C_{10}$ alkyl, $C_2-C_{10}$ alkenyl, $C_3-C_{10}$ alkynyl, $C_3-C_{12}$ cycloalkyl, $C_5-C_{12}$ cycloalkenyl, aryl, haloalkyl, heteroaryl, or heterocyclyl is optionally and independently substituted with 1-4 groups selected from hydroxy, halo, amino, aryl, cycloalkyl, heterocyclyl, alkyl, $R^9$ or $R^{19}$. For example, $R^7$ is independently H or $C_1-C_{10}$ alkyl. Further, the $C_1-C_{10}$ alkyl of $R^7$ can be optionally and independently substituted with 1-4 groups selected from halo, hydroxy, amino, $C_1-C_6$ alkyl, $C_1-C_6$ alkoxy, $C_1-C_6$ alkylamino, or di$C_1-C_6$ alkylamino.

In one embodiment, $R^4$ is $C(O)R^7$ and $R^7$ of $C(O)R^7$ is independently $C_1-C_{10}$ alkyl, $C_2-C_{10}$ alkenyl, $C_3-C_{10}$ alkynyl, $C_3-C_{12}$ cycloalkyl, $C_5-C_{12}$ cycloalkenyl, aryl, haloalkyl, or heterocyclyl optionally and independently substituted with 1-4 groups selected from halo, aryl, cycloalkyl, heterocyclyl, alkyl, $R^9$ or $R^{19}$. For example, $R^7$ can be independently selected from H or $C_1-C_{10}$ alkyl. The $C_1-C_{10}$ alkyl of $R^7$ can be optionally and independently substituted with 1-4 groups from halo, hydroxyl, amino, $C_1-C_6$ alkyl, $C_1-C_6$ alkoxy, $C_1-C_6$ alkylamino or di$C_1-C_6$ alkylamino.

In one embodiment, $R^4$ is $C(O)NHR^7$ and $R^7$ is independently H, $C_1-C_{10}$ alkyl, $C_2-C_{10}$ alkenyl, $C_2-C_{10}$ alkynyl, $C_3-C_{12}$ cycloalkyl, $C_4-C_{12}$ cycloalkenyl, aryl, arylalkyl, haloalkyl, or heterocyclyl. $C_1-C_{10}$ alkyl, $C_2-C_{10}$ alkenyl, $C_2-C_{10}$ alkynyl, $C_3-C_{12}$ cycloalkyl, $C_4-C_{12}$ cycloalkenyl, aryl, arylalkyl, haloalkyl, or heterocyclyl is optionally and independently substituted with 1-4 groups selected from halo, aryl, cycloalkyl, heterocyclyl, alkyl, $R^9$ or $R^{10}$. In one embodiment, $R^7$ can be selected from $C_1-C_{10}$ alkyl or aryl. The aryl can be phenyl optionally and independently substituted with 1, 2, or 3 groups selected from methyl, methoxy, hydroxy, $OC(O)R^7$, $CH_2OH$, $CH_2CH_2OH$, $NH_2$, $NR^7R^7$, NHC(O)NHR$^7$, NHSO$_2$R$^7$, C(O)OR$^7$, C(O)NHR$^7$, CF$_3$, or SO$_2$CH$_3$. Preferred substituents are methyl, methoxy, CF$_3$, and SO$_2$CH$_3$. The C$_1$-C$_{10}$ alkyl of R$^7$ is optionally and independently substituted with 1-4 groups selected from amino, halo, hydroxyl, phenyl, phenylalkyl, C$_1$-C$_6$ alkyl, C$_1$-C$_6$ alkoxy, C$_1$-C$_6$ alkylamino or diC$_1$-C$_6$ alkylamino.

In one embodiment, R$^4$ is C(O)NR$^{11}$R$^{12}$ and R$^{11}$ and R$^{12}$, taken together with the nitrogen atom to which they are bonded form: (i) a 3-8 membered saturated or partially saturated ring having no heteroatom other than the nitrogen atom to which R$^{11}$ and R$^{12}$ are bonded, in which the 3-8 membered saturated or partially saturated ring is optionally and independently substituted with 1-4 groups selected from R$^5$ or R$^{5a}$ at one or more substitutable carbon atoms; (ii) a 5-8 membered saturated or partially saturated ring having 1-3 heteroatoms, in addition to the nitrogen atom to which R$^{11}$ and R$^{12}$ are bonded, in which the 1-3 heteroatoms are independently selected from nitrogen, oxygen, sulfur, sulfone or sulfoxide, and in which said 5-8 membered saturated or partially saturated ring having 1-3 heteroatoms is optionally and independently substituted with 1-4 groups selected from R$^5$ or R$^{5a}$ at one or more substitutable carbon atoms and at one or more substitutable nitrogen atoms with R$^6$ or R$^{6a}$; (iii) a 9-10 membered saturated or partially saturated bicyclic ring having no heteroatom other than the nitrogen atom to which R$^{11}$ and R$^{12}$ are bonded, in which the 9-10 membered saturated or partially saturated bicyclic ring having no heteroatom other than the bound nitrogen atom is optionally substituted with 1-4 groups independently selected from R$^5$ or R$^{5a}$ at one or more substitutable carbon atoms; or (iv) a 9-10 membered saturated or partially saturated bicyclic ring having 1-5 heteroatoms, in addition to the nitrogen atom to which R$^{11}$ and R$^{12}$ are bonded, wherein said heteroatoms are independently selected from nitrogen, oxygen, sulfur, sulfoxide, sulfone, carboxamide or sulfoxamide. For example, the 3-8 membered saturated or partially saturated ring having no heteroatom other than the bound nitrogen atom can be optionally and independently substituted with 1-4 hydroxy or amino groups.

In one embodiment, R$^4$ is (CH$_2$)$_n$NR$^7$R$^7$. R$^7$ of (CH$_2$)$_n$NR$^7$R$^7$ is independently H, C$_1$-C$_{10}$ alkyl, C$_2$-C$_{10}$ alkenyl, C$_3$-C$_{10}$ alkynyl, C$_3$-C$_{12}$ cycloalkyl, C$_5$-C$_{12}$ cycloalkenyl, aryl, haloalkyl or heterocyclyl. R$^7$ of (CH$_2$)$_n$NR$^7$R$^7$ is optionally and independently substituted with 1-4 groups selected from halo, aryl, cycloalkyl, heterocyclyl, alkyl, R$^9$ or R$^{10}$. For example, R$^7$ can be independently H, C$_1$-C$_{10}$ alkyl, C$_3$-C$_{12}$ cycloalkyl, aryl, or heterocyclyl and R$^7$ is optionally and independently substituted with 1-4 groups selected from hydroxyl, amino, aryl, alkyl or halo. In one embodiment, R$^7$ is independently H or C$_1$-C$_{10}$ alkyl. The C$_1$-C$_{10}$ alkyl is optionally substituted with phenyl. The phenyl can be optionally and independently substituted with one or more alkyl, halo, amino, or hydroxyl.

In some aspects, R$^4$ is (CH$_2$)$_n$NR$^{11}$R$^{12}$ and R$^{11}$ and R$^{12}$, taken together with the nitrogen atom to which they are bonded form: (i) a 3-8 membered saturated or partially saturated ring having no heteroatom other than the nitrogen atom to which R$^{11}$ and R$^{12}$ are bonded, wherein said 3-8 membered saturated or partially saturated ring is optionally and independently substituted with 1-4 groups selected from R$^5$ or R$^{5a}$ at one or more substitutable carbon atoms; (ii) a 5-8 membered saturated or partially saturated ring having 1-3 heteroatoms, in addition to the nitrogen atom to which R$^{11}$ and R$^{12}$ are bonded, wherein said 1-3 heteroatoms are independently selected from nitrogen, oxygen, sulfur, sulfone or sulfoxide, and wherein said 5-8 membered saturated or partially saturated ring having 1-3 heteroatoms is optionally and independently substituted with 1-4 groups selected from R$^5$ or R$^{5a}$ at one or more substitutable carbon atoms and at one or more substitutable nitrogen atoms with R$^6$ or R$^{6a}$; (iii) a 9-10 membered saturated or partially saturated bicyclic ring having no heteroatom other than the nitrogen atom to which R$^{11}$ and R$^{12}$ are bonded, wherein said 9-10 membered saturated or partially saturated bicyclic ring having no heteroatom is optionally substituted with 1-4 groups independently selected from R$^5$ or R$^{5a}$ at one or more substitutable carbon atoms; (iv) a 9-10 membered saturated or partially saturated bicyclic ring having 1-5 heteroatoms, in addition to the nitrogen atom to which R$^{11}$ and R$^{12}$ are bonded, wherein said heteroatoms are independently selected from nitrogen, oxygen, sulfur, sulfoxide, sulfone, carboxamide or sulfoxamide; or (v) a 6-14 membered saturated or partially saturated bridged ring having 1-3 heteroatoms in addition to the nitrogen atom to which R$^{11}$ and R$^{12}$ are bonded, wherein said 1-3 heteroatoms are independently selected from nitrogen, oxygen, sulfur, sulfone, or sulfoxide, and wherein said 6-14 membered saturated or partially saturated bridged ring having 1-3 heteroatoms is optionally and independently substituted with 1-4 groups selected from R$^5$ or R$^{5a}$ at one or more substitutable carbon atoms and at one or more substitutable nitrogen atoms with R$^6$ or R$^{6a}$.

In one embodiment, R$^4$ is (CH$_2$)$_n$NR$^{11}$R$^{12}$ and R$^{11}$ and R$^{12}$, taken together with the nitrogen atom to which they are bonded form a 3-8 membered saturated or partially saturated ring having no heteroatom other than the nitrogen atom to which R$^{11}$ and R$^{12}$ are bonded. The 3-8 membered saturated or partially saturated ring having no heteroatom other than the bound nitrogen atom is optionally and independently substituted with 1-4 groups selected from R$^5$ or R$^{5a}$ at one or more substitutable carbon atoms. The 3-8 membered saturated or partially saturated ring having no heteroatom other than the bound nitrogen can be a 4, 5 or 6 membered saturated ring optionally and independently substituted with one or more hydroxy, OC(O)R$^7$, CH$_2$OH, CH$_2$CH$_2$OH, NH$_2$, NR$^7$R$^7$, NHC(O)NHR$^7$, NHSO$_2$R$^7$, C(O)OR$^7$ or C(O)NHR$^7$ at one or more substitutable carbon atoms. Preferably, the 3-8 membered ring is selected from azetidinyl, pyrrolidinyl, or piperidinyl optionally and independently substituted with hydroxy, halo, OC(O)R$^7$, CH$_2$OH, CH$_2$CH$_2$OH, NH$_2$, NR$^7$R$^7$, NHC(O)NHR$^7$, NHSO$_2$R$^7$, C(O)OR$^7$, or C(O)NHR$^7$ at one or more substitutable carbon atoms.

In one embodiment, R$^4$ is (CH$_2$)$_n$NR$^{11}$R$^{12}$ and R$^{11}$ and R$^{12}$, taken together with the nitrogen atom to which they are bonded form a 5-8 membered saturated or partially saturated ring having 1-3 heteroatoms, in addition to the nitrogen atom to which R$^{11}$ and R$^{12}$ are bonded. The 1-3 heteroatoms are independently selected from nitrogen, oxygen, sulfur, sulfone or sulfoxide, and the 5-8 membered saturated or partially saturated ring having 1-3 heteroatoms is optionally and independently substituted with 1-4 groups selected from R$^5$ or R$^{5a}$ at one or more substitutable carbon atoms and at one or more substitutable nitrogen atoms with R$^6$ or R$^{6a}$. For example, the 5-8 membered saturated or partially saturated ring having 1-3 heteroatoms is a 6 or 7 membered saturated ring having 1 heteroatom. The heteroatom can be nitrogen optionally substituted with C$_1$-C$_{10}$ alkyl, hydroxyl C$_2$-C$_{10}$alkyl, or C(O)NHR$^7$. Alternatively, the heteroatom can be oxygen. In one embodiment, the oxygen, together with R$^{11}$, R$^{12}$ and with the nitrogen atom to which they are bonded, can form morpholino. The 5-8 membered saturated or partially saturated ring having 1-3 heteroatoms can be morpholino, thiomorpholino, piperazinyl, or homopiperazinyl. The piperazinyl or homopiperazinyl is optionally and independently substituted with hydroxy, C$_1$-C$_{10}$ alkyl, CH$_2$CH$_2$OH, C(O)R$^7$, C(O)NHR$^7$, SO$_2$R$^7$, SO$_2$NHR$^7$ or C(O)OR$^7$ at the nitrogen atom.

In one embodiment, $R^4$ is $(CH_2)_n NR^{11}R^{12}$ and $R^{11}$ and $R^{12}$, taken together with the nitrogen atom to which they are bonded can form a 9-10 membered saturated or partially saturated bicyclic ring having no heteroatom other than the nitrogen atom to which $R^{11}$ and $R^{12}$ are bonded. The 9-10 membered saturated or partially saturated bicyclic ring having no heteroatom other than the bound nitrogen atom is optionally substituted with 1-4 groups independently selected from $R^5$ or $R^{5a}$ at one or more substitutable carbon atoms. For example, the bicyclic ring can form tetrahydroisoquinoline. The bicyclic ring can also contain an aryl group within the ring.

In one embodiment, $R^4$ is $(CH_2)_n NR^{11}R^{12}$ and $R^{11}$ and $R^{12}$, taken together with the nitrogen atom to which they are bonded can form a 9-10 membered saturated or partially saturated bicyclic ring having 1-5 heteroatoms, in addition to the nitrogen atom to which $R^{11}$ and $R^{12}$ are bonded. The 1-5 heteroatoms are independently selected from nitrogen, oxygen, sulfur, sulfoxide, sulfone, carboxamide, or sulfoxamide. The 9-10 membered saturated or partially saturated bicyclic ring having 1-5 heteroatoms can be optionally and independently substituted with 1-4 groups selected from $R^5$ or $R^{5a}$ at one or more substitutable carbon atoms and at one or more substitutable nitrogen atoms with $R^6$ or $R^{6a}$. The bicyclic ring can also contain an aryl group within the ring.

In one embodiment, $R^4$ is $(CH_2)_n NR^{11}R^{12}$ and $R^{11}$ and $R^{12}$, taken together with the nitrogen atom to which they are bonded can form a 6-14 membered saturated or partially saturated bridged ring having 1-3 heteroatoms in addition to the nitrogen atom to which $R^{11}$ and $R^{12}$ are bonded, wherein said 1-3 heteroatoms are independently selected from nitrogen, oxygen, sulfur, sulfone, or sulfoxide, and wherein said 6-14 membered saturated or partially saturated bridged ring having 1-3 heteroatoms is optionally and independently substituted with 1-4 groups selected from $R^5$ or $R^{5a}$ at one or more substitutable carbon atoms and at one or more substitutable nitrogen atoms with $R^6$ or $R^{6a}$.

The present invention also relates to compositions comprising these compounds, methods of making these compounds, methods of inhibiting enzyme activity, particularly SYK, PYK2, FAK, ZAP70, PIM1, RET, FLT3, JAK2 and LRRK2 kinase activity, through use of these compounds, and method of treating disease or disease symptoms in a mammal, particularly where inhibition of the kinase activity, can affect disease outcome.

The compounds of Formula (I) are useful for inhibiting one or more protein kinases and for treating diseases and disorders that are mediated by the protein kinases, such as cancer, autoimmune diseases, infection, cardiovascular disease, and neurodegenerative diseases.

In one aspect, the present invention provides pharmaceutical compositions comprising a compound of Formula (I) and a pharmaceutically acceptable carrier. In certain embodiments, such pharmaceutical compositions are formulated for intravenous administration, subcutaneous administration, inhalation, oral administration, rectal administration, parenteral, intravitreal administration, intramuscular administration, intranasal administration, dermal administration, topical administration, otic administration, ophthalmic administration, buccal administration, tracheal administration, bronchial administration, or sublingual administration. In other embodiments, such pharmaceutical composition are formulated as tablets, a pills, capsules, a liquid, an inhalant, a nasal spray solution, a suppository, a solution, a gel, an emulsion, an ointment, eye drops or ear drops.

In one aspect, the present invention provides methods of inhibiting SYK, PYK2, FAK, ZAP70, PIM1, FLT3, RET, JAK2, JAK3, LRRK2, LRRK2(G2019S), ABL1(T315I), AURKB, AXL, FLT3, KIT, KIT(D816V), KIT(V559D, T670I), MKNK2, MLK1, PDGFRB, PLK3, RET, SNARK, SRPK3, TAK1, or TYK2 signaling in vivo or in vitro, comprising administering to said subject an effective amount of the compound of claim 1.

In one aspect, the present invention provides methods for treating a cell-proliferative disease or condition, such as cancer, comprising administering to a subject in need of such treatment a therapeutically effective amount of the compound of Formula (I) or pharmaceutically acceptable salts, pharmaceutical compositions or medicaments thereof, wherein the cell proliferative disease or condition include, for example, lymphoma, osteosarcoma, melanoma, breast cancer, renal cancer, prostate cancer, colorectal cancer, thyroid cancer, ovarian cancer, pancreatic cancer, neuronal cancer, lung cancer, uterine cancer or gastrointestinal cancer. In one aspect, the present invention provides methods of inhibiting growth of cancer cells with the compound of claim 1 or a pharmaceutically acceptable salt thereof.

In another aspect, the present invention provides a medicament for treating a SYK, PYK2, FAK, ZAP70, PIM1, FLT3, RET, JAK2, JAK3, LRRK2, LRRK2(G2019S), ABL1 (T315I), AURKB, AXL, FLT3, KIT, KIT(D816V), KIT (V559D,T670I), MKNK2, MLK1, PDGFRB, PLK3, RET, SNARK, SRPK3, TAK1, or TYK2-mediated disease, disorder or condition in a patient comprising a therapeutically effective amount of the compound of Formula (I).

In another aspect, the present invention provides the use of the compound of Formula (I) in the manufacture of a medicament for treating a SYK, PYK2, FAK, ZAP70, PIM1, FLT3, RET, JAK2, JAK3, LRRK2, LRRK2(G2019S), ABL1 (T315I), AURKB, AXL, FLT3, KIT, KIT(D816V), KIT (V559D,T670I), MKNK2, MLK1, PDGFRB, PLK3, RET, SNARK, SRPK3, TAK1, or TYK2-mediated disease, disorder or condition.

In another aspect, the present invention provides methods for inhibiting a protein kinase, comprising administering to a subject in need thereof, a therapeutically effective amount of the compound of Formula (I) or a pharmaceutically acceptable salt or pharmaceutical composition thereof. The protein kinase includes, but is not limited to, SYK, PYK2, FAK, ZAP70, PIM1, FLT3, RET, JAK2, JAK3, LRRK2, LRRK2 (G2019S), ABL1(T315I), AURKB, AXL, FLT3, KIT, KIT (D816V), KIT(V559D,T670I), MKNK2, MLK1, PDGFRB, PLK3, RET, SNARK, SRPK3, TAK1, or TYK2 kinase.

In another aspect, the present invention provides methods for inhibiting a protein kinase, comprising contacting to a cell with the compound of Formula (I). In certain embodiment, the compound of Formula (I) effectively inhibits activity of one or more kinases selected from SYK, PYK2, FAK, ZAP70, PIM1, FLT3, RET, JAK2, JAK3, LRRK2, LRRK2 (G2019S), ABL1(T315I), AURKB, AXL, FLT3, KIT, KIT (D816V), KIT(V559D,T670I), MKNK2, MLK1, PDGFRB, PLK3, RET, SNARK, SRPK3, TAK1, or TYK2.

In another aspect, the present invention provides methods for treating a protein kinase-mediated disease or condition comprising administering to a subject in need of such treatment a therapeutically effective amount of the compound of Formula (I) or a pharmaceutically acceptable salt, a pharmaceutical composition or a medicament thereof. The protein kinase includes, but is not limited to, SYK, PYK2, FAK, ZAP70, PIM1, FLT3, RET, JAK2, JAK3, LRRK2, LRRK2 (G2019S ABL1(T315I), AURKB, AXL, FLT3, KIT, KIT (D816V), KIT(V559D,T670I), MKNK2, MLK1, PDGFRB, PLK3, RET, SNARK, SRPK3, TAK1, or TYK2.

In certain embodiments, protein kinase-mediated diseases or conditions are inflammatory diseases or conditions, respiratory diseases or autoimmune diseases or conditions, such as asthma, chronic obstructive pulmonary disease (COPD), adult respiratory distress syndrome (ARDS), ulcerative colitis, Crohn's disease, bronchitis, dermatitis, allergic rhinitis, psoriasis, scleroderma, urticaria, rheumatoid arthritis, multiple sclerosis, cancer, breast cancer, HIV associated diseases or lupus.

In another aspect, the present invention provides methods for treating a neurological/neurodegenerative disease or condition by administering to a subject a therapeutically effective amount of the compound of Formula (I) or a pharmaceutically acceptable salt. In certain embodiment, such neurological/neurodegenerative disease or condition includes, for example, Alzheimer's disease, cerebral edema, cerebral ischemia, multiple sclerosis, neuropathies, Parkinson's disease, blunt or surgical trauma (including post-surgical cognitive dysfunction and spinal cord or brain stem injury), as well as the neurological aspects of disorders such as degenerative disc disease and sciatica.

In another aspect, the present invention provides methods for treating a cardiovascular disease by administering to a subject a therapeutically effective amount of the compound of Formula (I) or a pharmaceutically acceptable salt. Such a cardiovascular disease affects the heart or blood vessels and includes, for example, atherosclerosis, arrhythmia, angina, myocardial ischemia, myocardial infarction, cardiac or vascular aneurysm, vasculitis, stroke, peripheral obstructive arteriopathy of a limb, an organ, or a tissue, reperfusion injury following ischemia of an organ or a tissue, endotoxic, surgical, or traumatic shock, hypertension, valvular heart disease, heart failure, abnormal blood pressure, vasoconstriction, vascular abnormality, or inflammation.

In another aspect, the present invention provides methods of treating a kinase-mediated disease or condition by administering to a subject a therapeutically effective amount of the compound of Formula (I) or a pharmaceutically acceptable salt in combination with a second therapeutic agent.

In the above methods for using the compound of the invention, the compound of Formula (I) or a pharmaceutically acceptable salt is administered to a system comprising cells or tissues. In certain embodiments, the compound of Formula (I), a pharmaceutically acceptable salt, a pharmaceutical composition or a medicament thereof is administered to a human or animal subject.

DETAILED DESCRIPTION OF THE INVENTION

The present invention provides a group of pyrollopyrimidine derivatives and pharmaceutically acceptable salts thereof that are useful for inhibiting one or more protein kinases and for treating diseases and disorders that are mediated by the protein kinase, for example, cell proliferative disease and disorder such as cancer, autoimmune diseases, infection, cardiovascular disease, and neurodegenerative disease and disorder such as Alzheimer's disease. The present invention also provides methods for synthesizing and administering the pyrollopyrimidine derivatives. The present invention also provides pharmaceutical formulations comprising at least one of the compounds of the present invention together with a pharmaceutically acceptable carrier, diluent or excipient therefor. The invention also provides useful intermediates generated during syntheses of the pyrollopyrimidine derivative compounds.

The present invention provides a compound of Formula I, or individual stereoisomer, mixture of isomers, or pharmaceutically acceptable salt thereof,

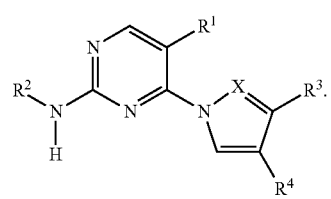

Formula I

X is CH or N.

$R^1$ is selected from H, halo, CN, $C_1$-$C_{10}$alkyl, or halo($C_1$-$C_4$)alkyl. For example, $R^1$ can be H, F, Cl, Br, $CF_3$ or $CH_3$. $C_1$-$C_{10}$alkyl, or halo($C_1$-$C_4$)alkyl of $R^1$ can be optionally substituted with one or more suitable substituents, for example, halo, amino, hydroxy, alkoxy, or haloalkyl.

$R^2$ is aryl, cycloalkyl, arylalkyl, or heterocyclyl. The aryl, cycloalkyl, arylalkyl, or heterocyclyl group of $R^2$ is optionally and independently substituted at one or more carbon atoms with 1-4 $R^5$ or $R^{5a}$ groups; and at one or more nitrogen atoms with 1-4 $R^6$ or $R^{6a}$ groups. $R^2$ can be an aryl, arylalkyl, or heterocyclyl group having one or more heteroatoms selected from nitrogen, oxygen, sulfur, sulfoxide, sulfone, carboxamide, or sulfoxamide. Such heteroaryl, heteroarylalkyl, or heterocyclyl of $R^2$ has one or more nitrogen heteroatoms optionally and independently substituted with 1-4 $R^6$ or $R^{6a}$ groups.

The aryl groups of $R^2$, and in general, include, but are not limited to: (1) a 5-6 membered monocyclic aryl group having 0-3 heteroatoms independently selected from nitrogen, oxygen, or sulfur; (2) an 8-10 membered bicyclic aryl group having 0-5 heteroatoms independently selected from nitrogen, oxygen, sulfur, sulfoxide, or sulfone; (3) an 8-10 membered partially saturated bicyclic aryl group having 0-5 heteroatoms independently selected from nitrogen, oxygen, sulfur, sulfoxide, or sulfone; or (4) an 8-10 membered partially saturated bicyclic aryl group having a carboxamide or sulfoxamide. Non-limiting examples of the aryl groups of $R^2$ include phenyl, 3-chlorophenyl, 2,6-dibromophenyl, pyrimidinyl, pyridyl, 3-methylpyridyl, benzothienyl, 2,4,6-tribromophenyl, 4-ethylbenzothienyl, furanyl, benzofuranyl, indolyl, indazolyl, dihydrobenzodioxinyl, dihydroindenyl, 3,4-diethylfuranyl, naphthyl, tetrahydronaphtyl, quinolinyl, 4,7-dichloronaphthyl, pyrrole, pyrazole, imidazole, thiazole and the like. The aryl group of $R^2$ can be optionally substituted.

Specifically, $R^2$ can be a 5-6 membered monocyclic aryl group having 0-3 heteroatoms independently selected from nitrogen, oxygen, or sulfur. For example, the 5-6 membered monocyclic aryl of $R^2$ is phenyl optionally and independently substituted with 1, 2 or 3 groups selected from methyl, ethyl, isopropyl, methoxy, 2-hydroxyethoxy, $CF_3$, $OC_6H_5$, $OCH_2C_6H_5$, $OCH_2CH_2NR^{11}R^{12}$, $OCH_2CH_2NR^7R^7$, $OCH_2C(O)NR^{11}R^{12}$, $OCH_2C(O)NR^7R^7$, $OSO_2CH_3$, $SO_2CH_3$, $SO_2NHCH_3$, or $NR^{11}R^{12}$. Hydroxyethoxy is $OCH_2CH_2OH$. Briefly, $R^{11}R^{12}$ of $OCH_2CH_2NR^{11}R^{12}$, $OCH_2C(O)NR^{11}R^{12}$, or $NR^{11}R^{12}$, taken together with the nitrogen atom to which they are bonded can form: (i) a 3-8 membered saturated or partially saturated ring having no heteroatom other than the nitrogen atom to which $R^{11}$ and $R^{12}$ are bonded, for example, pyrrolidinyl or piperidinyl; or (ii) a 5-8 membered saturated or partially saturated ring having 1-3 heteroatoms, in addition to the nitrogen atom to which $R^{11}$ and $R^{12}$ are bonded, for example, morpholino, piperazinyl, or homopiperazinyl. Descriptions of $R^{11}R^{12}$ are further discussed in detail below.

$R^2$ can be an 8-10 membered bicyclic aryl group having 0-5 heteroatoms independently selected from nitrogen, oxygen, sulfur, sulfoxide, or sulfone. For example, the 8-10 membered bicyclic aryl group can be selected from indolyl, indazolyl, benzothiophenyl, benzothiazolyl, benzofuranyl, naphthyl, or quinolinyl optionally and independently substituted with 1, 2 or 3 groups selected from alkyl, aryl, heteroaryl, alkoxy, halo, haloalkyl, cycloalkyl, or sulfone, such as $CF_3$, $OCF_3$, $C(O)C_6H_5$, or $S(O)_2CH_3$ at the substitutable carbon atoms or nitrogen atom, wherein alkyl, aryl or heteroaryl is optionally substituted with hydroxyl, amino, or sulfone.

$R^2$ can be an 8-10 membered partially saturated bicyclic group having a phenyl ring fused to a non-aromatic carbocyclic or heterocyclic ring having 0-5 heteroatoms independently selected from nitrogen, oxygen, sulfur, sulfoxide, or sulfone. For example, the 8-10 membered partially saturated bicyclic group is dihydroindenyl, tetrahydronaphthyl, or dihydrobenzodioxinyl optionally and independently substituted with 1, 2, or 3 groups selected from alkyl, aryl, heteroaryl, alkoxy, halo, $CF_3$, $OCF_3$, or $SO_2CH_3$ at the substitutable carbon atoms.

$R^3$ can be H, halo, CN or $R^7$. For example, $R^3$ is selected from H, $C_1$-$C_6$ alkyl, cycloalkyl, or aryl. Preferably, $R^3$ is selected from H, cyclopropyl, isopropyl, furanyl, methyl, ethyl, $CF_3$, or phenyl. The methyl, ethyl, or phenyl can be optionally and independently substituted with one or more groups selected from halo, aryl, cycloalkyl, heterocyclyl, alkyl, $R^9$, or $R^{10}$.

Each $R^5$ is independently selected from halo, $CF_3$, $SR^7$, $OR^7$, $OC(O)R^7$, $O(CH_2)_nNR^7R^7$, $O(CH_2)_nNR^{11}R^{12}$, $O(CH_2)_nR^7$, $O(CH_2)_nC(O)NR^{11}R^{12}$, $O(CH_2)_nC(O)NR^7R^7$, $NR^7R^7$, $NR^7R^8$, $NHC(O)NH_2$, $C(O)OR^7$, $NO_2$, CN, $C(O)R^7$, $OSO_2CH_3$, $S(O)_nR^7$, $S(O)_nNR^7R^7$, $NR^7C(O)NR^7R^7$, $NR^7C(O)R^7$, $NR^7C(O)OR^7$, $NR^7S(O)_nR^7$, or $NR^{11}R^{12}$. Each n is independently 1 or 2.

Each $R^{5a}$ is independently selected amino, halo, hydroxy, $C_1$-$C_{10}$ alkyl, $C_2$-$C_{10}$alkenyl, $C_3$-$C_{10}$ alkynyl, $C_3$-$C_{12}$cycloalkyl, $C_5$-$C_{10}$cycloalkenyl, alkoxy, haloalkyl, aryl, heteroaryl, or heterocyclyl. The $C_1$-$C_{10}$ alkyl, $C_2$-$C_{10}$alkenyl, $C_3$-$C_{10}$ alkynyl, $C_3$-$C_{12}$cycloalkyl, $C_5$-$C_{10}$cycloalkenyl, alkoxy, haloalkyl, aryl, heteroaryl, or heterocyclyl of $R^{5a}$ is optionally and independently substituted with 1 to 3 groups selected from halo, hydroxy, alkyl, $R^9$, or $R^{10}$.

Each $R^6$ is independently $R^7$, $C(O)CH_2CN$, $C(O)R^7$, $C(O)OR^7$, $CO_2(C_1$-$C_6$alkyl), $C(O)NR^7R^7$, $SO_2NR^7R^7$, or $SO_2R^7$.

Each $R^{6a}$ is independently hydroxy, $C_1$-$C_{10}$ alkyl, $C_2$-$C_{10}$ alkenyl, $C_3$-$C_{10}$ alkynyl, $C_3$-$C_{12}$ cycloalkyl, $C_5$-$C_{10}$ cycloalkenyl, haloalkyl. Each $R^{6a}$ group is optionally and independently substituted with 1-3 groups selected from hydroxy, aryl, alkyl, halo, $R^9$, or $R^{10}$.

Each $R^7$ is independently H, $C_1$-$C_{10}$alkyl, $C_2$-$C_{10}$alkenyl, $C_3$-$C_{10}$alkynyl, $C_3$-$C_{12}$ cycloalkyl, $C_5$-$C_{12}$cycloalkenyl, aryl, aryl($C_1$-$C_4$)alkyl, haloalkyl, heteroaryl, or heterocyclyl. The $C_1$-$C_{10}$alkyl, $C_2$-$C_{10}$alkenyl, $C_3$-$C_{10}$alkynyl, $C_3$-$C_{12}$ cycloalkyl, $C_5$-$C_{12}$cycloalkenyl, aryl, aryl($C_1$-$C_4$)alkyl, haloalkyl, heteroaryl, or heterocyclyl is optionally and independently substituted with 1-4 groups selected from aryl, cycloalkyl, heteroaryl, heterocyclyl, alkyl, halo, amino, hydroxy, $R^9$, or $R^{10}$.

Each $R^8$ is independently $C(O)R^7$, $C(O)OR^7$, $C(O)NR^7R^7$ or $S(O)_nR^7$. n is 1 or 2.

Each $R^9$ is independently $CF_3$, $SR^7$, $OR^7$, $NR^7R^7$, $NR^{11}R^{12}$, $C(O)NR^7R^7$, $C(O)NR^{11}R^{12}$, $S(O)_nNR^7R^7$, or $S(O)_nR^7$, wherein each n is independently 1 or 2. Each n is independently 1 or 2.

Each $R^{10}$ is $C(O)O(C_1$-$C_6)$alkyl or halo($C_1$-$C_4$)alkyl.

$R^{11}$ and $R^{12}$, taken together with the nitrogen atom to which they are bonded form: (i) a 3-8 membered saturated or partially saturated ring having no heteroatom other than the nitrogen atom to which $R^{11}$ and $R^{12}$ are bonded, wherein said 3-8 membered saturated or partially saturated ring includes, but is not limited to, azetidinyl, pyrrolidynyl, or piperidynyl, optionally and independently substituted with 1-4 groups selected from $R^5$ or $R^{5a}$ at one or more substitutable carbon atoms; (ii) a 5-8 membered saturated or partially saturated ring having 1-3 heteroatoms, in addition to the nitrogen atom to which $R^{11}$ and $R^{12}$ are bonded, wherein said 1-3 heteroatoms are independently selected from nitrogen, oxygen, sulfur, sulfone or sulfoxide, and wherein said 5-8 membered saturated or partially saturated ring having 1-3 heteroatoms includes, but is not limited to, morpholino, thiomorpholino, piperazinyl or homopiperazinyl optionally and independently substituted with 1-4 groups selected from $R^5$ or $R^{5a}$ at one or more substitutable carbon atoms and at one or more substitutable nitrogen atoms with $R^6$ or $R^{6a}$; (iii) a 9-10 membered saturated or partially saturated bicyclic ring having no heteroatom other than the nitrogen atom to which $R^{11}$ and $R^{12}$ are bonded, wherein said 9-10 membered saturated or partially saturated bicyclic ring having no heteroatom is optionally substituted with 1-4 groups independently selected from $R^5$ or $R^{5a}$ at one or more substitutable carbon atoms; (iv) a 9-10 membered saturated or partially saturated bicyclic ring having 1-5 heteroatoms, in addition to the nitrogen atom to which $R^{11}$ and $R^{12}$ are bonded, wherein said heteroatoms are independently selected from nitrogen, oxygen, sulfur, sulfoxide, sulfone, carboxamide or sulfoxamide; or (v) a 6-14 membered saturated or partially saturated bridged ring having 1-3 heteroatoms in addition to the nitrogen atom to which $R^{11}$ and $R^{12}$ are bonded, wherein said 1-3 heteroatoms are independently selected from nitrogen, oxygen, sulfur, sulfone, or sulfoxide, and wherein said 6-14 membered saturated or partially saturated bridged ring having 1-3 heteroatoms is optionally and independently substituted with 1-4 groups selected from $R^5$ or $R^{5a}$ at one or more substitutable carbon atoms and at one or more substitutable nitrogen atoms with $R^6$ or $R^{6a}$.

$R^4$ is selected from $(CH_2)_nOH$, $(CH_2)_nNR^{11}R^{12}$, $C(O)NHR^7$, $C(O)NR^{11}R^{12}$, $C(O)OR^7$, $C(O)R^7$, $C(O)NR^7R^7$, $C(O)NR^7R^8$, $(CH_2)_nNR^7R^7$, $(CH_2)_nNR^7R^8$, $(CH_2)_nCN$, $(CH_2)_nSR^7$, $(CH_2)_nS(O)_nR^7$, or $(CH_2)_nS(O)_nNR^7R^7$. Each n is independently 1 or 2.

When $R^4$ is $C(O)OR^7$, $R^7$ of $C(O)OR^7$ is H, $C_1$-$C_{10}$alkyl, $C_2$-$C_{10}$ alkenyl, $C_3$-$C_{10}$alkynyl, $C_3$-$C_{12}$cycloalkyl, $C_5$-$C_{12}$cycloalkenyl, aryl, haloalkyl or heterocyclyl. The $C_1$-$C_{10}$alkyl, $C_2$-$C_{10}$ alkenyl, $C_3$-$C_{10}$alkynyl, $C_3$-$C_{12}$cycloalkyl, $C_5$-$C_{12}$cycloalkenyl, aryl, haloalkyl, or heterocyclyl is optionally and independently substituted with 1-4 groups selected from halo, aryl, cycloalkyl, heterocyclyl, alkyl, $R^9$ or $R^{10}$. When $R^4$ is $C(O)OR^7$, $R^7$ is preferably methyl, ethyl or propyl optionally and independently substituted with one or more groups selected from halo, hydroxy, amino, $C_1$-$C_6$ alkyl, $C_1$-$C_6$ alkoxy, $C_1$-$C_6$ alkylamino, or $diC_1$-$C_6$ alkylamino.

When $R^4$ is $C(O)R^7$, $R^7$ of $C(O)R^7$ is independently H, $C_1$-$C_{10}$ alkyl, $C_2$-$C_{10}$ alkenyl, $C_3$-$C_{10}$ alkynyl, $C_3$-$C_{12}$ cycloalkyl, $C_5$-$C_{12}$ cycloalkenyl, aryl, haloalkyl or heterocyclyl. The group represented by $R^7$ is optionally and independently substituted with 1-3 groups selected from halo, aryl, cycloalkyl, heterocyclyl, alkyl, $R^9$ or $R^{10}$. For example, $R^7$ can be selected from H or $C_1$-$C_{10}$ alkyl and the $R^7$ group can be optionally and independently substituted with 1-4 groups selected from halo, hydroxy, amino, $C_1$-$C_6$ alkyl, $C_1$-$C_6$ alkoxy, $C_1$-$C_6$ alkylamino or di$C_1$-$C_6$ alkylamino.

When $R^4$ is C(O)NHR$^7$, $R^7$ of C(O)NHR$^7$ is selected from H, $C_1$-$C_{10}$alkyl, $C_2$-$C_{10}$alkenyl, $C_3$-$C_{10}$alkynyl, $C_3$-$C_{12}$cycloalkyl, $C_5$-$C_{12}$cycloalkenyl, aryl, haloalkyl, heteroaryl, or heterocyclyl. The $C_1$-$C_{10}$ alkyl, $C_2$-$C_{10}$ alkenyl, $C_3$-$C_{10}$ alkynyl, $C_3$-$C_{12}$ cycloalkyl, $C_5$-$C_{12}$ cycloalkenyl, aryl, haloalkyl, heteroaryl or heterocyclyl is optionally and independently substituted with 1-4 groups selected from halo, aryl, cycloalkyl, heterocyclyl, alkyl, $R^9$ or $R^{10}$. In one embodiment, $R^7$ is phenyl and the phenyl can be optionally and independently substituted with 1, 2, or 3 groups selected from methyl, ethyl, methoxy, $CF_3$, OC(O)R$^7$, $CH_2OH$, $CH_2CH_2OH$, $NH_2$, NR$^7$R$^7$, NHC(O)NHR$^7$, NHSO$_2$R$^7$, C(O)OR$^7$, C(O)NHR$^7$, or SO$_2$CH$_3$. $R^7$ can be $C_1$-$C_{10}$ alkyl and the $C_1$-$C_{10}$ alkyl group is optionally and independently substituted with 1-3 groups selected from amino, halo, hydroxy, phenyl, $C_1$-$C_6$ alkyl, $C_1$-$C_6$ alkoxy, $C_1$-$C_6$ alkylamino, or di$C_1$-$C_6$ alkylamino.

When $R^4$ is C(O)NR$^{11}$R$^{12}$, $R^{11}$ and $R^{12}$, taken together with the nitrogen atom to which they are bonded form: (i) a 3-8 membered saturated or partially saturated ring having no heteroatom other than the nitrogen atom to which $R^{11}$ and $R^{12}$ are bonded, wherein said 3-8 membered saturated or partially saturated ring is optionally and independently substituted with 1-4 groups selected from $R^5$ or $R^{5a}$ at one or more substitutable carbon atoms; (ii) a 5-8 membered saturated or partially saturated ring having 1-3 heteroatoms, in addition to the nitrogen atom to which $R^{11}$ and $R^{12}$ are bonded, wherein said 1-3 heteroatoms are independently selected from nitrogen, oxygen, sulfur, sulfone or sulfoxide, and wherein said 5-8 membered saturated or partially saturated ring having 1-3 heteroatoms is optionally and independently substituted with 1-4 groups selected from $R^5$ or $R^{5a}$ at one or more substitutable carbon atoms and at one or more substitutable nitrogen atoms with $R^6$ or $R^{6a}$; (iii) a 9-10 membered saturated or partially saturated bicyclic ring having no heteroatom other than the nitrogen atom to which $R^{11}$ and $R^{12}$ are bonded, wherein said 9-10 membered ring saturated or partially saturated bicyclic ring having no heteroatom is optionally substituted with 1-4 groups independently selected from $R^5$ or $R^{5a}$ at one or more substitutable carbon atoms; or (iv) a 9-10 membered saturated or partially saturated bicyclic ring having 1-5 heteroatoms, in addition to the nitrogen atom to which $R^{11}$ and $R^{12}$ are bonded, wherein said heteroatoms are independently selected from nitrogen, oxygen, sulfur, sulfoxide, sulfone, carboxamide or sulfoxamide.

When $R^4$ is C(O)NR$^{11}$R$^{12}$, $R^{11}$ and $R^{12}$, taken together with the nitrogen atom to which they are bonded form a 3-8 membered saturated or partially saturated ring having no heteroatom other than the nitrogen atom to which $R^{11}$ and $R^{12}$ are bonded. The 3-8 membered saturated or partially saturated ring having no heteroatom other than the bound nitrogen atom is optionally and independently substituted with 1-4 groups selected from $R^5$ or $R^{5a}$ at one or more substitutable carbon atoms. For example, the 3-8 membered saturated or partially saturated ring with no heteroatom other than the bound nitrogen atom can be azetidinyl, pyrrolidynyl, or piperidynyl optionally and independently substituted with 1-4 groups selected from hydroxy, $CH_2OH$, $CH_2CH_2OH$, $NH_2$, NHR$^7$, NHCOR$^7$, NHC(O)NHR$^7$, or NR$^7$R$^7$ at substitutable carbon atoms.

When $R^4$ is C(O)NR$^{11}$R$^{12}$, $R^{11}$ and $R^{12}$, taken together with the nitrogen atom to which they are bonded can form a 5-8 membered saturated or partially saturated ring having 1-3 heteroatoms, in addition to the nitrogen atom to which $R^{11}$ and $R^{12}$ are bonded. The 1-3 heteroatoms of the 5-8 membered saturated or partially saturated ring are independently selected from nitrogen, oxygen, sulfur, sulfone, or sulfoxide. The 5-8 membered saturated or partially saturated ring having 1-3 heteroatoms can be optionally and independently substituted with 1-4 groups selected from $R^5$ or $R^{5a}$ at one or more substitutable carbon atoms. The heteroatoms can be one or more nitrogen atoms and the one or more nitrogen atoms can be optionally and independently substituted with 1-4 groups of $R^6$ or $R^{6a}$.

When $R^4$ is C(O)NR$^{11}$R$^{12}$, $R^{11}$ and $R^{12}$, taken together with the nitrogen atom to which they are bonded can form a 9-10 membered saturated or partially saturated bicyclic ring having no heteroatom other than the nitrogen atom to which $R^{11}$ and $R^{12}$ are bonded. The 9-10 membered saturated or partially saturated bicyclic ring having no heteroatom other than the bound nitrogen atom is optionally substituted with 1-4 groups independently selected from $R^5$ or $R^{5a}$ at one or more substitutable carbon atoms. The 9-10 membered saturated or partially saturated bicyclic ring having no heteroatom other than the bound nitrogen atom can have an aryl group within the bicyclic ring.

When $R^4$ is C(O)NR$^{11}$R$^{12}$, $R^{11}$ and $R^{12}$, taken together with the nitrogen atom to which they are bonded can form a 9-10 membered saturated or partially saturated bicyclic ring having 1-5 heteroatoms, in addition to the nitrogen atom to which and $R^{12}$ are bonded. The 1-5 heteroatoms are independently selected from nitrogen, oxygen, sulfur, sulfoxide, sulfone, carboxamide or sulfoxamide. The 9-10 membered saturated or partially saturated bicyclic ring having 1-5 heteroatoms can be optionally and independently substituted with 1-4 groups selected from $R^5$ or $R^{5a}$ at one or more substitutable carbon atoms. The 1-5 heteroatoms can be one or more nitrogen atoms and the one or more nitrogen atoms can be optionally and independently substituted with 1-4 groups of $R^6$ or $R^{6a}$. The 9-10 membered saturated or partially saturated bicyclic ring having 1-5 heteroatoms can contain an aryl group within the bicyclic group.

When $R^4$ is $(CH_2)_n$NR$^7$R$^7$, $R^7$ of $(CH_2)_n$NR$^7$R$^7$ is independently selected from H, $C_1$-$C_{10}$alkyl, $C_2$-$C_{10}$alkenyl, $C_3$-$C_{10}$alkynyl, $C_3$-$C_{12}$cycloalkyl, $C_5$-$C_{12}$ cycloalkenyl, aryl, haloalkyl, heteroaryl, or heterocyclyl. $C_1$-$C_{10}$alkyl, $C_2$-$C_{10}$alkenyl, $C_3$-$C_{10}$alkynyl, $C_3$-$C_{12}$cycloalkyl, $C_5$-$C_{12}$ cycloalkenyl, aryl, haloalkyl, heteroaryl, or heterocyclyl is optionally and independently substituted with 1-4 groups selected from halo, aryl, cycloalkyl, heterocyclyl, alkyl, $R^9$, or $R^{10}$. For example, $R^7$ can be independently H or $C_1$-$C_{10}$alkyl and $R^7$ is optionally and independently substituted with 1-4 groups selected from hydroxy, amino, aryl, alkyl or halo. In one embodiment, the $C_1$-$C_{10}$ alkyl is optionally substituted with phenyl. The phenyl can be optionally and independently substituted with one or more alkyl, halo, amino, hydroxy, alkoxy, or CF3.

When $R^4$ is $(CH_2)_n$NR$^{11}$R$^{12}$, $R^{11}$ and $R^{12}$, taken together with the nitrogen atom to which they are bonded form: (i) a 3-8 membered saturated or partially saturated ring having no heteroatom other than the nitrogen atom to which $R^{11}$ and $R^{12}$ are bonded, wherein said 3-8 membered saturated or partially saturated ring is optionally and independently substituted with 1-4 groups selected from $R^5$ or $R^{5a}$ at one or more substitutable carbon atoms; (ii) a 5-8 membered saturated or partially saturated ring having 1-3 heteroatoms, in addition to the nitrogen atom to which $R^{11}$ and $R^{12}$ are bonded, wherein said 1-3 heteroatoms are independently selected from nitrogen, oxygen, sulfur, sulfone or sulfoxide, and wherein said 5-8 membered saturated or partially saturated ring having 1-3 heteroatoms is optionally and independently substituted with 1-4 groups selected from $R^5$ or $R^{5a}$ at one or more substitutable carbon atoms and at one or more substitutable nitrogen atoms with $R^6$ or $R^{6a}$; (iii) a 9-10 membered saturated or partially saturated bicyclic ring having no heteroatom other than the nitrogen atom to which $R^{11}$ and $R^{12}$ are bonded, wherein said 9-10 membered saturated or partially saturated bicyclic ring having no heteroatom is optionally substituted with 1-4 groups independently selected from $R^5$ or $R^{5a}$ at one or more substitutable carbon atoms; (iv) a 9-10 membered saturated or partially saturated bicyclic ring having 1-5 heteroatoms, in addition to the nitrogen atom to which $R^{11}$ and $R^{12}$ are bonded, wherein said heteroatoms are independently selected from nitrogen, oxygen, sulfur, sulfoxide, sulfone, carboxamide or sulfoxamide; or (v) a 6-14 membered saturated or partially saturated bridged ring having 1-3 heteroatoms in addition to the nitrogen atom to which $R^{11}$ and $R^{12}$ are bonded, wherein said 1-3 heteroatoms are independently selected from nitrogen, oxygen, sulfur, sulfone, or sulfoxide, and wherein said 6-14 membered saturated or partially saturated bridged ring having 1-3 heteroatoms is optionally and independently substituted with 1-4 groups selected from $R^5$ or $R^{5a}$ at one or more substitutable carbon atoms and at one or more substitutable nitrogen atoms with $R^6$ or $R^{6a}$.

In one embodiment, $R^4$ is $(CH_2)_nNR^{11}R^{12}$ and $R^{11}$ and $R^{12}$, taken together with the nitrogen atom to which they are bonded form a 3-8 membered saturated or partially saturated ring having no heteroatom other than the nitrogen atom to which $R^{11}$ and $R^{12}$ are bonded. The 3-8 membered saturated or partially saturated ring having no heteroatom other than the bound nitrogen atom is optionally and independently substituted with 1-4 groups selected from $R^5$ or $R^{5a}$ at one or more substitutable carbon atoms. The 3-8 membered saturated or partially saturated ring having no heteroatom other than the bound nitrogen can be a 4, 5 or 6 membered saturated ring optionally substituted at one or more substitutable carbon atoms. Preferably, the 3-8 membered ring is azetidinyl, pyrrolidinyl, or piperidinyl optionally and independently substituted with 1-2 groups selected from hydroxy, halo, $OC(O)R^7$, $CH_2OH$, $CH_2CH_2OH$, $NH_2$, $NR^7R^7$, $NHC(O)NHR^7$, $NHSO_2R^7$, $C(O)OR^7$, or $C(O)NHR^7$ at one or more substitutable carbon atoms.

In one embodiment, $R^4$ is $(CH_2)_nNR^{11}R^{12}$ and $R^{11}$ and $R^{12}$, taken together with the nitrogen atom to which they are bonded form a 5-8 membered saturated or partially saturated ring having 1-3 heteroatoms, in addition to the nitrogen atom to which $R^{11}$ and $R^{12}$ are bonded. The 1-3 heteroatoms are independently selected from nitrogen, oxygen, sulfur, sulfone, or sulfoxide, and the 5-8 membered saturated or partially saturated ring having 1-3 heteroatoms is optionally and independently substituted with 1-4 groups selected from $R^5$ or $R^{5a}$ at one or more substitutable carbon atoms and at one or more substitutable nitrogen atoms with $R^6$ or $R^{6a}$. For example, the 5-8 membered saturated or partially saturated ring having 1-3 heteroatoms is a 6 or 7 membered saturated ring having 1 heteroatom. The heteroatom can be nitrogen optionally substituted with $C_1$-$C_{10}$alkyl, hydroxyl$C_2$-$C_{10}$alkyl, or $C(O)NHR^7$. Alternatively, the heteroatom can be oxygen. In one embodiment, the oxygen, together with $R^{11}$, $R^{12}$ and with the nitrogen atom to which they are bonded, can form morpholino. Accordingly, the 5-8 membered saturated or partially saturated ring having 1-3 heteroatoms can be morpholino, thiomorpholino, piperazinyl, or homopiperazinyl. The piperazinyl or homopiperazinyl is optionally and independently substituted with one or more groups selected from hydroxy, $C_1$-$C_{10}$ alkyl, $CH_2CH_2OH$, $C(O)R^7$, $C(O)NHR^7$, $SO_2R^7$, $SO_2NHR^7$, or $C(O)OR^7$ at a nitrogen atom.

In one embodiment, $R^4$ is $(CH_2)_nNR^{11}R^{12}$ and $R^{11}$ and $R^{12}$, taken together with the nitrogen atom to which they are bonded can form a 9-10 membered saturated or partially saturated bicyclic ring having no heteroatom other than the nitrogen atom to which $R^{11}$ and $R^{12}$ are bonded. The 9-10 membered saturated or partially saturated bicyclic ring having no heteroatom other than the bound nitrogen atom is tetrahydroisoquinoline optionally substituted with 1-4 groups independently selected from $R^5$ or $R^{5a}$ at one or more substitutable carbon atoms. The bicyclic ring can also contain an aryl group within the ring.

In one embodiment, $R_4$ is $(CH_2)_nNR^{11}R^{12}$ and $R^{11}$ and $R^{12}$, taken together with the nitrogen atom to which they are bonded can form a 9-10 membered saturated or partially saturated bicyclic ring having 1-5 heteroatoms, in addition to the nitrogen atom to which $R^{11}$ and $R^{12}$ are bonded. The 1-5 heteroatoms are independently selected from nitrogen, oxygen, sulfur, sulfoxide, sulfone, carboxamide, or sulfoxamide. The 9-10 membered saturated or partially saturated bicyclic ring having 1-5 heteroatoms can be optionally and independently substituted with 1-4 groups selected from $R^5$ or $R^{5a}$ at one or more substitutable carbon atoms and at one or more substitutable nitrogen atoms with $R^6$ or $R^{6a}$. The bicyclic ring can also contain an aryl group within the ring.

In one embodiment, $R^4$ is $(CH_2)_nNR^{11}R^{12}$ and $R^{11}$ and $R^{12}$, taken together with the nitrogen atom to which they are bonded can form a 6-14 membered saturated or partially saturated bridged ring having 1-3 heteroatoms in addition to the nitrogen atom to which $R^{11}$ and $R^{12}$ are bonded, wherein said 1-3 heteroatoms are independently selected from nitrogen, oxygen, sulfur, sulfone, or sulfoxide, and wherein said 6-14 membered saturated or partially saturated bridged ring having 1-3 heteroatoms is optionally and independently substituted with 1-4 groups selected from $R^5$ or $R^{5a}$ at one or more substitutable carbon atoms and at one or more substitutable nitrogen atoms with $R^6$ or $R^{6a}$.

The term "alkyl," used alone or as part of a larger moiety such as "arylalkyl" or "cycloalkyl" refers to a straight or branched hydrocarbon radical having from 1 to 15 carbon atoms (unless stated otherwise) and includes, for example, methyl, ethyl, n-propyl, isopropyl, n-butyl, sec-butyl, isobutyl, tert-butyl, n-pentyl, iso-pentyl, n-hexyl and the like. An alkyl can be unsubstituted or substituted with one or more suitable substituents.

The term "cycloalkyl" refers to a monocyclic or polycyclic hydrocarbon ring group and includes, for example, cyclopropyl, cycloheptyl, cyclooctyl, cyclodecyl, cyclobutyl, adamantyl, norpinanyl, decalinyl, norbornyl, cyclohexyl, cyclopentyl, and the like. A cycloalkyl group can be unsubstituted or substituted with one or more suitable substituents.

The term "hetero" refers to the replacement of at least one carbon atom member in a ring system with at least one heteroatom such as N, S, and O.

The term "heterocycloalkyl" means a non-aromatic monocyclic or polycyclic ring comprising carbon and hydrogen atoms and at least one heteroatom, preferably, 1 to 4 heteroatoms selected from N, O, S, sulfone, or sulfoxide. A heterocycloalkyl group can have one or more carbon-carbon double bonds or carbon-heteroatom double bonds in the ring group as long as the ring group is not rendered aromatic by their presence. Examples of heterocycloalkyl groups include azetidinyl, aziridinyl, pyrrolidinyl, piperidinyl, piperazinyl, homopiperazinyl, morpholino, thiomorpholino, tetrahydrofuranyl, tetrahydrothiofuranyl, tetrahydropyranyl, pyranyl, and the like. A heterocycloalkyl group can be unsubstituted or substituted with one or more suitable substituents.

As used herein, the term "halo" includes fluoro, chloro, bromo, and iodo.

As used herein, the term "alkenyl" refers to straight and branched hydrocarbon radicals having from 2 to 6 carbon atoms and one double bond and includes ethenyl, 3-buten-1-yl, 2-ethenylbutyl, 3-hexen-1-yl, and the like. An alkenyl can be unsubstituted or substituted with one or more suitable substituents.

As used herein, the term "alkynyl" refers to straight and branched hydrocarbon radicals having from 2 to 6 carbon atoms and one triple bond and includes ethynyl, 3-butyn-1-yl, propynyl, 2-butyn-1-yl, 3-pentyn-1-yl, and the like. An alkynyl can be unsubstituted or substituted with one or more suitable substituents.

As used herein, the term "alkoxy" refers to the alkyl groups above bound through oxygen, examples of which include methoxy, ethoxy, isopropoxy, tert-butoxy, and the like. In addition, alkoxy also refers to polyethers such as —O—$(CH_2)_2$—O—$CH_3$, and the like. An alkoxy can be unsubstituted or substituted with one or more suitable substituents.

As used herein, the term "aryl" refers to unsubstituted or substituted aromatic monocyclic or polycyclic groups and includes, for example, phenyl and naphthyl. The term "aryl" also includes a phenyl ring fused to a non-aromatic carbocyclic or heterocyclic ring. The term "aryl" may be interchangeably used with "aryl ring," "aromatic group," and "aromatic ring." Heteroaryl groups have 4 to 14 atoms, 1 to 9 of which are independently selected from the group consisting of O, S and N. Heteroaryl groups have 1-3 heteroatoms in a 5-8 membered aromatic group. An aryl or heteroaryl can be a mono- or bicyclic aromatic group. Typical aryl and heteroaryl groups include, for example, phenyl, quinolinyl, indazoyl, indolyl, dihydrobenzodioxynyl, 3-chlorophenyl, 2,6-dibromophenyl, pyridyl, pyrimidinyl, 3-methylpyridyl, benzothienyl, 2,4,6-tribromophenyl, 4-ethylbenzothienyl, furanyl, 3,4-diethylfuranyl, naphthyl, 4,7-dichloronaphthyl, pyrrole, pyrazole, imidazole, thiazole, and the like. An aryl or heteroaryl can be unsubstituted or substituted with one or more suitable substituents.

As used herein, the term "haloalkyl" refers to any alkyl radical having one or more hydrogen atoms replaced by a halogen atom. Examples of haloalkyl include —$CF_3$, —$CFH_2$, —$CF_2H$, and the like.

As used herein, the term "arylalkyl" refers to any alkyl radical having one or more hydrogen atoms replaced by an aryl group. Examples of arylalkyl include benzyl ($C_6H_5CH_2$—) and the like.

As used herein, the term "hydroxyl" or "hydroxy" refers to —OH.

As used herein, the term "amino" refers to —$NH_2$.

As used herein, the term "hydroxyalkyl" refers to any hydroxyl derivative of alkyl radical. The term "hydroxyalkyl" includes any alkyl radical having one or more hydrogen atoms replaced by a —OH group.

As used herein, the term "kinase panel" refers to a list of kinases, including but not limited to, ABL1(E255K)-phosphorylated, ABL1(T315I)-phosphorylated, ABL1-phosphorylated, ACVR1B, ADCK3, AKT1, AKT2, ALK, AURKA, AURKB, AXL, BMPR2, BRAF, BRAF(V600E), BTK, CDK11, CDK2, CDK3, CDK7, CDK9, CHEK1, CSF1R, CSNK1D, CSNK1G2, DCAMKL1, DYRK1B, EGFR, EGFR(L858R), EPHA2, ERBB2, ERBB4, ERK1, FAK, FGFR2, FGFR3, FLT1, FLT3, FLT4, GSK3B, IGF1R, IKK-α, IKK-β, INSR, JAK2(JH1domain-catalytic), JAK3 (JH1domain-catalytic), JNK1, JNK2, INK3, KIT, KIT (D816V), KIT(V559D,T670I), LKB1, LRRK2, LRRK2 (G2019S), MAP3K4, MAPKAPK2, MARK3, MEK1, MEK2, MET, MKNK1, MKNK2, MLK1, MTOR, p38-alpha, p38-beta, PAK1, PAK2, PAK-4, PCTK1, PDGFRA, PDGFRB, PDPK1, PIK3C2B, PIK3CA, PIK3CG, PIM1, PIM2, PIM3, PKAC-alpha, PLK1, PLK3, PLK4, PRKCE, PYK2, RAF1, RET, RIOK2, ROCK2, RSK2, SNARK, SRC, SRPK3, SYK, TAK1, TGFBR1, TIE2, TRKA, TSSK1B, TYK2(JH1domain-catalytic), ULK2, VEGFR2, YANK3 and ZAP70. Kinase assay panels containing the kinases described herein are commercially available for biochemically profiling kinase inhibitors for their selectivity.

As used herein, the term "dermatological disorder" refers to a skin disorder. Such dermatological disorders include, but are not limited to, proliferative or inflammatory disorders of the skin such as, atopic dermatitis, bullous disorders, collagenoses, contact dermatitis eczema, Kawasaki Disease, rosacea, Sjogren-Larsso Syndrome, and urticaria.

As used herein, the term "neurogenerative disease" or "nervous system disorder" refers to conditions that alter the structure or function of the brain, spinal cord or peripheral nervous system, including but not limited to Alzheimer's disease, cerebral edema, cerebral ischemia, multiple sclerosis, neuropathies, Parkinson's disease, those found after blunt or surgical trauma (including post-surgical cognitive dysfunction and spinal cord or brain stem injury), as well as the neurological aspects of disorders such as degenerative disk disease and sciatica. The acronym "CNS" refers to the central nervous system (brain and spinal cord).

As used herein, the term "respiratory disease" refers to diseases affecting the organs that are involved in breathing, such as the nose, throat, larynx, trachea, bronchi, and lungs. Respiratory diseases include, but are not limited to, asthma, adult respiratory distress syndrome and allergic (extrinsic) asthma, non-allergic (intrinsic) asthma, acute severe asthma, chronic asthma, clinical asthma, nocturnal asthma, allergen-induced asthma, aspirin-sensitive asthma, exercise-induced asthma, isocapnic hyperventilation, child-onset asthma, adult-onset asthma, cough-variant asthma, occupational asthma, steroid-resistant asthma, seasonal asthma, seasonal allergic rhinitis, perennial allergic rhinitis, chronic obstructive pulmonary disease, including chronic bronchitis or emphysema, pulmonary hypertension, interstitial lung fibrosis and/or airway inflammation and cystic fibrosis, and hypoxia.

As used herein, the term "cancer" refers to an abnormal growth of cells which tend to proliferate in an uncontrolled way and, in some cases, to metastasize. The types of cancer include, but is not limited to, solid tumors, such as those of the bladder, bowel, brain, breast, endometrium, heart, kidney, lung, lymphatic tissue (lymphoma), ovary, pancreas or other endocrine organ (thyroid), prostate, skin (melanoma) or hematological tumors (such as the leukemias).

As used herein, the term "inflammatory disorders" refers to those diseases or conditions that are characterized by one or more of the signs of pain (dolor, from the generation of noxious substances and the stimulation of nerves), heat (calor, from vasodilatation), redness (rubor, from vasodilatation and increased blood flow), swelling (tumor, from excessive inflow or restricted outflow of fluid), and loss of function, which may be partial or complete, temporary or permanent. Inflammation takes many forms and includes, but is not limited to, inflammation that is one or more of the following, acute, adhesive, atrophic, catarrhal, chronic, cirrhotic, diffuse, disseminated, exudative, fibrinous, fibrosing, focal, granulomatous, hyperplastic, hypertrophic, interstitial, metastatic, necrotic, obliterative, parenchymatous, plastic, productive, proliferous, pseudomembranous, purulent, sclerosing, seroplastic, serous, simple, specific, subacute, suppurative, toxic, traumatic, and/or ulcerative. Inflammatory disorders further include, without being limited to those affecting the blood vessels (polyarteritis, temporarl arteritis); joints (arthritis: crystalline, osteo-, psoriatic, reactive, rheumatoid, Reiter's); gastrointestinal tract; skin (dermatitis); or multiple organs and tissues (systemic lupus erythematosus).

As used herein, the term "cardiovascular disease" refers to diseases affecting the heart or blood vessels or both, including but not limited to atherosclerosis, arrhythmia, angina, myocardial ischemia, myocardial infarction, cardiac or vascular aneurysm, vasculitis, stroke, peripheral obstructive arteriopathy of a limb, an organ, or a tissue, reperfusion injury following ischemia of an organ or a tissue, endotoxic, surgical, or traumatic shock, hypertension, valvular heart disease, heart failure, abnormal blood pressure, vasoconstriction, vascular abnormality, or inflammation.

As used herein, the term "bone disease" means a disease or condition of the bone, including, but not limited to, inappropriate bone remodeling, loss or gain, osteopenia, osteomalacia, osteofibrosis, osteoporosis and Paget's disease.

As used herein, the term "inhibitor" refers to a compound which inhibits one or more kinases described herein. For example, the term "SYK inhibitor" refers to a compound which inhibits the SYK receptor or reduces its signaling effect.

As used herein, the term "pharmaceutically acceptable" refers a material, such as a carrier or diluent, which does not abrogate the biological activity or properties of the compounds described herein. Such materials are administered to an individual without causing undesirable biological effects or interacting in a deleterious manner with any of the components of the composition in which it is contained.

As used herein, the term "pharmaceutically acceptable salt" refers to a formulation of a compound that does not cause significant irritation to an organism to which it is administered and does not abrogate the biological activity and properties of the compounds described herein.

As used herein, the term "pharmaceutical composition" refers to a mixture of a compound described herein with other chemical components, such as carriers, stabilizers, diluents, dispersing agents, suspending agents, thickening agents, and/or excipients.

As used herein, the term "prodrug" refers to an agent that is converted into the parent drug in vivo.

As used herein, the term "protein kinase-mediated disease" or a "disorder or disease or condition mediated by inappropriate protein kinase activity" refers to any disease state mediated or modulated by protein kinases described herein. Such disease states include, but are not limited to, asthma, chronic obstructive pulmonary disease (COPD), adult respiratory distress syndrome (ARDS), ulcerative colitis, Crohn's disease, bronchitis, dermatitis, allergic rhinitis, psoriasis, scleroderma, urticaria, bullous disorders, collagenoses, contact dermatitis eczema, Kawasaki Disease, rosacea, Sjogren-Larsso Syndrome, rheumatoid arthritis, multiple sclerosis, inflammatory bowel syndrome, HIV, lupus, lymphoma, osteosarcoma, melanoma, breast cancer, renal cancer, prostate cancer, colorectal cancer, thyroid cancer, ovarian cancer, pancreatic cancer, neuronal cancer, lung cancer, uterine cancer, gastrointestinal cancer, Alzheimer's disease, Parkinson's disease, osteoporosis, osteopenia, osteomalacia, osteofibrosis, Paget's disease, diabetes, blood vessel proliferative disorders, ocular diseases, cardiovascular disease, restenosis, fibrosis, atherosclerosis, arrhythmia, angina, myocardial ischemia, myocardial infarction, cardiac or vascular aneurysm, vasculitis, stroke, peripheral obstructive arteriopathy, reperfusion injury following ischemia of an organ or a tissue, endotoxic, surgical or traumatic shock, hypertension, valvular heart disease, heart failure, abnormal blood pressure, vasoconstriction, vascular abnormality, transplant rejection and infectious diseases including viral and fungal infections.

As used herein, the term "kinase-mediated disease" or "kinase-mediated disease" or a "disorder or disease or condition mediated by inappropriate kinase activity" refers to any disease state mediated or modulated by a kinase mechanism. For example "SYK-mediated disease" refers to any diase state mediated or modulated by SYK mechanisms. Such SYK-mediated disease states include, but are not limited to, inflammatory, respiratory diseases and autoimmune diseases, such as, by way of example only, asthma, chronic obstructive pulmonary disease (COPD), adult respiratory distress syndrome (ARDs), ulcerative colitis, Crohn's disease, bronchitis, dermatitis, allergic rhinitis, psoriasis, scleroderma, urticaria, rheumatoid arthritis, multiple sclerosis, cancer, HIV associated disease and lupus.

As used herein, the term "PYK2-mediated disease" or a "disorder or disease or condition mediated by inappropriate PYK2 activity" refers to any disease state mediated or modulated by PYK2 kinase mechanisms. Such disease states include, but are not limited to, osteoporesis, arthritis, myeloid leukemia, hypo-osmolality, sarcoma, blast crisis, glioma, erythroleukemia and cancer.

As used herein, the term "ZAP70-mediated disease" or a "disorder or disease or condition mediated by inappropriate ZAP70 activity" refers to any disease state mediated or modulated by ZAP70 kinase mechanisms. Such disease states include, but are not limited to, immunodeficiency diseases characterized by a selective absence of CD8-positive T-cells.

As used herein, the term "FAK-mediated disease" or a "disorder or disease or condition mediated by inappropriate FAK activity" refers to any disease state mediated or modulated by FAK kinase mechanisms. Such disease states include, but are not limited to, cancer, macular degeneration or a condition associated with aberrantly increased levels of angiogenesis.

As used herein, the term "PIM1-mediated disease" or a "disorder or disease or condition mediated by inappropriate PIM1 activity" refers to any disease state mediated or modulated by PIM1 kinase mechanisms. Such disease states include, but are not limited to, cancer, myeloproliferative diseases, autoimmune diseases, allergic reactions and in organ transplantation rejection syndromes.

As used herein, the term "FLT3-mediated disease" or a "disorder or disease or condition mediated by inappropriate FLT3 activity" refers to any disease state mediated or modulated by FLT3 kinase mechanisms. Such disease states include, but are not limited to, leukemia including acute myelogenous leukemia or a condition associated with aberrantly increased levels of FLT3 kinase.

As used herein, the term "RET-mediated disease" or a "disorder or disease or condition mediated by inappropriate RET activity" refers to any disease state mediated or modulated by RET kinase mechanisms. Such disease states include, but are not limited to, thyroid cancer, a condition associated with aberrantly increased levels of RET kinase.

As used herein, the term "JAK2-mediated disease" or a "disorder or disease or condition mediated by inappropriate JAK2 activity" refers to any disease state mediated or modulated by JAK2 kinase mechanisms. Such disease states include, but are not limited to, polycythemia vera, essential thrombocythemia, other myeloproliferative disorders cancer, or a condition associated with aberrantly increased levels of JAK2 kinase.

As used herein, the term "LRRK2-mediated disease" or a "disorder or disease or condition mediated by inappropriate LRRK2 activity" refers to any disease state mediated or modulated by LRRK2 kinase mechanisms. Such disease states include, but are not limited to, Parkinson's disease, other neurodegenerative disease or a condition associated with aberrantly increased levels of angiogenesis.

As used herein, the term "therapeutically effective amount" refers to any amount of a compound which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

As used herein, the term "treat," "treating" or "treatment" refers to methods of alleviating, abating or ameliorating a disease or condition symptoms, preventing additional symptoms, ameliorating or preventing the underlying metabolic causes of symptoms, inhibiting the disease or condition, arresting the development of the disease or condition, relieving the disease or condition, causing regression of the disease or condition, relieving a condition caused by the disease or condition, or stopping the symptoms of the disease or condition either prophylactically and/or therapeutically.

As used herein, the term "solvate" refers to a complex of variable stoichiometry formed by a solute (in this invention, a compound of Formula (I) or a pharmaceutically acceptable salt thereof) and a solvent. Such solvents for the purpose of the invention may not interfere with the biological activity of the solute. Non-limiting examples of suitable solvents include water, acetone, methanol, ethanol and acetic acid. Preferably the solvent used is a pharmaceutically acceptable solvent. Non-limiting examples of suitable pharmaceutically acceptable solvents include water, ethanol and acetic acid.

As used herein, the term "subject" or "patient" encompasses mammals and non-mammals. Examples of mammals include, but are not limited to, humans, chimpanzees, apes monkeys, cattle, horses, sheep, goats, swine; rabbits, dogs, cats, rats, mice, guinea pigs, and the like. Examples of non-mammals include, but are not limited to, birds, fish and the like.

As used herein, the term "administration" or "administering" of the subject compound refers to providing a compound of the invention to a subject in need of treatment.

As used herein, the term "carrier" refers to chemical compounds or agents that facilitate the incorporation of a compound described herein into cells or tissues.

As used herein, the term "acceptable" with respect to a formulation, composition or ingredient, as used herein, means having no persistent detrimental effect on the general health of the subject being treated.

As used herein, the term "diluent" refers to chemical compounds that are used to dilute a compound described herein prior to delivery. Diluents can also be used to stabilize compounds described herein.

As used herein, the term "effective amount" or "therapeutically effective amount" refer to a sufficient amount of a compound described herein being administered which will relieve to some extent one or more of the symptoms of the disease or condition being treated.

I. Human Protein Kinases

Protein kinases play a central role in the regulation of a wide variety of cellular processes and maintaining control over cellular function. Protein kinases catalyze and regulate the process of phosphorylation, whereby the kinases covalently attach phosphate groups to proteins or lipid targets in response to a variety of extracellular signals. Examples of such stimuli include hormones, neurotransmitters, growth and differentiation factors, cell cycle events, environmental stresses and nutritional stresses. An extracellular stimulus may affect one or more cellular responses related to cell growth, migration, differentiation, secretion of hormones, activation of transcription factors, muscle contraction, glucose metabolism, control of protein synthesis, and regulation of the cell cycle.

The compounds of the present invention were screened against the kinase panel and inhibited the activity of at least one kinase on the panel. Examples of kinases include, but are not limited to SYK, PYK2, FAK, ZAP70, PIM1, FLT3, RET, JAK2, JAK3, LRRK2, LRRK2(G2019S), ABL1(T315I), AURKB, AXL, FLT3, KIT, KIT(D816V), KIT(V559D, T670I), MKNK2, MLK1, PDGFRB, PLK3, RET, SNARK, SRPK3, TAK1, or TYK2 kinases and mutant forms thereof. As such, the compounds and compositions of the invention are useful for treating diseases or disorders in which such kinases contribute to the pathology and/or symptomology of a disease or disorder associated with such kinases. Such diseases or disorders include, but are not limited to, pancreatic cancer, papillary thyroid carcinoma, ovarian carcinoma, human adenoid cystic carcinoma, non small cell lung cancer, secretory breast carcinoma, congenital fibrosarcoma, congenital mesoblastic nephroma, acute myelogenous leukemia, psoriasis, metastasis, cancer-related pain and neuroblastoma, autoimmune diseases, inflammatory diseases, bone diseases, metabolic diseases, neurological and neurodegenerative diseases, cancer, cardiovascular diseases, respiratory diseases, allergies and asthma, Alzheimer's disease, and hormone related diseases, benign and malignant proliferative disorders, diseases resulting from inappropriate activation of the immune system and diseases resulting from inappropriate activation of the nervous systems, allograft rejection, graft vs. host disease, diabetic retinopathy, choroidal neovascularization due to age-related macular degeneration, psoriasis, arthritis, osteoarthritis, rheumatoid arthritis, synovial pannus invasion in arthritis, multiple sclerosis, myasthenia gravis, diabetes mellitus, diabetic angiopathy, retinopathy of prematurity, infantile hemangiomas, non-small cell lung, bladder and head and neck cancers, prostate cancer, breast cancer, ovarian cancer, gastric and pancreatic cancer, psoriasis, fibrosis, atherosclerosis, restenosis, autoimmune disease, allergy, respiratory diseases, asthma, transplantation rejection, inflammation, thrombosis, retinal vessel proliferation, inflammatory bowel disease, Crohn's disease, ulcerative colitis, bone diseases, transplant or bone marrow transplant rejection, lupus, chronic pancreatitis, cachexia, septic shock, fibroproliferative and differentiative skin diseases or disorders, central nervous system diseases, neurodegenerative diseases, Alzheimer's disease, Parkinson's disease, disorders or conditions related to nerve damage and axon degeneration subsequent to a brain or spinal cord injury, acute or chronic cancer, ocular diseases, viral infections, heart disease, lung or pulmonary diseases or kidney or renal diseases and bronchitis.

The compounds described herein are inhibitors of kinase activity and have therapeutic benefit in the treatment of disorders associated with inappropriate kinase activity, in particular in the treatment and prevention of disease states mediated by kinase. Therefore, the present invention provides methods of regulating, and in particular inhibiting, signal transduction cascades in which a kinase plays a role. The method generally involves administering to a subject or contacting a cell expressing the kinase with an effective amount of a compound described herein, prodrug, or an acceptable salt, hydrate, solvate, N-oxide and/or composition thereof, to regulate or inhibit the signal transduction cascade. The methods are also used to regulate, and in particular inhibit, downstream processes or cellular responses elicited by activation of the particular kinase signal transduction cascade. The methods are also practiced in in vitro contexts or in in vivo contexts as a therapeutic approach towards the treatment or prevention of diseases characterized by, caused by or associated with activation of the kinase-dependent signal transduction cascade.

2. Pharmaceutical Composition

For the therapeutic uses of compounds provided herein, including compounds of Formula (I), or pharmaceutically acceptable salts, solvates, N-oxides, prodrugs and isomers thereof, such compounds are administered in therapeutically effective amounts either alone or as part of a pharmaceutical composition. Accordingly, provided herein are pharmaceutical compositions, which comprise at least one compound provided herein, including at least one compound of Formula (I), pharmaceutically acceptable salts and/or solvates thereof, and one or more pharmaceutically acceptable carriers, diluents, adjuvant or excipients. In addition, such compounds and compositions are administered singly or in combination with one or more additional therapeutic agents. The methods of administration of such compounds and compositions include, but are not limited to, intravenous administration, inhalation, oral administration, rectal administration, parenteral, intravitreal administration, subcutaneous administration, intramuscular administration, intranasal administration, dermal administration, topical administration, ophthalmic administration, buccal administration, tracheal administration, bronchial administration, sublingual administration or otic administration. Compounds provided herein are administered by way of known pharmaceutical formulations, including tablets, capsules or elixirs for oral administration, suppositories for rectal administration, sterile solutions or suspensions for parenteral or intramuscular administration, lotions, gels, ointments or creams for topical administration, and the like.

The therapeutically effective amount will vary depending on, among others, the disease indicated, the severity of the disease, the age and relative health of the subject, the potency of the compound administered, the mode of administration and the treatment desired. The required dosage will also vary depending on the mode of administration, the particular condition to be treated and the effect desired.

Pharmaceutically acceptable salt forms include pharmaceutically acceptable acidic/anionic or basic/cationic salts. Pharmaceutically acceptable acidic/anionic salts include, acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, malonate, mandelate, mesylate, methylsulfate, mucate, napsylate, nitrate, pamoate, pantothenate, phosphate/diphospate, polygalacturonate, salicylate, stearate, subacetate, succinate, sulfate, hydrogensulfate, tannate, tartrate, teoclate, tosylate, and triethiodide salts. Pharmaceutically acceptable basic/cationic salts include, the sodium, potassium, calcium, magnesium, diethanolamine, N-methyl-D-glucamine, L-lysine, L-arginine, ammonium, ethanolamine, piperazine and triethanolamine salts.

A pharmaceutically acceptable acid addition salt is formed by reaction of the free base form a compound of Formula (I) with a suitable inorganic or organic acid including, but not limited to, hydrobromic, hydrochloric, sulfuric, nitric, phosphoric, succinic, maleic, formic, acetic, propionic, fumaric, citric, tartaric, lactic, benzoic, salicylic, glutamic, aspartic, p-toluenesulfonic, benzenesulfonic, methanesulfonic, ethanesulfonic, naphthalenesulfonic such as 2-naphthalenesulfonic, or hexanoic acid. A pharmaceutically acceptable acid addition salt of a compound of formula (I) can comprise or be, for example, a hydrobromide, hydrochloride, sulfate, nitrate, phosphate, succinate, maleate, formarate, acetate, propionate, fumarate, citrate, tartrate, lactate, benzoate, salicylate, glutamate, aspartate, p-toluenesulfonate, benzenesulfonate, methanesulfonate, ethanesulfonate, naphthalenesulfonate (e.g. 2-naphthalenesulfonate) or hexanoate salt.

The free acid or free base forms of the compounds of the invention may be prepared from the corresponding base addition salt or acid addition salt from, respectively. For example a compound of the invention in an acid addition salt form may be converted to the corresponding free base by treating with a suitable base (e.g., ammonium hydroxide solution, sodium hydroxide, and the like). A compound of the invention in a base addition salt form may be converted to the corresponding free acid by treating with a suitable acid (e.g., hydrochloric acid, etc.).

Prodrug of the compounds of the invention can be prepared by methods known to one of ordinary skill in the art (e.g., see Saulnier et al., (1994), Bioorganic and Medicinal Chemistry Letters, Vol. 4, p. 1985; the entire teachings of which are incorporated herein by reference).

Protected derivatives of the compounds of the invention can be made by means known to one of ordinary skill in the art. (e.g., see T. W. Greene, "Protecting Groups in Organic Chemistry," $3^{rd}$ edition, John Wiley and Sons, Inc., 1999, the entire teachings of which are incorporated herein by reference).

Compounds of the invention can be prepared as their individual stereoisomers by reacting a racemic mixture of the compound with an optically active resolving agent to form a pair of diastereoisomeric compounds, separating the diastereomers and recovering the optically pure enantiomers. (see, Jean Jacques, Andre Collet, Samuel H. Wilen, "Enantiomers, Racemates and Resolutions," John Wiley And Sons, Inc., 1981, the entire teachings of which are incorporated herein by reference)

Compounds of Formula (I) are made by processes described herein and in the Examples. In certain embodiments, compounds of Formula (I) are made by (a) optionally converting a compound of the invention into a pharmaceutically acceptable salt; (c) optionally converting a salt form of a compound of the invention to a non-salt form; (d) optionally converting an unoxidized form of a compound of the invention into a pharmaceutically acceptable N-oxide; (e) optionally resolving an individual isomer of a compound of the invention from a mixture of isomers; (f) optionally converting a non-derivatized compound of the invention into a pharmaceutically acceptable prodrug derivative; and (g) optionally converting a prodrug derivative of a compound of the invention to its non-derivatized form.

The teachings of all patents, published applications and references cited herein are incorporated by reference in their entirety.

EXAMPLES

The present invention is further exemplified by the following examples that illustrate the preparation of compounds of Formula (I) according to the invention. The examples are for illustrative purpose only and are not intended, nor should they be construed as limiting the invention in any manner. Those skilled in the art will appreciate that variations and modifications can be made without changing the scope of the invention.
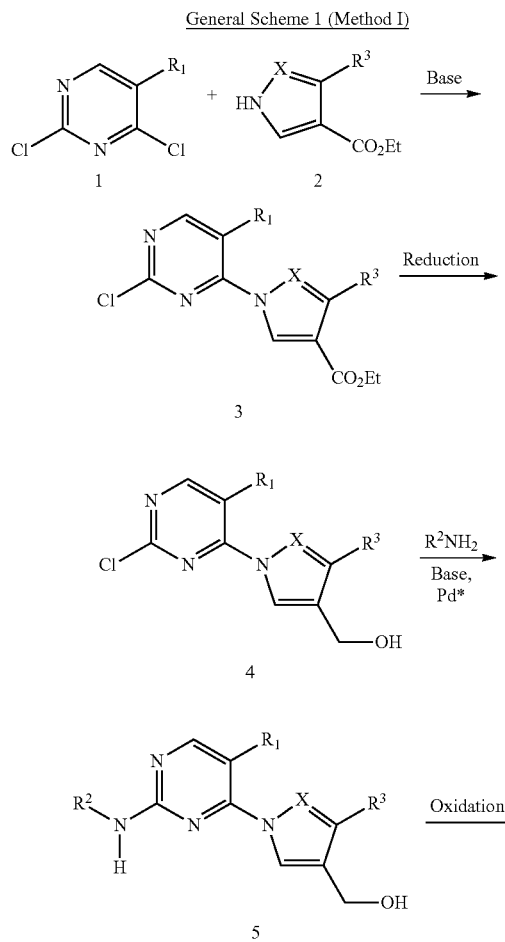
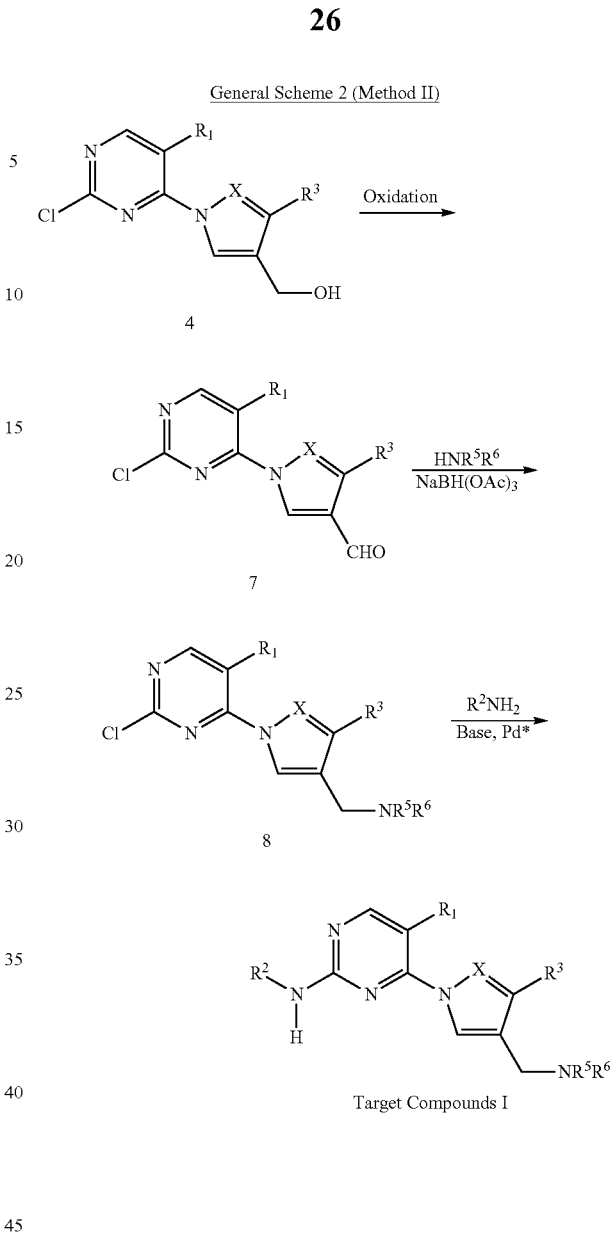
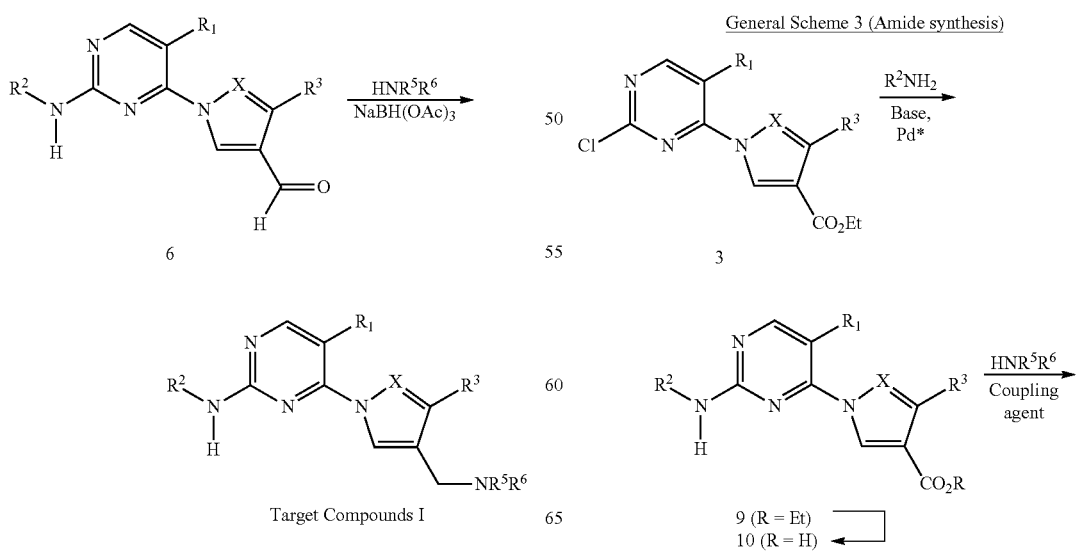

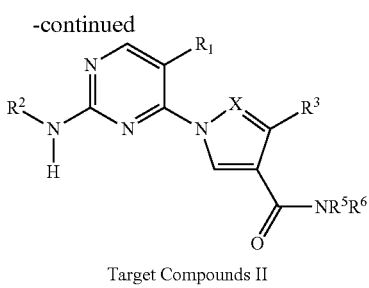

Target Compounds II

General Scheme 4 (Intermediate 5 and 9)

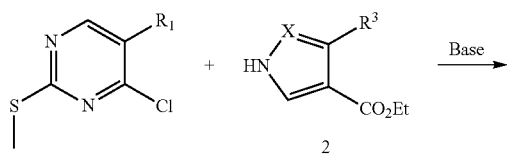

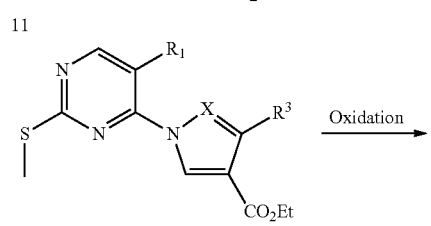

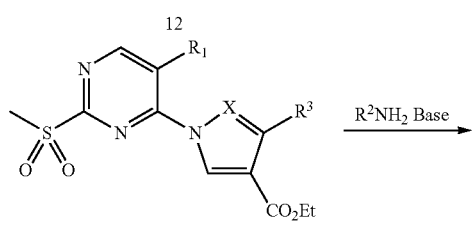

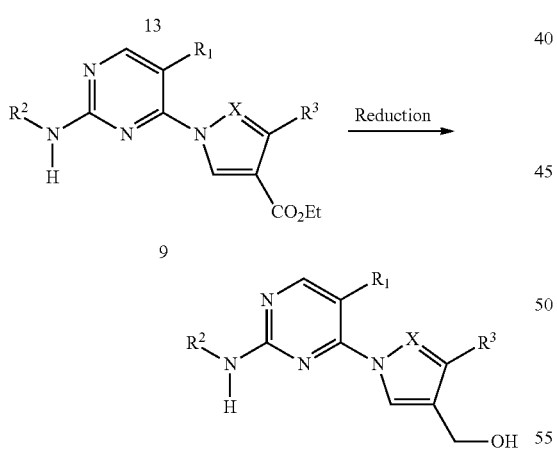

It is to be understood that these examples are for illustrative purpose only and are not to be construed as limiting this invention in any manner.

Nuclear magnetic resonance (NMR) and mass spectrometry (MS) spectra obtained for compounds described in the examples below and those described herein were consistent with that of the compounds of formulae herein.

Liquid Chromatography-Mass Spectrometry (LC-MS) Method:

1. Samples are run on Agilent Technologies 6120 MSD system with a Zorbax Eclipse XDB-C18 (3.5µ) reverse phase column (4.6×50 mm) run at room temperature with flow rate of 1.5 mL/minute.
2. The mobile phase use solvent A (water/0.1% formic acid) and solvent B (acetonitrile/0.1% formic acid).
3. The mass spectra (m/z) were recorded using electrospray ionization (ESI).

Proton NMR Spectra:

Unless otherwise indicated, all $^1$H NMR spectra are run on a Varian series Mercury 300 MHz. All observed protons are reported as parts-per-million (ppm) downfield from tetramethylsilane using conventional abbreviations for designation of major peaks: e.g. s (singlet), d (doublet), t (triplet), q (quartet), m (multiplet) and br (broad).

Preparation of ethyl 1-(2-chloro-5-fluoropyrimidin-4-yl)-3-methyl-1H-pyrazole-4-carboxylate; Intermediate 1

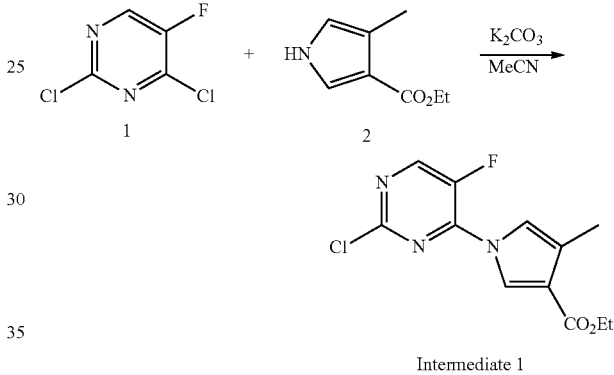

To a solution of ethyl 3-methyl-1H-pyrazole-4-carboxylate 2 (3.15 g, 20.5 mmol) in anhydrous acetonitrile were added potassium carbonate (5.7 g, 41 mmol) and 2,4-dichloro-5-fluoropyrimidine 1 at room temperature. The resulting suspension was heated at 80° C. for 3 hours with monitoring a reaction with LC-MS or thin layer chromatography (TLC). It was diluted with ethyl acetate and washed with brine. The collected organic layer was dried over anhydrous sodium sulfate and then partially concentrated in vacou. To this, n-hexanes were added to form pale yellow precipitates. The resulting solids were collected by filtration and rinsed with n-hexanes and then dried with high vacuum to give 4.9 g (85%) of the target intermediate 1; MS (ESI) m/z 285 [M+H]$^+$.

Preparation of (1-(2-chloro-5-fluoropyrimidin-4-yl)-3-methyl-1H-pyrazol-4-yl)methanol; Intermediate No. 2

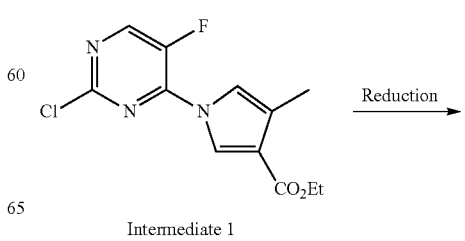

Intermediate 1

-continued

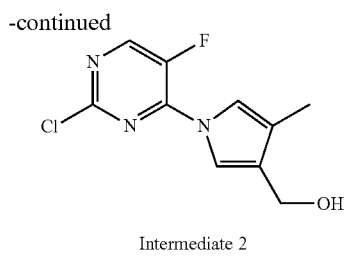

Intermediate 2

To a solution of ethyl 1-(2-chloro-5-fluoropyrimidin-4-yl)-3-methyl-1H-pyrazole-4-carboxylate 1 (4.9 g, 17.2 mmol) in 60 mL of anhydrous tetrahydrofuran (THF), was slowly added 38 mL (38 mmol) of 1M solution of di-isobutylaluminum hydride (DIBAL) in toluene with ice bath cooling. After being stirred for 2 hours at the same temperature, the reaction was quenched by slow addition of 1N-NaOH solution. It was diluted with ethyl acetate and washed with brine. The collected organic layer was dried over anhydrous sodium sulfate and then partially concentrated in vacou. To this, n-hexanes were added to form pale yellow precipitates. The resulting solids were collected by filtration and rinsed with n-hexanes and then dried with high vacuum to give 3.7 g (90%) of Intermediate No. 2; $^1$H NMR (300 MHz, CDCl$_3$) δ 8.57 (1H, d, J=3.3 Hz), 8.52 (1H, s), 7.94 (1H, s), 4.72 (2H, s); MS (ESI) m/z 243 [M+H]$^+$.

Preparation of methyl 1-(5-methyl-2-(3,4,5-tri-methoxyphenylamino)pyrimidin-4-yl)-1H-pyrrole-3-carboxylate: Compound 1

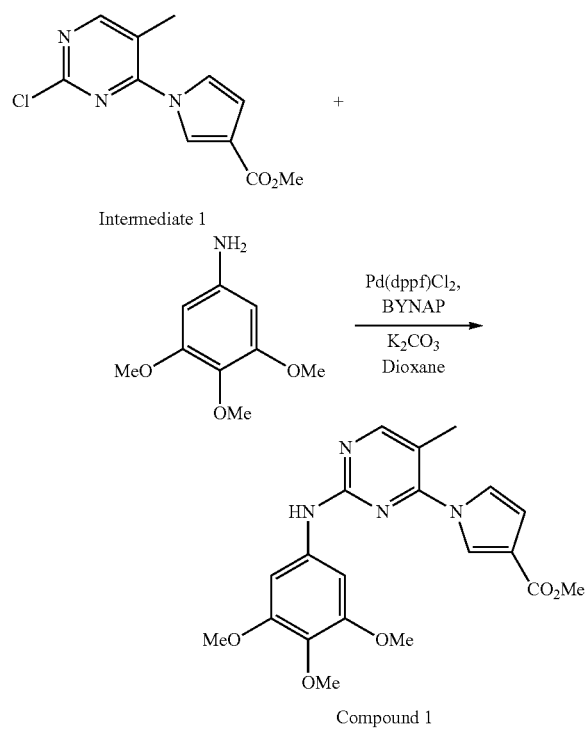

A two dram vial was charged with methyl 1-(2-chloro-5-methylpyrimidin-4-yl)-1H-pyrrole-3-carboxylate (Intermediate No. 1) (300 mg, 1.20 mmol), 3,4,5-trimethoxylaniline (240 mg, 1.32 mmol), 540 mg (3.9 mmol) of potassium carbonate, Pd(dppf)Cl$_2$ (50 mg), (±)-2,2'-bis(diphenylphosphino)-1,1'-binaphthyl (BYNAP) (70 mg) and 4 mL of anhydrous dioxane. After being degassed by nitrogen bubbling, the reaction mixture was heated at 100° C. for 4 hours. The resulting insolubles were removed by filtration. The filtrate was concentrated in vacuo and then purified by silica gel chromatography to afford Compound No. 1 as a white solid (291 mg, 61%); MS (ESI) m/z 399 [M+H]$^+$.

Preparation of ethyl 1-(2-(3,5-dimethylphenylamino)pyrimidin-4-yl)-3-methyl-1H-pyrazole-4-carboxylate: Compound 2

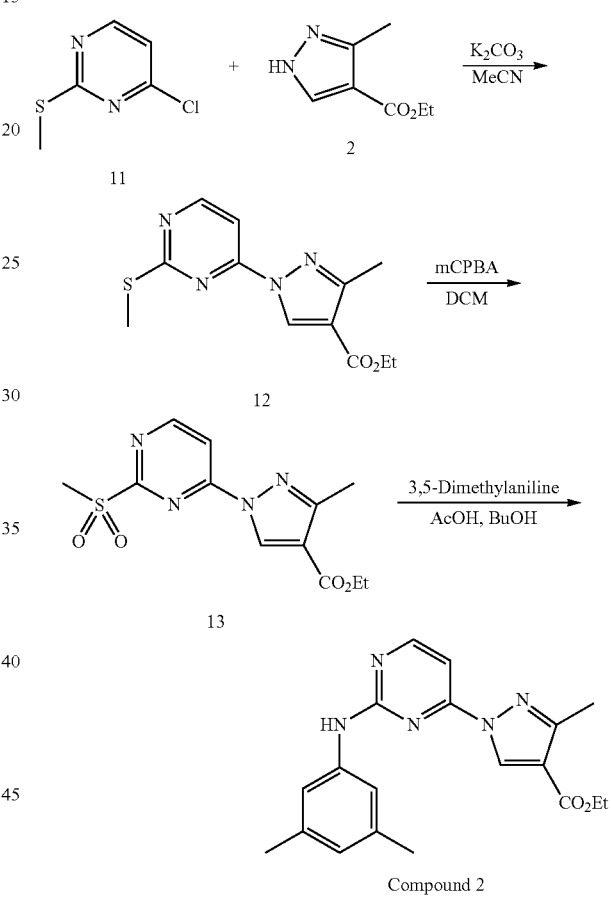

Compound 2

To a solution of ethyl 3-methyl-1H-pyrazole-4-carboxylate 2 (5.0 g, 32 4 mmol) in anhydrous acetonitrile (60 mL) were added potassium carbonate (8.96 g, 64.9 mmol) and 4-chloro-2-(methylthio)pyrimidine 11 (5.47 g, 34.1 mmol) at room temperature (rt). The resulting suspension was heated at 80° C. for 8 hours with monitoring a reaction with LC-MS or thin layer chromatography (TLC). It was diluted with ethyl acetate and washed with brine. The collected organic layer was dried over anhydrous sodium sulfate and then concentrated in vacou. The resulting residue was recrystallized with methanol to give 7.88 g (83%) of ethyl 3-methyl-1-(2-(methylthio)pyrimidin-4-yl)-1H-pyrazole-4-carboxylate 12; MS (ESI) m/z 279 [M+H]$^+$. The resulting pyrazole-4-carboxylate 12 (7.44 g, 26 7 mmol) was dissolved in 30 mL of DCM and then cooled to 0° C. To this was added 3-chloroperbenzoic acid (mCPBA, 13.2 g, 58.8 mmol) at the same temperature. The reaction was warmed to room temperature, stirred for 2 hours and then quenched by addition of saturated NaHCO₃ solution. The collected organic layer was dried over anhydrous sodium sulfate and then concentrated in vacou. The resulting residue was recrystallized with iso-propylether to give 7.88 g (83%) of ethyl 3-methyl-1-(2-(methylsulfonyl) pyrimidin-4-yl)-1H-pyrazole-4-carboxylate 13 as a colorless solid (6.92 g, 83%); m/z 311 [M+H]⁺. The obtained sulfoxide 13 (3.0 g, 9.7 mmol) was mixed with acetic acid (0.42 mL, 9.7 mmol) and 3,5-dimethylaniline (1.4 mL, 9.7 mmol) in 10 mL of n-butanol. After being heated at reflux for 2 hours, the mixture was concentrated in vacou. The resulting residue was extracted with DCM, washed with a saturated NaHCO₃ solution. The collected organic layer was dried over anhydrous sodium sulfate, concentrated in vacou and then recrystallized with ethyl acetate to afford 0.86 g (26%) of Compound No. 2 as a pale yellow solid; m/z 352 [M+H]⁺.

1-(2-(3,5-dimethylphenylamino)pyrimidin-4-yl)-3-methyl-1H-pyrazole-4-carboxylic acid: Compound 3

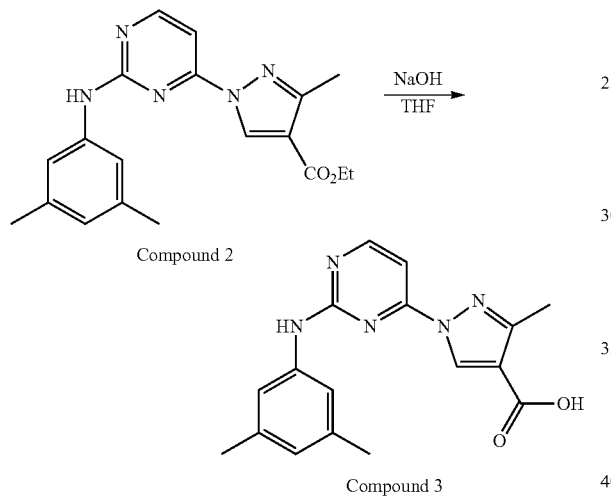

Compound 2

Compound 3

To a solution of Compound No. 2 (0.77 g, 2.2 mmol) in ethanol (10 mL), was added 4 mL of 2N-NaOH solution at room temperature. The reaction mixture was heated at reflux for 2 hours. When no starting material was observed, ethanol was removed in vacuo. The residue was washed with DCM and then the aqueous layer was acidified with 1N-HCl aqueous solution to form pale yellow precepitates. The resulting solids were collected by filtration and then vacuum dried to give Compound No. 3 as a pale yellow solid (0.41 g, 58%); MS (ESI) m/z 324 [M+H]⁺.

Preparation of 1-(2-(3,5-dimethylphenylamino)-5-fluoroprimidin-4-yl)-3-methyl-1H-pyrazole-4-carbaldehyde: Intermediate No. 3

Compound 4

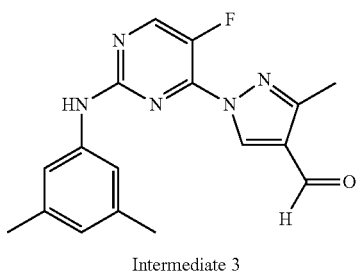

Intermediate 3

To a solution of Compound No. 4 (0.56 g, 1.7 mmol) in 30 mL of dichloroethane (DCE), was added MnO₂ (1.5 g, 10.2 mmol). After being stirred for 4 hours at 60-70° C., the reaction mixture was passed through a pad of Celite and rinsed with dichloromethane. The filtrate was concentrated in vacuo to give desired Intermediate No. 3 as a pale yellow solid (0.44 g, 80%); MS (ESI) m/z 326 [M+H]⁺

Preparation of Amine

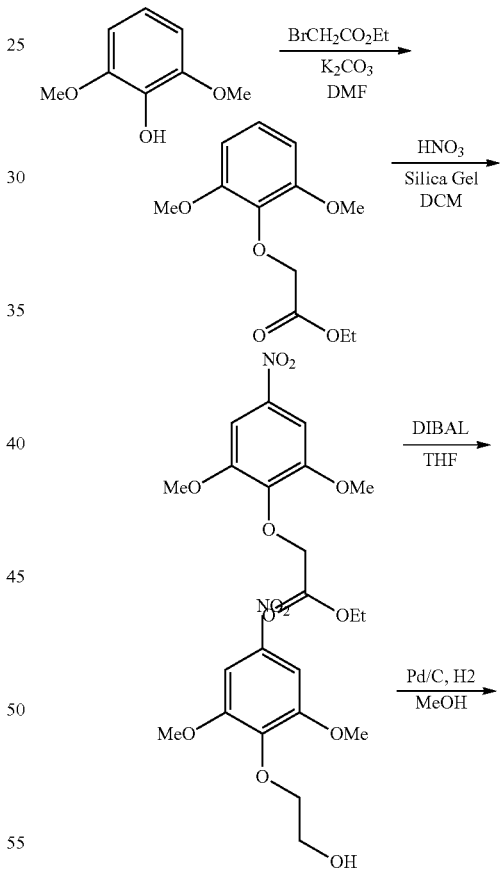

Preparation of 2-(4-Amino-2,6-dimethoxyphenoxy)ethanol

To a solution of 2,6-dimethoxyphenol (1.54 g, 10 mmol) and ethyl bromoacetate (2.00 g, 12 mmol) in 15 mL of anhydrous DMF, was added 2.76 g (20 mmol) of $K_2CO_3$. The reaction mixture was stirred at 30° C. for 20 hours. The mixture was concentrated in vacuo to remove volatiles. The resulting residue was extracted with EtOAc, washed with brine, dried over anhydrous sodium sulfate and then concentrated in vacou to give 2.2 g (91.6%) of ethyl 2-(2,6-dimethoxyphenoxy)acetate. The obtained ester (1.2 g, 5 mmol) was dissolved in a suspension of Silica Gel (2.0 g) in 20 mL of DCM. To this was dropwise added of a solution of concentrated $HNO_3$ (20 mL) in 20 mL of DCM at rt. After being stirred at room temperature for 1 hour, it was transferred into a separatory funnel and then brown bottom layer was discarded into 100 g of ice. The remaining top organic layer was washed with brine, dried over anhydrous sodium sulfate, and then concentrated in vacou to give 1.4 g (98%) of ethyl 2-(2,6-dimethoxy-4-nitrophenoxy)acetate as a brown solid. The obtained nitrophenoxy ester (1.34 g, 4.7 mmol) was dissolved in anhydrous THF (20 mL). To this, was slowly added of 1M DIBAL solution (10.3 mL, 10.3 mmol) in toluene with ice bath cooling. After 1 hour at rt, the reaction was quenched by addition of 1N-NaOH solution, and then extracted with EtOAc. The obtained organic layer was dried over anhydrous sodium sulfate, and passed through Silica Gel pad. The resulting filtrate was concentrated in vacuo to afford 2-(2,6-dimethoxy-4-nitrophenoxy)ethanol (1.01 g, 88%) as a pale yellow solid; MS (ESI) m/z 326 [M+H]+.

Preparation of (1-(2-(3,5-dimethylphenylamino)-5-fluoropyrimidin-4-yl)-3-methyl-1H-pyrazol-4-yl)methanol: Compound No. 4

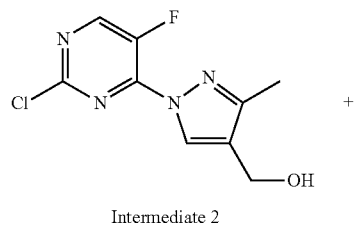

Intermediate 2

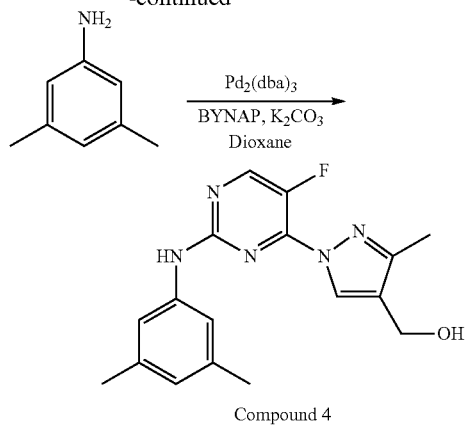

Compound 4

A 40 mL vial was charged with (1-(2-chloro-5-fluoropyrimidin-4-yl)-3-methyl-1H-pyrazol-4-yl)methanol (Intermediate No. 2) (0.50 g, 2.1 mmol), 3,5-dimethylaniline (300 mg, 2.4 mmol), 850 mg (6 2 mmol) of potassium carbonate, $Pd_2(dba)_3$ (86 mg), (±)-2,2'-bis(diphenylphosphino)-1,1'-binaphthyl (BYNAP) (125 mg) and 25 mL of anhydrous dioxane. After being degassed by nitrogen bubbling, the reaction mixture was heated at 100° C. for 6 hours. The resulting insolubles were removed by filtration. The filtrate was concentrated in vacuo and then purified by silica gel chromatography to afford Compound No. 4 as a white solid (0.56 g, 84%); MS (ESI) m/z 328 [M+H]+.

Preparation of Compound Nos. 5 to 28

The following compounds of the general structure shown Table 1 were prepared by a method similar to that described for preparation of Compound No. 4 using the appropriate 2-chloropyrimidine and appropriate amine. Examples of palladium catalysts that may be employed in this reaction include $Pd(OAc)_2$, $Pd_2(dba)_3$, $Pd(dppf)Cl_2$, or $Pd(PPh_3)_4$ and $PdCl_2(PPh_3)_2$. These catalysts are typically employed with suitable ligand, such as BINAP, Xantphos, S-Phos or a related phosphine-based Pd ligand. The reactions were monitored by TLC and LC-MS analysis and were run at 80° C. to 110° C. for 3 to 16 hours.

TABLE 1

Compounds of Formula I

| Compound No. | Structure | Name | Yield (%) | MS (ESI+) m/z |
|---|---|---|---|---|
| 5 | 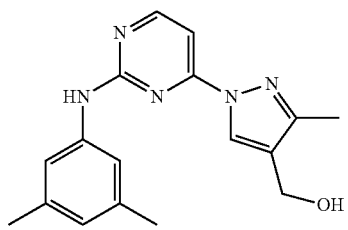 | (1-(2-(3,5-dimethylphenylamino)pyrimidin-4-yl)-3-methyl-1H-pyrazol-4-yl)methanol | 74 | 310 |

TABLE 1-continued

Compounds of Formula I

| Compound No. | Structure | Name | Yield (%) | MS (ESI+) m/z |
|---|---|---|---|---|
| 6 | 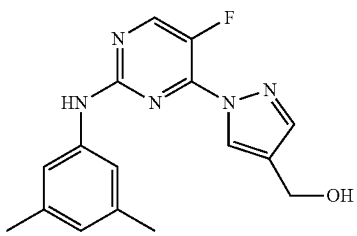 [SMILES: Cc1cc(C)cc(Nc2ncc(F)c(-n3cc(CO)cn3)n2)c1] | (1-(2-(3,5-dimethyl-phenylamino)-5-fluoro-pyrimidin-4-yl)-1H-pyrazol-4-yl)methanol | 80 | 314 |
| 7 | 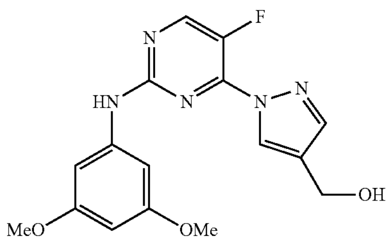 [SMILES: COc1cc(Nc2ncc(F)c(-n3cc(CO)cn3)n2)cc(OC)c1] | (1-(2-(3,5-dimethoxy-phenylamino)-5-fluoro-pyrimidin-4-yl)-1H-pyrazol-4-yl)methanol | 76 | 346 |
| 8 | 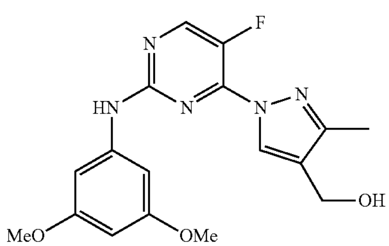 [SMILES: COc1cc(Nc2ncc(F)c(-n3cc(CO)c(C)n3)n2)cc(OC)c1] | (1-(2-(3,5-dimethoxy-phenylamino)-5-fluoro-pyrimidin-4-yl)-3-methyl-1H-pyrazol-4-yl)methanol | 70 | 360 |
| 9 | 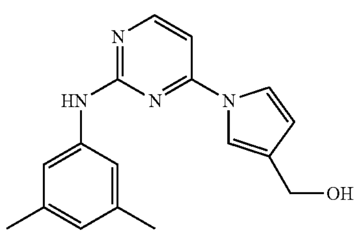 [SMILES: Cc1cc(C)cc(Nc2nccc(-n3ccc(CO)c3)n2)c1] | (1-(2-(3,5-dimethyl-phenylamino)pyrimidin-4-yl)-1H-pyrrol-3-yl)methanol | 88 | 295 |
| 10 | 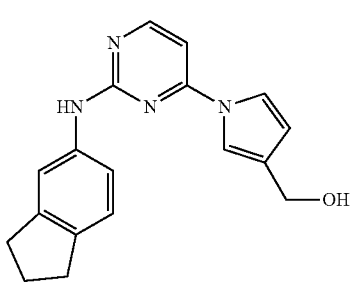 [SMILES: OCc1ccn(-c2ccnc(Nc3ccc4c(c3)CCC4)n2)c1] | (1-(2-(2,3-dihydro-1H-inden-5-ylamino)pyrimidin-4-yl)-1H-pyrrol-3-yl)methanol | 78 | 307 |

TABLE 1-continued

Compounds of Formula I

| Compound No. | Structure | Name | Yield (%) | MS (ESI+) m/z |
|---|---|---|---|---|
| 11 | 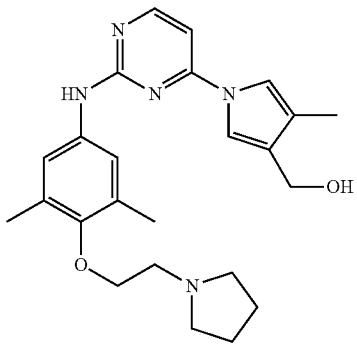 | (1-(2-(3,5-dimethyl-4-(2-(pyrrolidin-1-yl)ethoxy)phenylamino)pyrimidin-4-yl)-4-methyl-1H-pyrrol-3-yl)methanol | 80 | 421 |
| 12 | 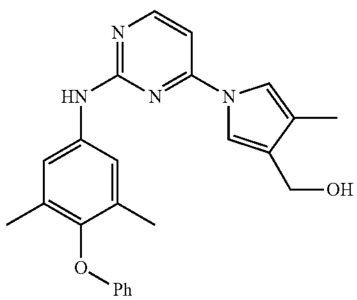 | (1-(2-(3,5-dimethyl-4-phenoxyphenylamino)pyrimidin-4-yl)-4-methyl-1H-pyrrol-3-yl)methanol | 68 | 401 |
| 13 | 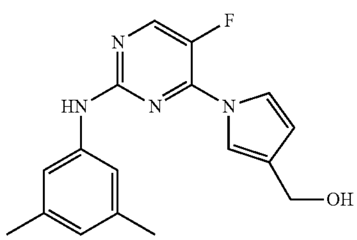 [SMILES: Cc1cc(C)cc(Nc2ncc(F)c(-n3ccc(CO)c3)n2)c1] | (1-(2-(3,5-dimethyl-phenylamino)-5-fluoro-pyrimidin-4-yl)-1H-pyrrol-3-yl)methanol | 90 | 313 |
| 14 | 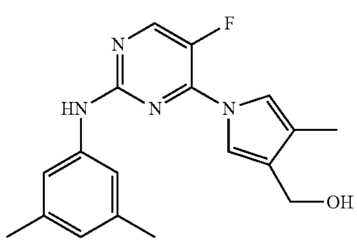 | (1-(2-(3,5-dimethyl-phenylamino)-5-fluoro-pyrimidin-4-yl)-4-methyl-1H-pyrrol-3-yl)methanol | 86 | 327 |
| 15 | 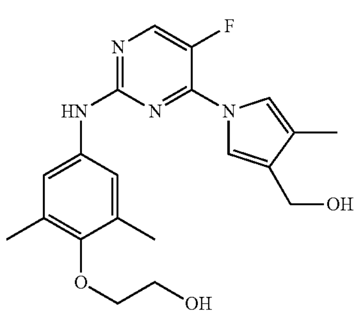 | 2-(4-(5-fluoro-4-(3-(hydroxymethyl)-4-methyl-1H-pyrrol-1-yl)pyrimidin-2-ylamino)-2,6-dimethylphenoxy)ethanol | 65 | 386 |

TABLE 1-continued

Compounds of Formula I

| Compound No. | Structure | Name | Yield (%) | MS (ESI+) m/z |
|---|---|---|---|---|
| 16 | 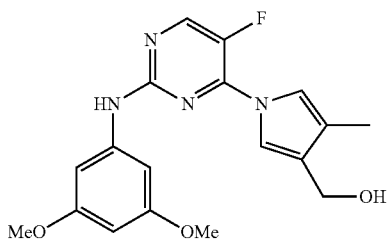 | (1-(2-(3,5-dimethoxy-phenylamino)-5-fluoro-pyrimidin-4-yl)-4-methyl-1H-pyrrol-3-yl)methanol | 81 | 359 |
| 17 | 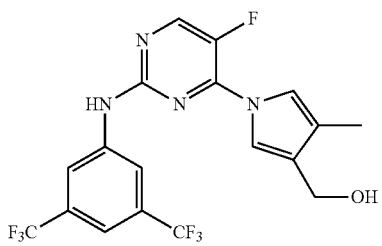 | (1-(2-(3,5-bis(trifluoro-methyl)phenylamino)-5-fluoropyrimidin-4-yl)-4-methyl-1H-pyrrol-3-yl)methanol | 84 | 435 |
| 18 | 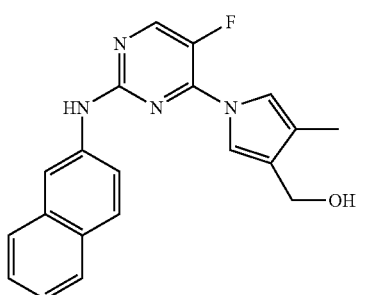 | (1-(5-fluoro-2-(naphthalene-2-ylamino)pyrimidin-4-yl)-4-methyl-1H-pyrrol-3-yl)methanol | 77 | 349 |
| 19 | 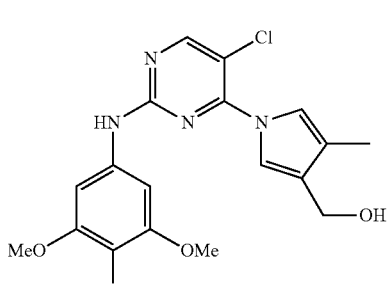 | (1-(5-chloro-2-(3,4,5-trimethoxyphenylamino)pyrimidin-4-yl)-4-methyl-1H-pyrrol-3-yl)methanol | 80 | 404 |
| 20 | 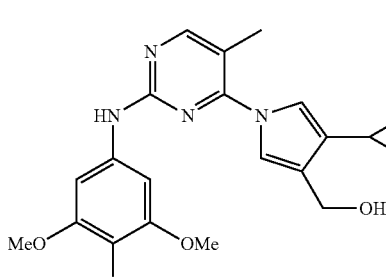 | (4-cyclopropyl-1-(5-methyl-2-(3,4,5-trimethoxyphenylamino)pyrimidin-4-yl)-1H-pyrrol-3-yl)methanol | 76 | 411 |

TABLE 1-continued

Compounds of Formula I

| Compound No. | Structure | Name | Yield (%) | MS (ESI+) m/z |
|---|---|---|---|---|
| 21 | 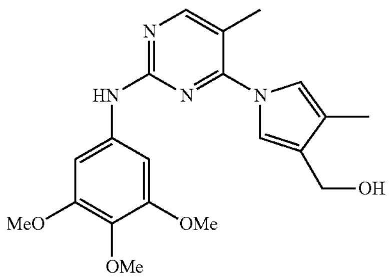 [SMILES: COc1cc(Nc2ncc(C)c(-n3cc(C)c(CO)c3)n2)cc(OC)c1OC] | (4-methyl-1-(5-methyl-2-(3,4,5-trimethoxyphenyl-amino)pyrimidin-4-yl)-1H-pyrrol-3-yl)methanol | 80 | 385 |
| 22 | 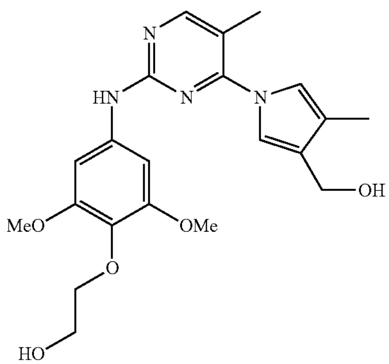 [SMILES: COc1cc(Nc2ncc(C)c(-n3cc(C)c(CO)c3)n2)cc(OC)c1OCCO] | 2-(4-(4-(3-(hydroxyl-methyl)-4-methyl-1H-pyrrol-1-yl)-5-methyl-pyrimidin-2-ylamino)-2,6-dimethoxyphenoxy)ethanol | 63 | 415 |
| 23 | 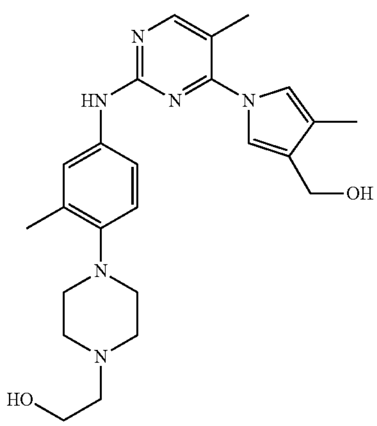 | 2-(4-(4-(4-(3-(hydroxyl-methyl)-4-methyl-1H-pyrrol-1-yl)-5-methyl-pyrimidin-2-ylamino)-2-methylphenyl)piperazin-1-yl)ethanol | 71 | 437 |
| 24 | 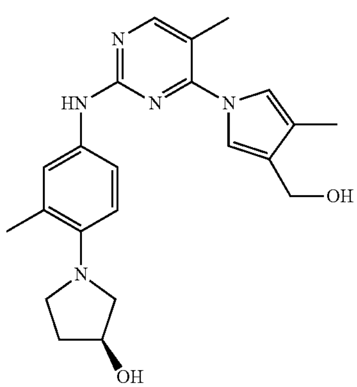 | (S)-1-(4-(4-(3-(hydroxyl-methyl)-4-methyl-1H-pyrrol-1-yl)-5-methyl-pyrimidin-2-ylamino)-2-methylphenyl)pyrrolidin-3-ol | 69 | 394 |

TABLE 1-continued

Compounds of Formula I

| Compound No. | Structure | Name | Yield (%) | MS (ESI+) m/z |
|---|---|---|---|---|
| 25 | 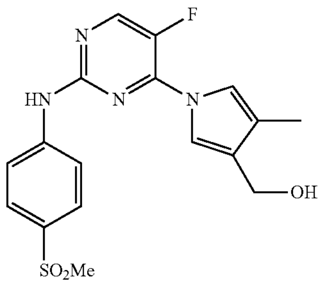 [SMILES: Cc1cn(-c2nc(Nc3ccc(S(C)(=O)=O)cc3)ncc2F)cc1CO] | (1-(5-fluoro-2-(4-(methyl-sulfonyl)phenylamino)pyrimidin-4-yl)-4-methyl-1H-pyrrol-3-yl)methanol | 63 | 377 |
| 26 | 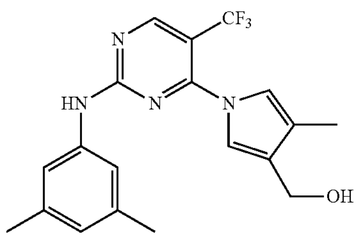 | (1-(2-(3,5-dimethylphenyl-amino)-5-(trifluoro-methyl)pyrimidin-4-yl)-4-methyl-1H-pyrrol-3-yl)methanol | 90 | 377 |
| 27 | 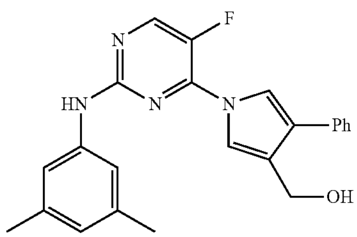 [SMILES: Cc1cc(C)cc(Nc2ncc(F)c(-n3cc(CO)c(-c4ccccc4)c3)n2)c1] | (1-(2-(3,5-dimethylphenyl-amino)-5-fluoropyrimidin-4-yl)-4-phenyl-1H-pyrrol-3-yl)methanol | 84 | 389 |
| 28 | 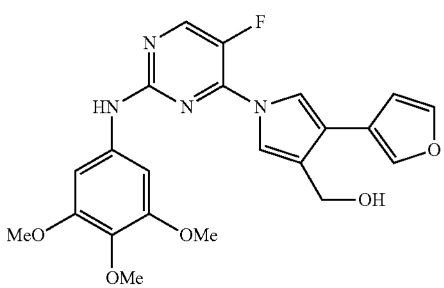 [SMILES: COc1cc(Nc2ncc(F)c(-n3cc(CO)c(-c4ccoc4)c3)n2)cc(OC)c1OC] | (1-(5-fluoro-2-(3,4,5-trimethoxyphenylamino)pyrimidin-4-yl)-4-(furan-3-yl)-1H-pyrrol-3-yl)methanol | 77 | 441 |

1-(2-(3,5-dimethylphenylamino)pyrimidin-4-yl)-N-(2-hydroxyethyl)-N,3-dimethyl-1H-pyrazole-4-carboxamide: Compound No. 29

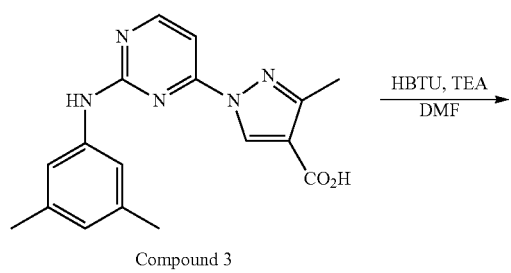

Compound 3

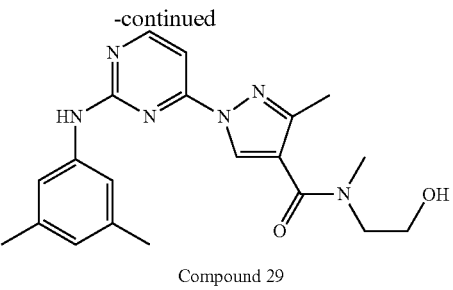

Compound 29

To a solution of an acid Compound No. 3 (65 mg, 0.2 mmol) in 2 mL of anhydrous DMF and DIPEA (100 μL, 0 6 mmol), was added HBTU (83 mg, 0.22 mmol). The mixture was stirred for 15 minute at room temperature. To this was added, 2-(methylamino)ethanol (24 mL, 0 3 mmol) at room temperature. The reaction mixture was stirred at room temperature for 3 hours with monitoring a reaction with TLC. When no starting material was observed, the reaction mixture was diluted with ethyl acetate and washed with 1N-NaOH followed by brine. The collected organic layer was dried over anhydrous sodium sulfate and then concentrated in vacou and then purified by silica gel chromatography to give 53 mg (70%) of target Compound No. 29 as a white solid; $^1$H NMR (400 MHz, DMSO-$d_6$) δ 9.66 (s, 1H), 8.61 (s, 1H), 8.54 (d, J=5.2 Hz, 1H), 7.19 (d, J=5.2 Hz, 1H), 6.65 (s, 1H), 4.82 (br s, 1H), 3.56-3.48 (m, 2H), 3.14-2.95 (m, 2H), 2.31 (s, 3H), 2.26 (s, 6H); MS (ESI) m/z 381 [M+H]$^+$.

Preparation of Compound Nos. 30 to 38

The following compounds of the general structure shown Table 2 were prepared by a method similar to that described for preparation Compound No. 29 using coupling agent such as EDCI, HBTU, HATU, PyBop, or PyBrop. The reactions were monitored by TLC and LC-MS analysis and were run at room temperature 3 to 16 hours.

TABLE 2

Compounds of Formula I

| Compound No. | Structure | NMR (300 Mz, DMSO-$d_6$) or Name | MS (ESI+) m/z |
|---|---|---|---|
| 30 | 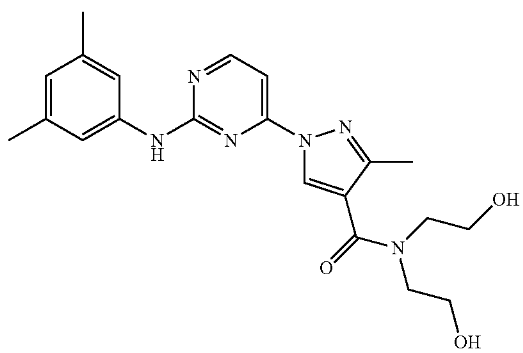 [SMILES: Cc1cc(C)cc(Nc2nccc(-n3cc(C(=O)N(CCO)CCO)c(C)n3)n2)c1] | 1-(2-(3,5-dimethylphenylamino)pyrimidin-4-yl)-N,N-bis(2-hydroxyethyl)-3-methyl-1H-pyrazole-4-carboxamide; 9.64 (s, 1H), 8.60 (s, 1H), 8.53 (d, J = 5.2 Hz, 1H), 7.37 (s, 2H), 7.19 (d, J = 5.6 Hz, 1H), 6.64 (s, 1H), 4.80 (s, 2H), 3.51 (br s, 8H), 2.28 (s, 3H), 2.26 (s, 6H) | 411 |
| 31 | 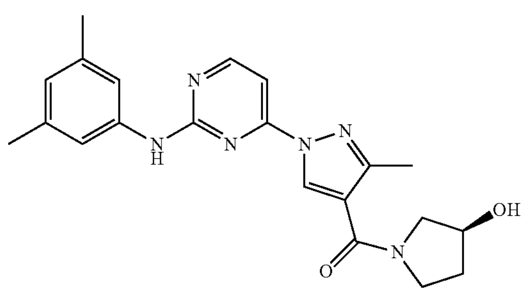 [SMILES: Cc1cc(C)cc(Nc2nccc(-n3cc(C(=O)N4CC[C@H](O)C4)c(C)n3)n2)c1] | (S)-(1-(2-(3,5-dimethylphenylamino)pyrimidin-4-yl)-3-methyl-1H-pyrazol-4-yl)(3-hydroxypyrrolidin-1-yl)methanone; 9.71 (s, 1H), 8.70 (s, 1H), 8.55 (d, J = 5.6 Hz, 1H), 7.38 (s, 2H), 7.20 (d, J = 5.6 Hz, 1H), 6.66 (s, 1H), 5.01 (m, 1H), 4.32 (s, 1H), 3.76-3.65 (m, 2H), 3.57-3.48 (m, 2H), 2.41 (s, 3H), 2.26 (s, 6H), 2.0-1.95 (m, 1H), 1.87-1.84 (m, 1H) | 393 |
| 32 | 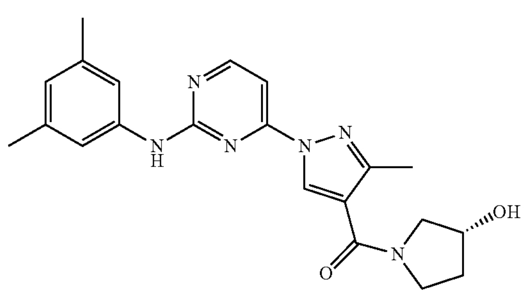 [SMILES: Cc1cc(C)cc(Nc2nccc(-n3cc(C(=O)N4CC[C@@H](O)C4)c(C)n3)n2)c1] | (R)-(1-(2-(3,5-dimethylphenylamino)pyrimidin-4-yl)-3-methyl-1H-pyrazol-4-yl)(3-hydroxypyrrolidin-1-yl)methanone; 9.71 (s, 1H), 8.72 (d, 1H), 8.55 (d, J = 5.2 Hz, 1H), 7.38 (s, 2H), 7.20 (d, J = 5.2 Hz, 1H), 6.66 (s, 1H), 5.01 (m, 1H), 4.33 (s, 1H), 3.80-3.75 (m, 2H), 3.57-3.54 (m, 2H), 2.41 (s, 3H), 2.26 (s, 6H), 2.0-1.80 (m, 2H) | 393 |

TABLE 2-continued

Compounds of Formula I

| Compound No. | Structure | NMR (300 Mz, DMSO-$d_6$) or Name | MS (ESI+) m/z |
|---|---|---|---|
| 33 | 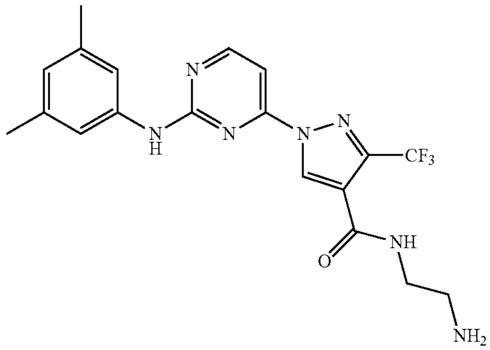 [SMILES: Cc1cc(C)cc(Nc2nccc(-n3cc(C(=O)NCCN)c(C(F)(F)F)n3)n2)c1] | N-(2-aminoethyl)-1-(2-(3,5-dimethyl-phenylamino)pyrimidin-4-yl)-3-(trifluoromethyl)-1H-pyrazole-4-carboxamide | 420 |
| 34 | 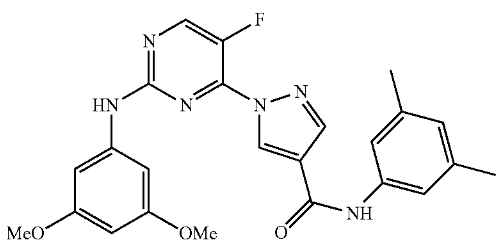 [SMILES: COc1cc(Nc2ncc(F)c(-n3cc(C(=O)Nc4cc(C)cc(C)c4)cn3)n2)cc(OC)c1] | 1-(2-(3,5-dimethoxyphenylamino)-5-fluoropyrimidin-4-yl)-N-(3,5-dimethyl-phenyl)-1H-pyrazole-4-carboxamide | 463 |
| 35 | 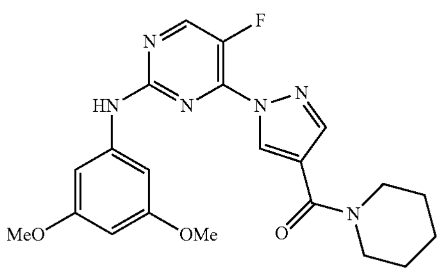 [SMILES: COc1cc(Nc2ncc(F)c(-n3cc(C(=O)N4CCCCC4)cn3)n2)cc(OC)c1] | (1-(2-(3,5-dimethoxyphenylamino)-5-fluoropyrimidin-4-yl)-1H-pyrazol-4-yl)(piperidin-1-yl)methanone | 427 |
| 36 | 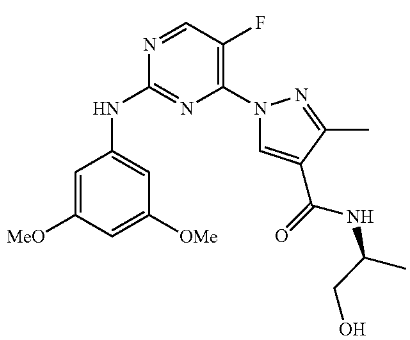 [SMILES: COc1cc(Nc2ncc(F)c(-n3cc(C(=O)N[C@@H](C)CO)c(C)n3)n2)cc(OC)c1] | (S)-1-(2-(3,5-dimethoxyphenylamino)-5-fluoropyrimidin-4-yl)-N-(1-hydroxy-propan-2-yl)-3-methyl-1H-pyrazole-4-carboxamide | 431 |
| 37 | 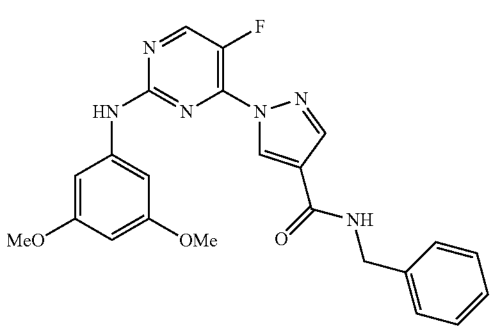 [SMILES: COc1cc(Nc2ncc(F)c(-n3cc(C(=O)NCc4ccccc4)cn3)n2)cc(OC)c1] | N-benzyl-1-(2-(3,5-dimethoxyphenyl-amino)-5-fluoropyrimidin-4-yl)-1H-pyrazole-4-carboxamide | 449 |

TABLE 2-continued

Compounds of Formula I

| Compound No. | Structure | NMR (300 Mz, DMSO-d$_6$) or Name | MS (ESI+) m/z |
|---|---|---|---|
| 38 | 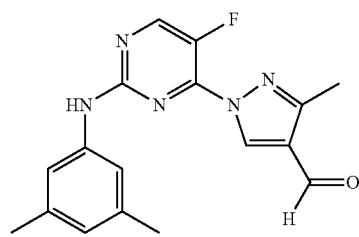 | (R)-(1-(2-(3,5-dimethylphenylamino)-5-fluoropyrimidin-4-yl)-3-methyl-1H-pyrazol-4-yl)(3-hydroxypyrrolidin-1-yl)methanone | 411 |

2-((1-(2-(3,5-dimethylphenylamino)-5-fluoropyrimidin-4-yl)-3-methyl-1H-pyrazol-4-yl)methylamino)ethanol; Compound No. 39

Method I

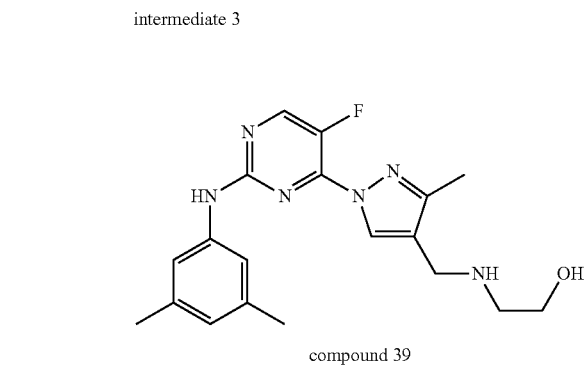

A solution of Intermediate No. 3 (65 mg, 0 2 mmol) and ethanolamine (18 µL, 0.3 mmol) in 2 mL of dichloromethane was stirred for 20 minutes at room temperature. To this, was added NaBH(OAc)$_3$ (64 mg, 0.3 mmol) at room temperature. The reaction was stirred for 15 hour at room temperature and then quenched with 1N-NaOH. It was extracted with ethyl acetate and washed twice with brine. The collected organic layer was dried over anhydrous sodium sulfate and then partially concentrated in vacou. The resulting residue was purified by silica gel chromatography to afford desired Compound No. 39 as a white solid (59 mg, 74%); $^1$H NMR (300 MHz, CDCl$_3$) δ, 8.38-8.40 (2H, m), 7.26 (1H, s), 6.67 (1H, s), 3.78 (2H, s), 3.70 (t, J=5.1 Hz, 2H), 2.81 (t, J=5.1 Hz, 2H), 2.36 (3H, s), 2.29 (6H, s); MS (ESI) m/z 371 [M+H]$^+$.

Method II 2-(4-((4-methyl-1-(5-methyl-2-(3,4,5-trimethoxyphenylamino)pyrimidin-4-yl)-1H-pyrrol-3-yl)methyl)piperazin-1-yl)ethanol: Compound 40

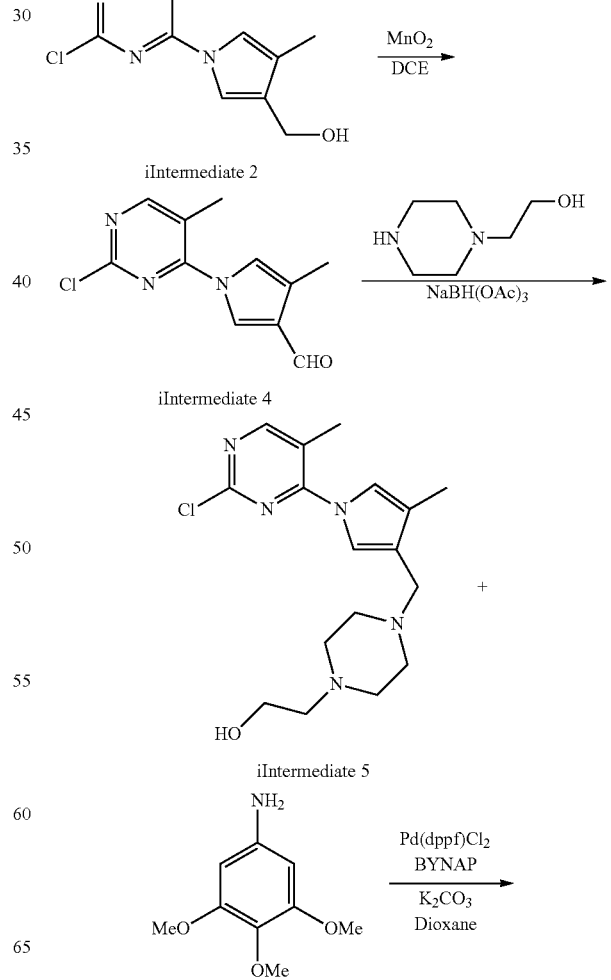

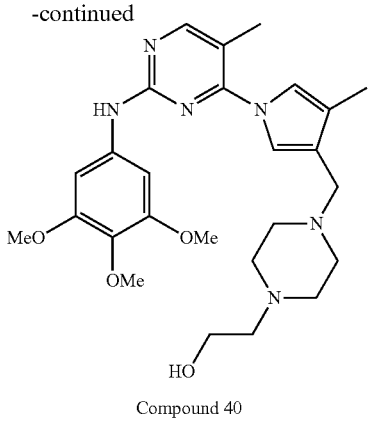

Compound 40

To a solution of Intermediate No. 2 (0.70 g, 2.92 mmol) in 30 mL of dichloroethane (DCE), was added MnO$_2$ (2.67 g, 17.5 mmol). After being stirred for 4 hours at 70° C., the reaction mixture was passed through a pad of Celite and rinsed with dichloromethane. The filtrate was concentrated in vacuo to give a desired Intermediate No. 4 as a pale yellow solid (0.6 g, 87%). A solution of Intermediate No. 4 (311 mg, 1.32 mmol) and 2-(piperazin-1-yl)ethanol (0.23 g, 1.77 mmol) in 10 mL of dichloromethane (DCM) was stirred for 20 minutes at room temperature. To this, was added NaBH(OAc)$_3$ (0.58 g, 2.6 mmol) at room temperature. The reaction was stirred for 3 hours at room temperature and then quenched with 1N-NaOH. It was extracted with ethyl acetate and washed twice with brine. The collected organic layer was dried over anhydrous sodium sulfate and then concentrated in vacou. The resulting residue was purified by silica gel chromatography to afford desired intermediate No. 5 as a white solid (0.42 mg, 91%). A 2 dram vial was charged with 2-(4-(1-(2-chloro-5-methylpyrimidin-4-yl)-4-methyl-1H-pyrrol-3-yl)methyl)piperazin-1-yl)ethanol (Intermediate No. 5) (70 mg, 0.2 mmol), 3,4,5-trimethoxyaniline (48 mg, 0.26 mmol), 83 mg (0 6 mmol) of potassium carbonate, Pd(dppf)Cl$_2$ (8 mg), BYNAP (12 mg) and 3 mL of anhydrous dioxane. After being degassed by nitrogen bubbling, the reaction mixture was heated at 100° C. for 16 hours and cooled to room temperature. The resulting insolubles were removed by filtration and then the filtrate was concentrated in vacuo. The resulting dark brown residue was purified by silica gel chromatography (5 to 15% MeOH/DCM) to afford desired Compound 40 as a pale yellow solid (74 mg, 75%); $^1$H NMR (300 MHz, CDCl$_3$) δ 9.43 (s, 1H), 8.34 (s, 1H), 7.39 (s, 1H), 7.30 (s, 1H), 7.18 (s, 2H), 3.77 (s, 9H), 3.61 (s, 2H), 3.45 (m, 2H), 3.21 (m, 2H), 2.38-2.32 (m, 8H), 2.19 (s, 3H), 2.03 (s, 3H); MS (ESI) m/z 497 [M+1-1]$^+$.

Preparation of Compound Nos. 41 to 139

The following compounds of the general structure shown Table 3 were prepared by a method I similar to that described in the preparation of Compound No. 39 using the appropriate aldehyde Intermediate No. 3 and appropriate amine HNR$^5$R$^6$ or method II similar to that described in the preparation of Compound No. 40 using the appropriate 2-chloropyrimidine Intermediate No. 5 and appropriate amine H$_2$NR$^2$.

1-((4-methyl-1-(5-methyl-2-(3,4,5-trimethoxyphenylamino)pyrimidin-4-yl)-1H-pyrrol-3-yl)methyl)azetidin-3-yl pivalate: Compound No. 93

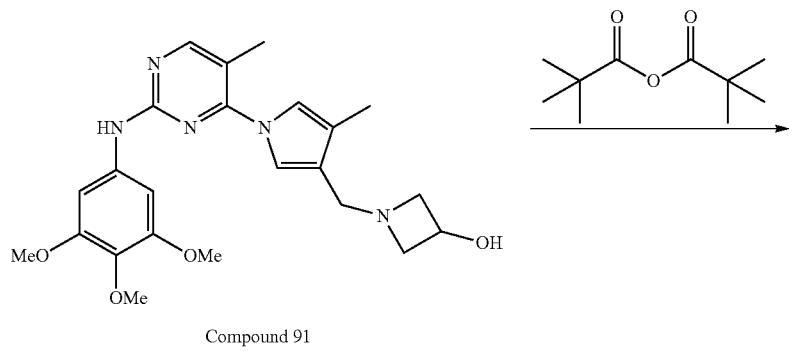

Compound 91

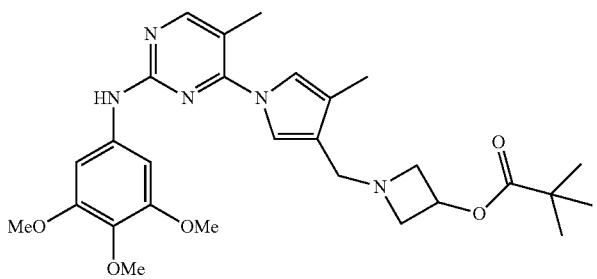

Compound 93

To a solution of 1-((4-methyl-1-(5-methyl-2-(3,4,5-trimethoxyphenylamino)pyrimidin-4-yl)-1H-pyrrol-3-yl)methyl)azetidin-3-ol (compound No. 91, 150 mg, 0.34 mmol) in 2 mL of anhydrous DMF, were added 5 mg of N,N-dimethylaminopyridine (DMAP) and trimethylacetic anhydride (128 mg, 0.68 mmol) at rt. After being stirred for 16 hours at room temperature, the reaction mixture was concentrated in vacuo. The resulting residue was extracted with EtOAc, washed with 2N-NaOH, dried over anhydrous Na$_2$SO$_4$, concentrated in vacuo and then purified by chromatography (5 to 15% MeOH/DCM) to afford desired Compound No. 93 as a colorless solid (98 mg, 55%); $^1$H NMR (300 MHz, CDCl$_3$) δ, 9.44 (s, 1H), 8.35 (2, 1H), 7.37 (s, 1H), 7.30 (s, 1H), 7.19 (s, 2H), 4.88-4.94 (m, 1H), 3.78 (s, 6H), 3.76 (m, 1H), 3.61 (s, 3H), 3.57-0.60 (m, 3H), 2.92 (m, 2H), 2.32 (s, 3H), 2.01 (s, 3H), 1.14 (s, 9H); MS (ESI) m/z 524 [M+H]$^+$.

4-(3-((1,4-diazepan-1-yl)methyl)-4-methyl-1H-pyrrol-1-yl)-5-methyl-N-(3,4,5-trimethoxyphenyl)pyrimidin-2-amine: Compound No. 96

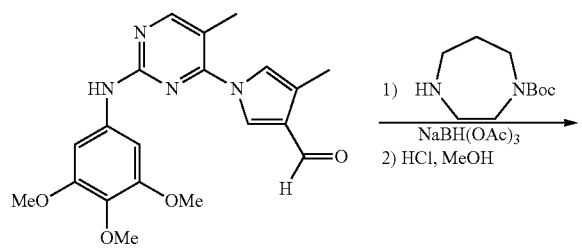

Intermediate 3

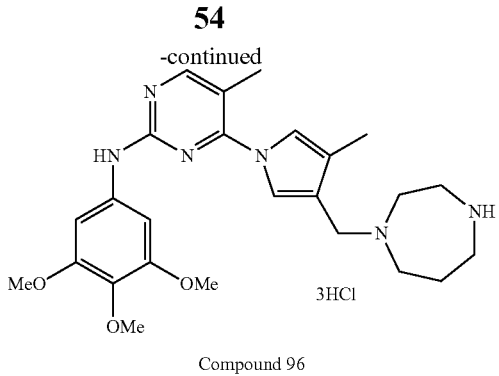

Compound 96

A solution of Intermediate No. 3 (200 mg, 0.52 mmol) and tert-butyl 1,4-diazepane-1-carboxylate (181 μL, 78 mmol) in 4 mL of dichloromethane was stirred for 20 minutes at room temperature. To this, was added NaBH(OAc)$_3$ (230 mg, 1.0 mmol) at room temperature. The reaction was stirred for 4 hours at room temperature and then quenched with 1N-NaOH. It was extracted with ethyl acetate and washed twice with brine. The collected organic layer was dried over anhydrous sodium sulfate and then concentrated in vacou. The resulting residue was purified by silica gel chromatography to afford Boc protected Compound No. 96 as a pale yellow solid (241 mg, 82%). The obtained compound was dissolved in 3 mL of methanol. To this, was added 2.5 mL of 4M-HCl. After being stirred for 6 hours at room temperature, the reaction mixture was partially concentrated in vacuo and then added EtOAc to form precipitation. The resulting yellow solids were collected by filtration and rinsed with EtOAC to give Compound No. 96 (230 mg, 94%) as a trishydrochloride salt; $^1$H NMR δ 11.13 (br s, 1H), 9.56 (s, 1H), 8.43 (s, 1H), 7.83 (s, 1H), 7.44 (s, 1H), 7.19 (s, 2H), 4.20 (m, 2H), 3.78 (s, 6H), 3.61 (s, 3H), 3.40-3.52 (m, 10H), 2.36 (s, 3H), 2.13 (s, 3H); MS (ESI) m/z 467 [M+H]$^+$.

4-(3-((1,4-diazepan-1-yl)methyl)-4-methyl-1H-pyrrol-1-yl)-5-methyl-N-(3,4,5-trimethoxyphenyl)pyrimidin-2-amine: Compound No. 97

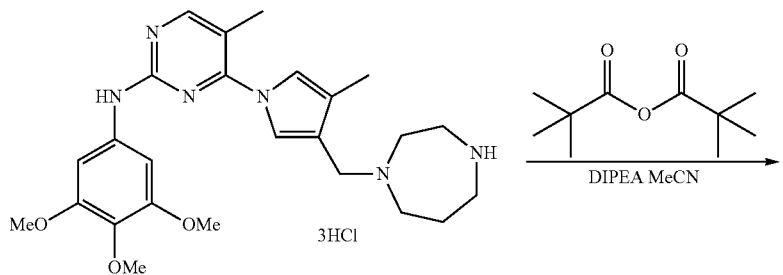

Compound 96

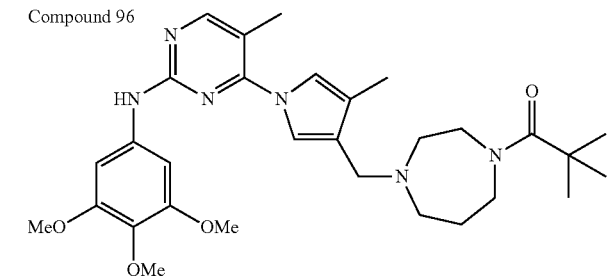

Compound 97

To a solution of Compound No. 96 (42 mg, 0.07 mmol) in 1 mL of acetonitrile and diisopropylethylamine (83 μL), were added catalytic amount of N,N-dimethylaminopyridine and trimethylacetic anhydride (28 μL, 0.14 mmol) at rt. After being stirred for 16 hours at room temperature, the reaction mixture was concentrated in vacuo. The resulting residue was extracted with EtOAc, washed with 2N-NaOH, dried over anhydrous sodium sulfate, concentrated in vacuo and then purified by chromatography (5 to 15% MeOH/DCM) to afford desired Compound No. 97 as a colorless solid (29 mg, 72%); $^1$H NMR (300 MHz, CDCl$_3$) δ, 9.44 (s, 1H), 8.35 (s, 1H), 7.38 (s, 1H), 7.31 (s, 1H), 7.19 (s, 2H), 3.77 (s, 6H), 3.61 (s, 3H), 3.49-3.52 (m, 6H), 2.73 (m, 2H), 2.33 (s, 3H), 2.04 (s, 3H), 1.76 (m, 2H), 1.18 (s, 9H); MS (ESI) m/z 551 [M+H]$^+$.

TABLE 3

Compounds of Formula I

| Compound No. | Structure | Compound Name; NMR (300 MHz, DMSO-d6) or | MS (ESI+) m/z |
|---|---|---|---|
| 41 | 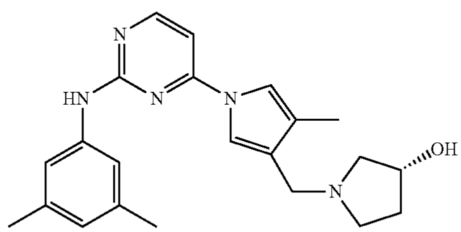 [SMILES: Cc1cc(C)cc(Nc2nccc(-n3cc(C)c(CN4CC[C@@H](O)C4)c3)n2)c1] | (R)-1-((1-(2-(3,5-dimethylphenylamino)pyrimidin-4-yl)-4-methyl-1H-pyrrol-3-yl)methyl)pyrrolidin-3-ol; 9.48 (s, 1H), 8.38 (d, J = 5.4 Hz, 1H), 7.52 (s, 1H), 7.42 (s, 1H), 7.39 (s, 2H), 6.98 (d, J = 5.4 Hz, 1H), 6.62 (s, 1H), 4.65 (br s, 1H), 4.18 (m, 1H), 3.45 (s, 2H), 2.73 (m, 1H), 2.55 (m, 1H), 2.31 (m, 2H), 2.26 (s, 6H), 2.03 (s, 3H), 1.98 (m, 1H), 1.54 (m, 1H) | 378 |
| 42 | 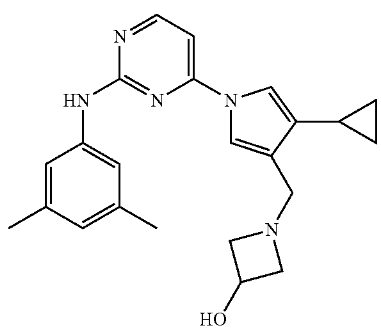 [SMILES: Cc1cc(C)cc(Nc2nccc(-n3cc(CN4CC(O)C4)c(C4CC4)c3)n2)c1] | 1-((4-cyclopropyl-1-(2-(3,5-dimethylphenylamino)pyrimidin-4-yl)-1H-pyrrol-3-yl)methyl)azetidin-3-ol; 9.48 (s, 1H), 8.38 (d, J = 5.4 Hz, 1H), 7.51 (s, 1H), 7.45 (s, 2H), 7.28 (s, 1H), 7.00 (d, J = 5.4 Hz, 1H), 6.63 (s, 1H), 5.27 (br s, 1H), 4.21-4.15 (m, 1H), 3.56-3.52 (m, 2H), 3.48 (s, 2H), 2.77-2.73 (m, 2H), 2.27 (s, 6H), 1.70-1.61 (m, 1H), 0.84-0.77 (m, 2H), 0.52-0.47 (m, 2H) | 390 |
| 43 | 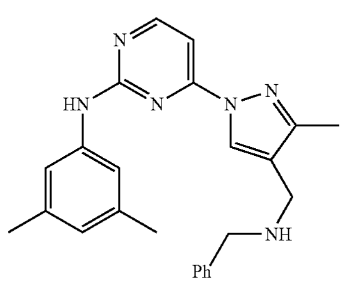 | 4-(4-((benzylamino)methyl)-3-methyl-1H-pyrazol-1-yl)-N-(3,5-dimethylphenyl)pyrimidin-2-amine; 9.58 (s, 1H), 8.47 (d, J = 5.6 Hz, 1H), 8.35 (s, 1H), 7.39-7.31 (m, 6H), 7.25-7.21 (m, 1H), 7.12 (d, J = 5.6 Hz, 1H), 6.64 (s, 1H), 3.75 (s, 2H), 3.58 (s, 2H), 3.31 (br s, 1H), 2.25 (s, 6H), 1.91 (s, 3H) | 399 |
| 44 | 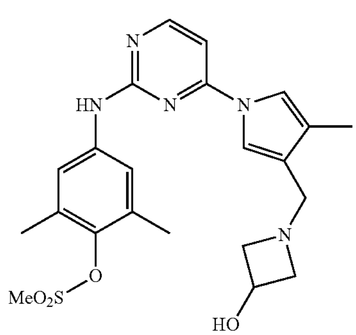 | 4-(4-(3-((3-hydroxyazetidin-1-yl)methyl)-4-methyl-1H-pyrrol-1-yl)pyrimidin-2-ylamino)-2,6-dimethylphenyl methanesulfonate | 458 |

TABLE 3-continued

Compounds of Formula I

| Compound No. | Structure | Compound Name; NMR (300 MHz, DMSO-d6) or | MS (ESI+) m/z |
|---|---|---|---|
| 45 | 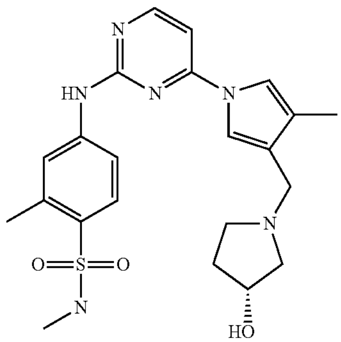 | (R)-4-(4-(3-((3-hydroxypyrrolidin-1-yl)methyl)-4-methyl-1H-pyrrol-1-yl)pyrimidin-2-ylamino)-N,2-dimethylbenzenesulfonamide; 9.70 (s, 1H), 8.41 (d, J = 5.4 Hz, 1H), 7.77-7.74 (m, 2H), 7.54-7.44 (m, 2H), 7.04 (m, 1H), 6.90 (s, 1H), 4.69 (s, 1H), 4.23 (s, 2H), 4.21-4.18 (m, 1H), 3.32 (s, 3H), 2.72 (s, 3H), 2.61 (m, 2H), 2.35-2.28 (m, 2H), 2.00 (s, 3H), 1.98-1.94 (m, 1H), 1.59-1.52 (m, 1H) | 457 |
| 46 | 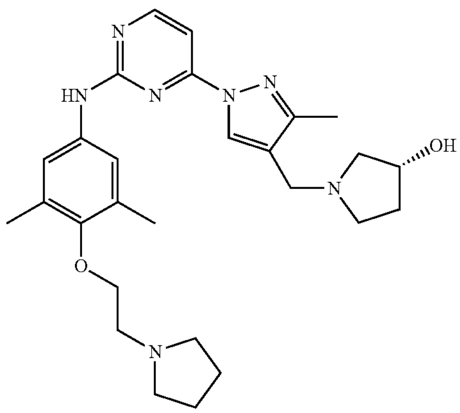 [SMILES: Cc1cc(Nc2nccc(-n3cc(CN4CC[C@@H](O)C4)c(C)n3)n2)cc(C)c1OCCN1CCCC1] | (R)-1-((1-(2-(3,5-dimethyl-4-(2-(pyrrolidin-1-yl)ethoxy)phenyl-amino)pyrimidin-4-yl)-3-methyl-1H-pyrazol-4-yl)methyl)pyrrolidin-3-ol | 492 |
| 47 | 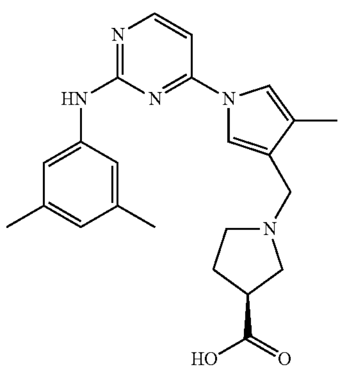 | (S)-1-((1-(2-(3,5-dimethylphenylamino)pyrimidin-4-yl)-4-methyl-1H-pyrrol-3-yl)methyl)pyrrolidine-3-carboxylic acid; 9.48 (s, 1H), 8.39 (d, J = 5.4 Hz, 1H), 7.55 (s, 1H), 7.43 (s, 1H), 7.39 (s, 2H), 6.98 (d, J = 5.4 Hz, 1H), 6.62 (s, 1H), 3.47 (s, 2H), 2.96 (m, 1H), 2.82 (m, 1H), 2.68-2.55 (m, 3H), 2.27 (s, 6H), 2.04 (s, 3H), 2.0-1.83 (m, 2H) | 406 |
| 48 | 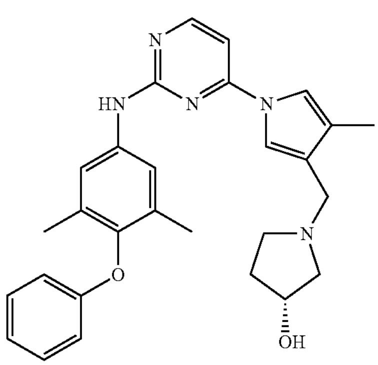 [SMILES: Cc1cn(-c2ccnc(Nc3cc(C)c(Oc4ccccc4)c(C)c3)n2)cc1CN1CC[C@@H](O)C1] | (R)-1-((1-(2-(3,5-dimethyl-4-phenoxyphenylamino)pyrimidin-4-yl)-4-methyl-1H-pyrrol-3-yl)methyl)pyrrolidin-3-ol; 9.60 (s, 1H), 8.43-8.41 (d, J = 5.7 Hz, 1H), 7.61 (s, 1H), 7.56 (s, 2H), 7.45 (s, 1H), 7.33-7.27 (m, 2H), 7.02-6.96 (m, 2H), 6.77-6.74 (m, 2H), 4.84 (s, 1H), 4.23 (m, 1H), 3.57-3.52 (m, 1H), 3.40 (s, 2H), 3.34-3.29 (m, 2H), 2.05 (s, 6H), 1.98 (s, 3H), 2.05-1.97 (m, 2H) | 470 |

TABLE 3-continued

Compounds of Formula I

| Compound No. | Structure | Compound Name; NMR (300 MHz, DMSO-d6) or | MS (ESI+) m/z |
|---|---|---|---|
| 49 | 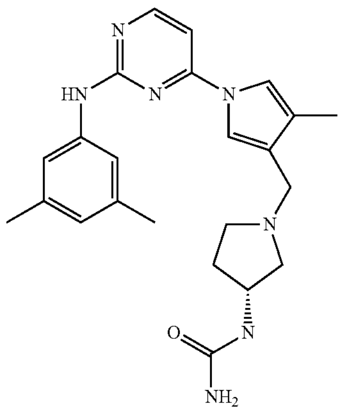 | (R)-1-(1-((1-(2-(3,5-dimethylphenylamino)pyrimidin-4-yl)-4-methyl-1H-pyrrol-3-yl)methyl)pyrrolidin-3-yl)urea; 9.48 (s, 1H), 5.38 (d, J = 5.4 Hz, 1H), 7.54 (s, 1H), 7.43 (s, 1H), 7.39 (s, 2H), 6.99 (d, J = 5.4 Hz, 1H), 6.24 (s, 1H), 6.07 (br s, 2H), 5.37 (br s, 2H), 3.99 (m, 1H), 3.50 (s, 2H), 3.43-3.22 (m, 4H), 2.49-2.44 (m, 2H), 2.26 (s, 6H), 2.05 (s, 3H) | 420 |
| 50 | 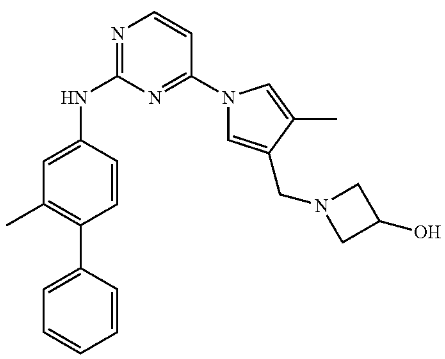 [SMILES: Cc1cn(-c2ccnc(Nc3ccc(-c4ccccc4)c(C)c3)n2)cc1CN1CC(O)C1] | 1-((4-methyl-1-(2-(2-methylbiphenyl-4-ylamino)pyrimidin-4-yl)-1H-pyrrol-3-yl)methyl)azetidin-3-ol; 9.71 (s, 1H), 8.45 (d, J = 5.6 Hz, 1H), 7.73-7.72 (m, 1H), 7.67-7.64 (m, 2H), 7.48-7.31 (m, 6H), 7.18 (d, J = 5.6 Hz, 1H), 7.05-7.03 (d, J = 5.6 Hz, 1H), 5.63 (br, 1H), 4.32-4.26 (m, 1H), 3.75-3.68 (m, 4H), 3.35 (s, 2H), 2.27 (s, 3H), 2.05 (s, 3H) | 426 |
| 51 | 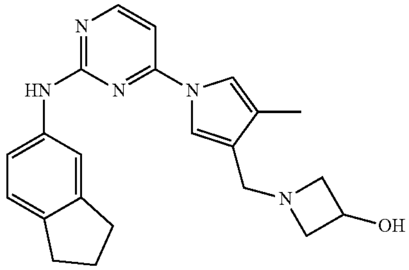 [SMILES: Cc1cn(-c2ccnc(Nc3ccc4c(c3)CCC4)n2)cc1CN1CC(O)C1] | 1-((1-(2-(2,3-dihydro-1H-inden-5-ylamino)pyrimidin-4-yl)-4-methyl-1H-pyrrol-3-yl)methyl)azetidin-3-ol; 9.50 (s, 1H), 8.38 (d, J = 5.6 Hz, 1H), 7.68 (s, 1H), 7.49 (s, 1H), 7.45 (s, 1H), 7.42 (s, 1H), 7.15 (d, J = 8.1 Hz), 6.98 (d, J = 5.6 Hz, 1H), 5.32 (br s, 1H), 4.20 (m, 1H), 3.54 (br s, 2H), 3.41 (br s, 2H), 2.89-2.79 (m, 6H), 2.04 (m, 2H), 2.0 (s, 3H) | 376 |
| 52 | 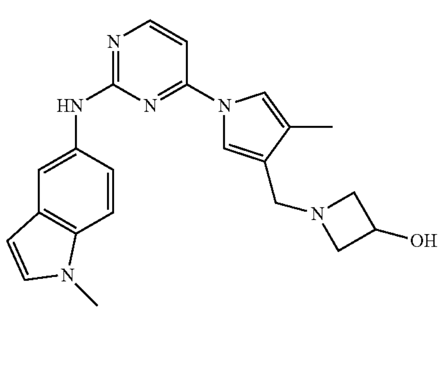 [SMILES: Cc1cn(-c2ccnc(Nc3ccc4c(ccn4C)c3)n2)cc1CN1CC(O)C1] | 1-((4-methyl-1-(2-(1-methyl-1H-indol-5-ylamino)pyrimidin-4-yl)-1H-pyrrol-3-yl)methyl)azetidin-3-ol | 389 |

TABLE 3-continued

Compounds of Formula I

| Compound No. | Structure | Compound Name; NMR (300 MHz, DMSO-d6) or | MS (ESI+) m/z |
|---|---|---|---|
| 53 | 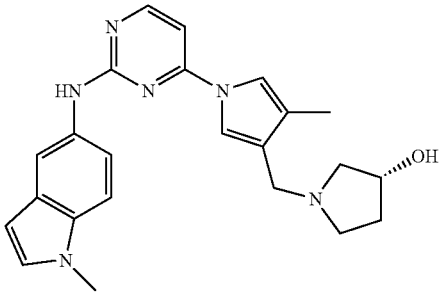 [SMILES: Cc1cn(-c2ccnc(Nc3ccc4c(ccn4C)c3)n2)cc1CN1CC[C@@H](O)C1] | (R)-1-((4-methyl-1-(2-(1-methyl-1H-indol-5-ylamino)pyrimidin-4-yl)-1H-pyrrol-3-yl)methyl)pyrrolidin-3-ol | 403 |
| 54 | 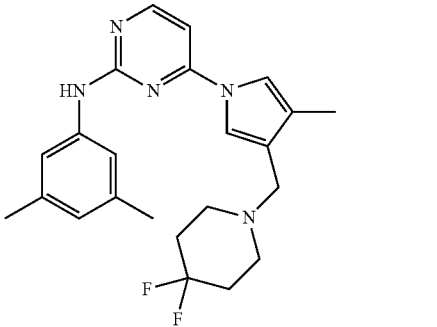 | 4-(3-((4,4-difluoropiperidin-1-yl)methyl)-4-methyl-1H-pyrrol-1-yl)-N-(3,5-dimethylphenyl)pyrimidin-2-amine; 9.47 (s, 1H), 8.39 (d, J = 5.7 Hz, 1H), 7.55 (s, 1H), 7.44 (s, 1H), 7.39 (s, 2H), 6.98 (d, J = 5.7 Hz, 1H), 6.62 (s, 1H), 3.46 (s, 2H), 2.67-2.32 (m, 4H), 2.25 (s, 6H), 2.05-1.80 (m, 1H), 1.99 (s, 3H) | 412 |
| 55 | 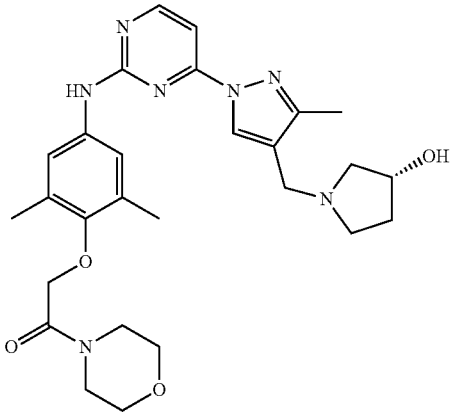 [SMILES: Cc1cc(Nc2nccc(-n3cc(CN4CC[C@@H](O)C4)c(C)n3)n2)cc(C)c1OCC(=O)N1CCOCC1] | (R)-2-(4-(4-(4-((3-hydroxypyrrolidin-1-yl)methyl)-3-methyl-1H-pyrazol-1-yl)pyrimidin-2-ylamino)-2,6-dimethylphenoxy)-1-morpholinoethanone; 8.39 (d, J = 5.4 Hz, 1H), 8.29 (s, 1H), 7.28 (s, 2H), 7.21 (d, J = 5.4 Hz, 1H), 7.04 (s, 1H), 4.52 (s, 2H), 4.36 (m, 1H), 3.8-3.5 (m, 9H), 3.53 (s, 2H), 2.71-2.56 (m, 4H), 2.36 (s, 6H), 2.32 (s, 3H), 2.2 (m, 1H), 1.77 (m, 1H) | 522 |
| 56 | 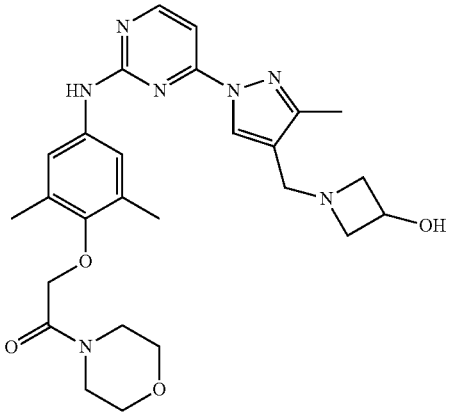 [SMILES: Cc1cc(Nc2nccc(-n3cc(CN4CC(O)C4)c(C)n3)n2)cc(C)c1OCC(=O)N1CCOCC1] | 2-(4-(4-(4-((3-hydroxyazetidin-1-yl)methyl)-3-methyl-1H-pyrazol-1-yl)pyrimidin-2-ylamino)-2,6-dimethylphenoxy)-1-morpholinoethanone; 8.39 (d, J = 5.4 Hz, 1H), 8.29 (s, 1H), 7.28 (s, 2H), 7.21 (d, J = 5.4 Hz, 1H), 7.03 (s, 1H), 5.32 (s, 1H), 4.99 (s, 2H), 4.90 (m, 1H), 3.9-3.6 (m, 10H), 3.52 (s, 2H), 3.02-2.97 (m, 2H), 2.34 (s, 6H), 2.32 (s, 3H) | 508 |

TABLE 3-continued

Compounds of Formula I

| Compound No. | Structure | Compound Name; NMR (300 MHz, DMSO-d6) or | MS (ESI+) m/z |
|---|---|---|---|
| 57 | 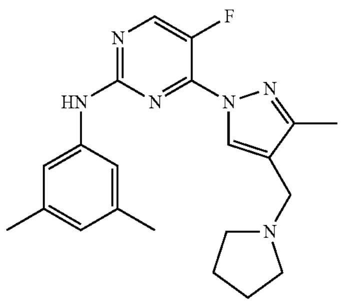 | N-(3,5-dimethylphenyl)-5-fluoro-4-(3-methyl-4-(pyrrolidin-1-ylmethyl)-1H-pyrazol-1-yl)pyrimidin-2-amine | 381 |
| 58 | 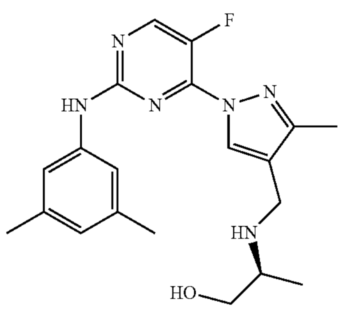 | (S)-2-((1-(2-(3,5-dimethylphenyl-amino)-5-fluoropyrimidin-4-yl)-3-methyl-1H-pyrazol-4-yl)methyl-amino)propan-1-ol | 385 |
| 59 | 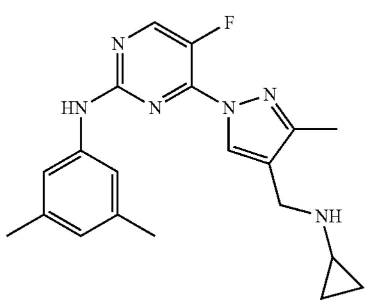 [SMILES: Cc1cc(C)cc(Nc2ncc(F)c(-n3cc(CNC4CC4)c(C)n3)n2)c1] | 4-(4-((cyclopropylamino)methyl)-3-methyl-1H-pyrazol-1-yl)-N-(3,5-dimethylphenyl)-5-fluoropyrimidin-2-amine | 367 |
| 60 | 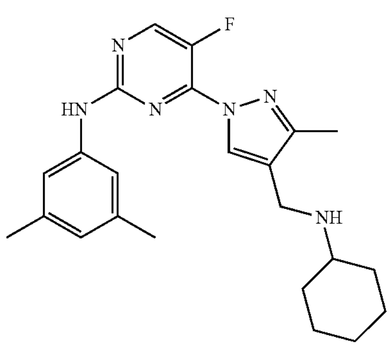 [SMILES: Cc1cc(C)cc(Nc2ncc(F)c(-n3cc(CNC4CCCCC4)c(C)n3)n2)c1] | 4-(4-((cyclohexylamino)methyl)-3-methyl-1H-pyrazol-1-yl)-N-(3,5-dimethylphenyl)-5-fluoropyrimidin-2-amine | 408 |
| 61 | 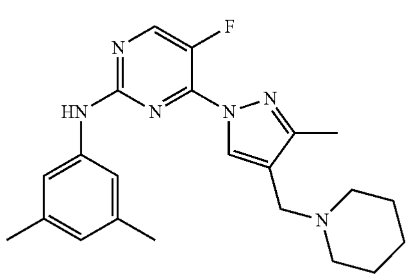 [SMILES: Cc1cc(C)cc(Nc2ncc(F)c(-n3cc(CN4CCCCC4)c(C)n3)n2)c1] | N-(3,5-dimethylphenyl)-5-fluoro-4-(3-methyl-4-(piperidin-1-ylmethyl)-1H-pyrazol-1-yl)pyrimidin-2-amine | 395 |

TABLE 3-continued

Compounds of Formula I

| Compound No. | Structure | Compound Name; NMR (300 MHz, DMSO-d6) or | MS (ESI+) m/z |
|---|---|---|---|
| 62 | 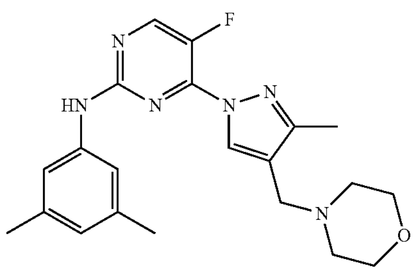 [SMILES: Cc1cc(C)cc(Nc2ncc(F)c(-n3cc(CN4CCOCC4)c(C)n3)n2)c1] | N-(3,5-dimethylphenyl)-5-fluoro-4-(3-methyl-4-(morpholinomethyl)-1H-pyrazol-1-yl)pyrimidin-2-amine | 397 |
| 63 | 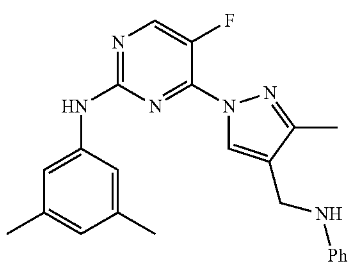 | N-(3,5-dimethylphenyl)-5-fluoro-4-(3-methyl-4-((phenylamino)methyl)-1H-pyrazol-1-yl)pyrimidin-2-amine | 403 |
| 64 | 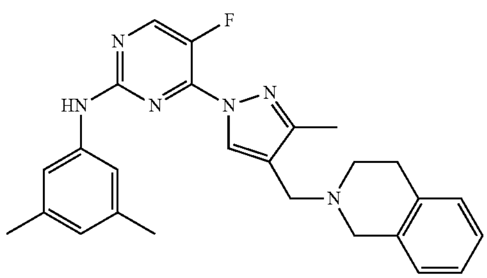 [SMILES: Cc1cc(C)cc(Nc2ncc(F)c(-n3cc(CN4CCc5ccccc5C4)c(C)n3)n2)c1] | 4-(4-((3,4-dihydroisoquinolin-2(1H)-yl)methyl)-3-methyl-1H-pyrazol-1-yl)-N-(3,5-dimethyl-phenyl)-5-fluoropyrimidin-2-amine | 443 |
| 65 | 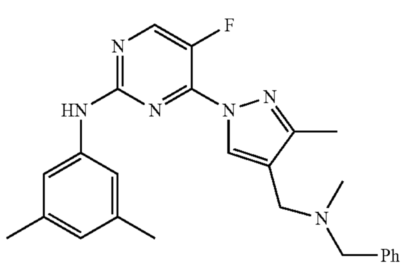 [SMILES: Cc1cc(C)cc(Nc2ncc(F)c(-n3cc(CN(C)Cc4ccccc4)c(C)n3)n2)c1] | 4-(4-((benzyl(methyl)amino)methyl)-3-methyl-1H-pyrazol-1-yl)-N-(3,5-dimethylphenyl)-5-fluoro-pyrimidin-2-amine | 431 |
| 66 | 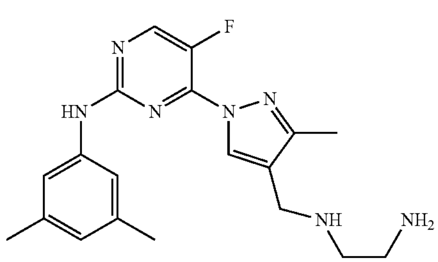 [SMILES: Cc1cc(C)cc(Nc2ncc(F)c(-n3cc(CNCCN)c(C)n3)n2)c1] | $N^1$-((1-(2-(3,5-dimethylphenyl-amino)-5-fluoropyrimidin-4-yl)-3-methyl-1H-pyrazol-4-yl)methyl)ethane-1,2-diamine | 370 |

TABLE 3-continued

Compounds of Formula I

| Compound No. | Structure | Compound Name; NMR (300 MHz, DMSO-d6) or | MS (ESI+) m/z |
|---|---|---|---|
| 67 | 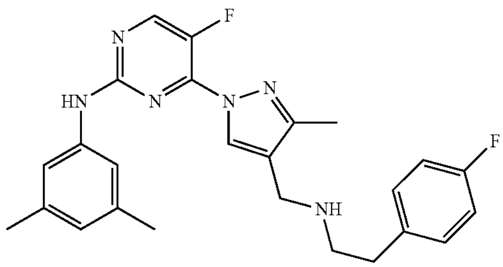 [SMILES: Cc1cc(C)cc(Nc2ncc(F)c(-n3cc(CNCCc4ccc(F)cc4)c(C)n3)n2)c1] | N-(3,5-dimethylphenyl)-5-fluoro-4-(4-((4-fluorophenethylamino)methyl)-3-methyl-1H-pyrazol-1-yl)pyrimidin-2-amine | 449 |
| 68 | 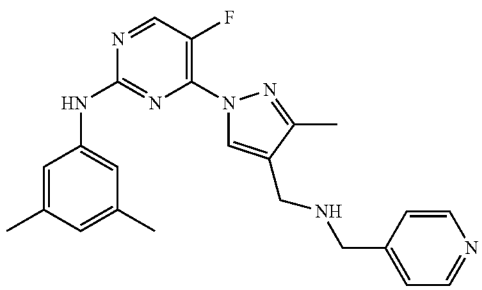 [SMILES: Cc1cc(C)cc(Nc2ncc(F)c(-n3cc(CNCc4ccncc4)c(C)n3)n2)c1] | N-(3,5-dimethylphenyl)-5-fluoro-4-(3-methyl-4-((pyridin-4-ylmethylamino)methyl)-1H-pyrazol-1-yl)pyrimidin-2-amine | 418 |
| 69 | 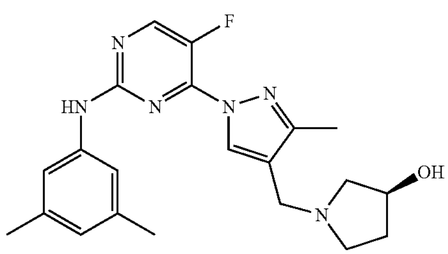 [SMILES: Cc1cc(C)cc(Nc2ncc(F)c(-n3cc(CN4CC[C@H](O)C4)c(C)n3)n2)c1] | (S)-1-((1-(2-(3,5-dimethylphenylamino)-5-fluoropyrimidin-4-yl)-3-methyl-1H-pyrazol-4-yl)methyl)pyrrolidin-3-ol | 397 |
| 70 | 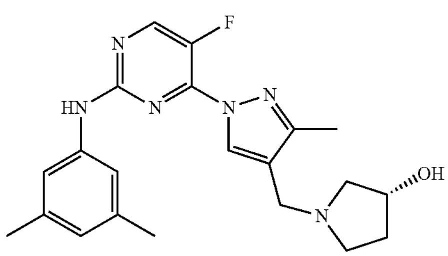 [SMILES: Cc1cc(C)cc(Nc2ncc(F)c(-n3cc(CN4CC[C@@H](O)C4)c(C)n3)n2)c1] | (R)-1-((1-(2-(3,5-dimethylphenylamino)-5-fluoropyrimidin-4-yl)-3-methyl-1H-pyrazol-4-yl)methyl)pyrrolidin-3-ol | 397 |
| 71 | 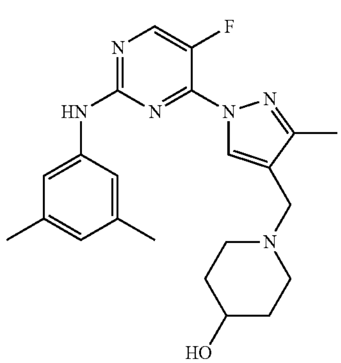 | 1-((1-(2-(3,5-dimethylphenylamino)-5-fluoropyrimidin-4-yl)-3-methyl-1H-pyrazol-4-yl)methyl)piperidin-4-ol | 411 |

TABLE 3-continued

Compounds of Formula I

| Compound No. | Structure | Compound Name; NMR (300 MHz, DMSO-d6) or | MS (ESI+) m/z |
|---|---|---|---|
| 72 | 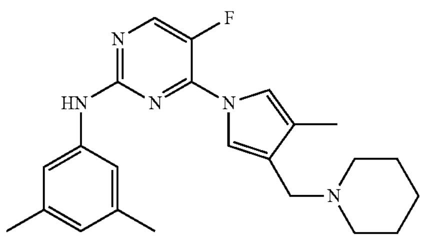 [SMILES: Cc1cc(C)cc(Nc2ncc(F)c(-n3cc(C)c(CN4CCCCC4)c3)n2)c1] | N-(3,5-dimethylphenyl)-5-fluoro-4-(3-methyl-4-(piperidin-1-ylmethyl)-1H-pyrrol-1-yl)pyrimidin-2-amine | 394 |
| 73 | 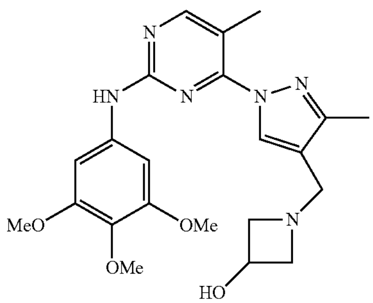 [SMILES: COc1cc(Nc2ncc(C)c(-n3cc(CN4CC(O)C4)c(C)n3)n2)cc(OC)c1OC] | 1-((3-methyl-1-(5-methyl-2-(3,4,5-trimethoxyphenylamino)pyrimidin-4-yl)-1H-pyrazol-4-yl)methyl)azetidin-3-ol; 9.50 (s, 1H), 8.43 (s, 1H), 8.40 (s, 1H), 7.15 (s, 2H), 3.39 (s, 9H), 3.62 (s, 2H), 3.54 (m, 1H), 3.24 (m, 4H), 2.44 (s, 3H), 2.24 (s, 3H) | 441 |
| 74 | 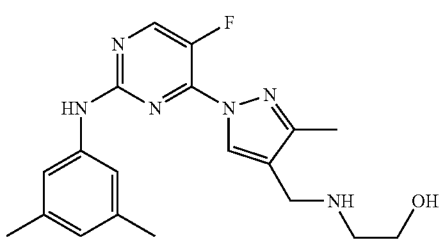 [SMILES: Cc1cc(C)cc(Nc2ncc(F)c(-n3cc(CNCCO)c(C)n3)n2)c1] | 2-((1-(2-(3,5-dimethylphenyl-amino)-5-fluoropyrimidin-4-yl)-3-methyl-1H-pyrazol-4-yl)methyl-amino)ethanol | 371 |
| 75 | 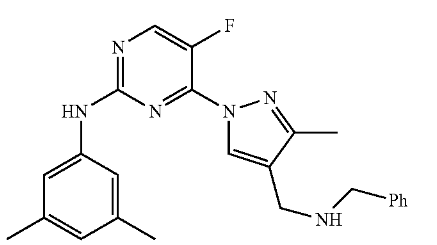 [SMILES: Cc1cc(C)cc(Nc2ncc(F)c(-n3cc(CNCc4ccccc4)c(C)n3)n2)c1] | 4-(4-((benzylamino)methyl)-3-methyl-1H-pyrazol-1-yl)-N-(3,5-dimethylphenyl)-5-fluoropyrimidin-2-amine | 417 |
| 76 | 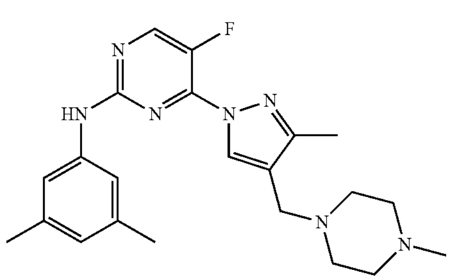 | N-(3,5-dimethylphenyl)-5-fluoro-4-(3-methyl-4-((4-methylpiperazin-1-yl)methyl)-1H-pyrazol-1-yl)pyrimidin-2-amine | 410 |

TABLE 3-continued

Compounds of Formula I

| Compound No. | Structure | Compound Name; NMR (300 MHz, DMSO-d6) or | MS (ESI+) m/z |
|---|---|---|---|
| 77 | 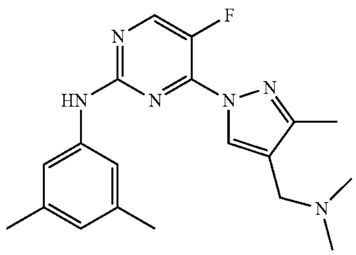 | 4-(4-((dimethylamino)methyl)-3-methyl-1H-pyrazol-1-yl)-N-(3,5-dimethylphenyl)-5-fluoropyrimidin-2-amine | 355 |
| 78 | 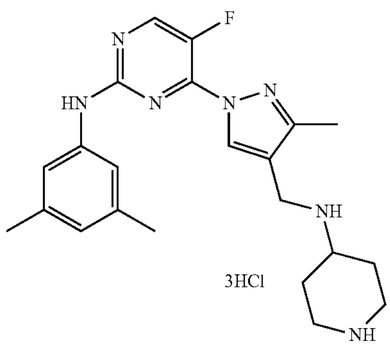 [SMILES: Cc1cc(C)cc(Nc2ncc(F)c(-n3cc(CNC4CCNCC4)c(C)n3)n2)c1] | N-(3,5-dimethylphenyl)-5-fluoro-4-(3-methyl-4-((piperidin-4-ylamino)methyl)-1H-pyrazol-1-yl)pyrimidin-2-amine trihydrochloride | 410 |
| 79 | 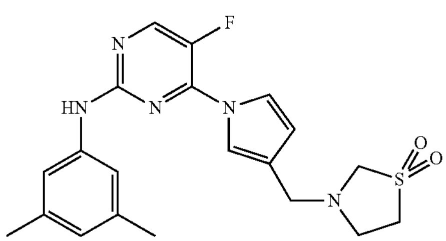 [SMILES: Cc1cc(C)cc(Nc2ncc(F)c(-n3ccc(CN4CCS(=O)(=O)C4)c3)n2)c1] | N-(3,5-dimethylphenyl)-5-fluoro-4-(3-(3-sulfonylpyrrolidin-1-ylmethyl)-1H-pyrrol-1-yl)pyrimidin-2-amine | 416 |
| 80 | 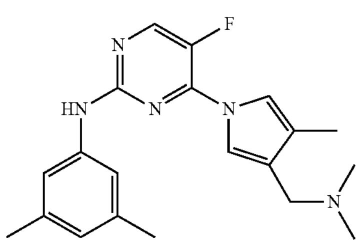 | 4-(3-((dimethylamino)methyl)-4-methyl-1H-pyrrol-1-yl)-N-(3,5-dimethylphenyl)-5-fluoropyrimidin-2-amine; 9.58 (s, 1H), 8.55 (d, J = 4.8 Hz, 1H), 7.47 (s, 1H), 7.40 (s, 1H), 7.38 (s, 2H), 6.63 (s, 1H), 3.24 (s, 2H), 2.25 (s, 6H), 2.16 (s, 6H), 2.05 (s, 3H) | 353 |
| 81 | 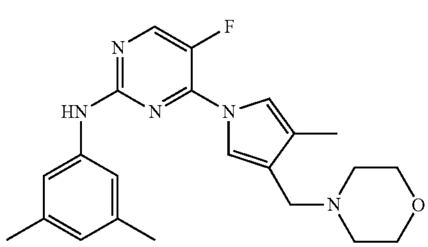 [SMILES: Cc1cc(C)cc(Nc2ncc(F)c(-n3cc(C)c(CN4CCOCC4)c3)n2)c1] | N-(3,5-dimethylphenyl)-5-fluoro-4-(3-methyl-4-(morpholinomethyl)-1H-pyrrol-1-yl)pyrimidin-2-amine | 396 |

TABLE 3-continued

Compounds of Formula I

| Compound No. | Structure | Compound Name; NMR (300 MHz, DMSO-d6) or | MS (ESI+) m/z |
|---|---|---|---|
| 82 | 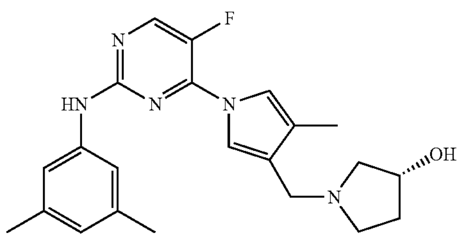 [SMILES: Cc1cc(C)cc(Nc2ncc(F)c(-n3cc(C)c(CN4CC[C@@H](O)C4)c3)n2)c1] | (R)-1-((1-(2-(3,5-dimethylphenyl-amino)-5-fluoropyrimidin-4-yl)-4-methyl-1H-pyrrol-3-yl)methyl)pyrrolidin-3-ol | 396 |
| 83 | 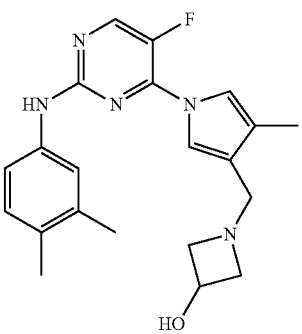 [SMILES: Cc1ccc(Nc2ncc(F)c(-n3cc(C)c(CN4CC(O)C4)c3)n2)cc1C] | 1-((1-(2-(3,4-dimethylphenylamino)-5-fluoropyrimidin-4-yl)-4-methyl-1H-pyrrol-3-yl)methyl)azetidin-3-ol; 9.55 (s, 1H), 8.52 (d, J = 2.1 Hz, 1H), 7.51 (s, 1H), 7.43 (s, 1H), 7.34-7.39 (m, 2H), 7.05 (d, J = 8.1 Hz, 1H), 5.31 (d, J = 6.3 Hz, 1H), 4.20-4.22 (m, 1H), 3.47-3.53 (m, 2H), 3.41 (s, 2H), 2.75-2.79 (m, 2H), 2.23 (s, 3H), 2.18 (s, 3H), 2.02 (s, 3H) | 382 |
| 84 | 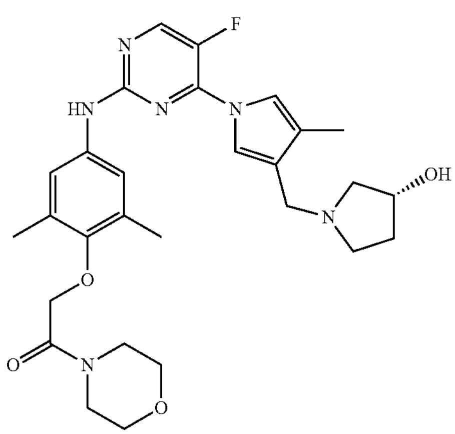 [SMILES: Cc1cn(-c2nc(Nc3cc(C)c(OCC(=O)N4CCOCC4)c(C)c3)ncc2F)cc1CN1CC[C@@H](O)C1] | (R)-2-(4-(5-fluoro-4-(3-((3-hydroxypyrrolidin-1-yl)methyl)-4-methyl-1H-pyrrol-1-yl)pyrimidin-2-ylamino)-2,6-dimethylphenoxy)-1-morpholinoethanone; 9.53 (s, 1H), 8.53 (d, J = 4.5 Hz, 1H), 7.56 (s, 1H), 7.35 (s, 3H), 4.75 (br s, 1H), 4.50 (s, 2H), 4.21 (br s, 1H), 3.58-3.61 (m, 8H), 3.49 (m, 4H), 2.22 (s, 6H), 2.05 (s, 3H), 2.02-1.96 (m, 2H) | 438 |
| 85 | 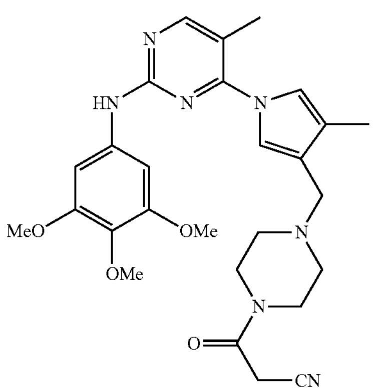 [SMILES: COc1cc(Nc2ncc(C)c(-n3cc(C)c(CN4CCN(C(=O)CC#N)CC4)c3)n2)cc(OC)c1OC] | 3-(4-((4-methyl-1-(5-methyl-2-(3,4,5-trimethoxyphenylamino)pyrimidin-4-yl)-1H-pyrrol-3-yl)methyl)piperazin-1-yl)-3-oxopropanenitrile; 9.55 (s, 1H), 8.44 (s, 1H), 7.76 (s, 1H), 7.44 (s, 1H), 7.20 (s, 2H), 4.17 (s, 2H), 4.04 (br d, J = 11.1 Hz, 4H), 3.78 (s, 6H), 3.62 (d, 3H), 3.08 (br d, J = 11.1 Hz, 4H), 3.08-3.17 (m, 2H), 2.36 (s, 3H), 2.12 (s, 3H) | 520 |

TABLE 3-continued

Compounds of Formula I

| Compound No. | Structure | Compound Name; NMR (300 MHz, DMSO-d6) or | MS (ESI+) m/z |
|---|---|---|---|
| 86 | 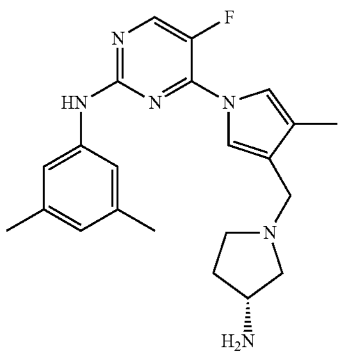 | (R)-4-(3-((3-aminopyrrolidin-1-yl)methyl)-4-methyl-1H-pyrrol-1-yl)-N-(3,5-dimethylphenyl)-5-fluoropyrimidin-2-amine; 9.67 (s, 1H), 8.64 (d, J = 4.5 Hz, 1H), 7.85 (s, 1H), 7.46 (s, 1H), 7.33 (s, 2H), 6.64 (s, 1H), 4.09 (s, 2H), 4.01-3.98 (m, 1H), 3.38-3.30 (m, 2H), 3.24-3.20 (m, 2H), 2.38-2.30 (m, 2H), 2.27 (s, 6H), 2.18 (s, 3H) | 391 |
| 87 | 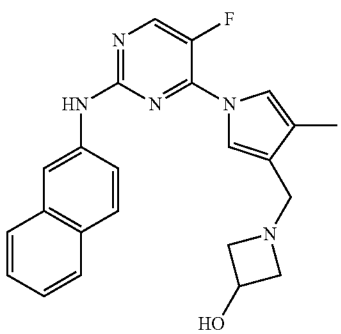 [SMILES: Cc1cn(-c2nc(Nc3ccc4ccccc4c3)ncc2F)cc1CN1CC(O)C1] | 1-((1-(5-fluoro-2-(naphthalen-2-ylamino)pyrimidin-4-yl)-4-methyl-1H-pyrrol-3-yl)methyl)azetidin-3-ol; 10.04 (s, 1H), 8.67 (d, J = 4.5 Hz, 1H), 8.40 (s, 1H), 7.79-7.70 (m, 3H), 7.73 (m, 2H), 7.47 (s, 2H), 7.35 (q, J = 6.9 Hz, 1H), 5.88 (br s 1H), 4.39 (s, 1H), 3.93-4.00 (m, 4H), 2.57-2.64 (m, 2H), 2.11 (s, 3H) | 404 |
| 88 | 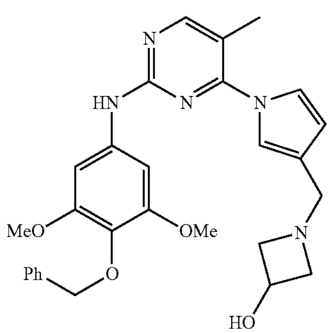 [SMILES: COc1cc(Nc2ncc(C)c(-n3ccc(CN4CC(O)C4)c3)n2)cc(OC)c1OCc1ccccc1] | 1-((1-(2-(4-(benzyloxy)-3,5-dimethoxyphenylamino)-5-methylpyrimidin-4-yl)-1H-pyrrol-3-yl)methyl)azetidin-3-ol; 9.46 (s, 1H), 8.35 (s, 1H), 7.50 (s, 1H), 7.45 (s, 1H), 7.39-7.30 (m, 6H), 7.21 (s, 2H), 5.27 (d, J = 6.3 Hz, 1H), 4.85 (s, 2H), 4.20-4.14 (m, 1H), 3.79 (s, 6H), 3.51-3.46 (m, 2H), 3.37 (s, 2H), 2.70-2.65 (m, 2H), 2.01 (s, 3H) | 502 |
| 89 | 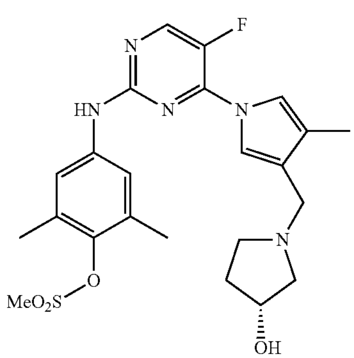 | (R)-4-(5-fluoro-4-(3-((3-hydroxypyrrolidin-1-yl)methyl)-4-methyl-1H-pyrrol-1-yl)pyrimidin-2-ylamino)-2,6-dimethylphenyl-methanesulfonate; 9.73 (s, 1H), 8.57 (d, J = 4.8 Hz, 1H), 7.48 (d, J = 7.2 Hz, 3H), 7.35 (s, 1H), 4.67 (d, J = 4.2 Hz, 1H), 4.20-4.17 (m, 1H), 3.50 (s, 3H), 3.42 (d, J = 1.8 Hz, 2H), 2.75-2.70 (m, 1H), 2.60-55 (m, 1H), 2.30 (s, 8H), 2.05 (s, 3H), 2.01-1.95 (m, 1H), 1.58-1.51 (m, 1H) | 490 |

TABLE 3-continued

Compounds of Formula I

| Compound No. | Structure | Compound Name; NMR (300 MHz, DMSO-d6) or | MS (ESI+) m/z |
|---|---|---|---|
| 90 | 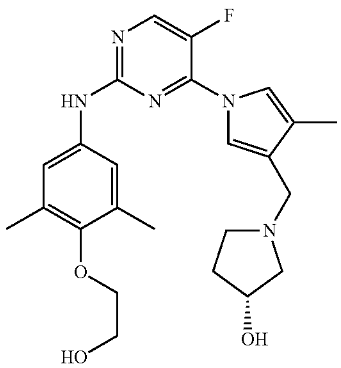 | (R)-1-((1-(5-fluoro-2-(4-(2-hydroxyethoxy)-3,5-dimethylphenylamino)pyrimidin-4-yl)-4-methyl-1H-pyrrol-3-yl)methyl)pyrrolidin-3-ol; 9.49 (s, 1H), 8.52 (d, 4.5 Hz, 1H), 7.47 (s, 1H), 7.34 (s, 3H), 4.86 (t, 11.1 Hz, 1H), 4.70 (s, 1H), 4.20 (s, 1H), 3.74-3.68 (m, 6H), 3.28 (s, 2H), 2.73 (s, 2H), 2.23 (s, 6H), 2.05 (s, 3H), 2.01-1.98 (m, 1H), 1.57 (s, 1H) | 456 |
| 91 | 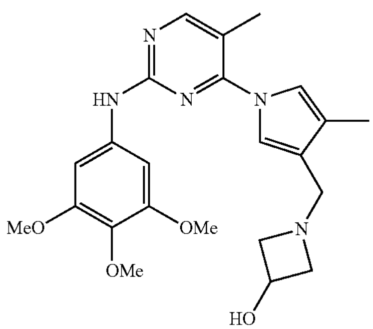 [SMILES: COc1cc(Nc2ncc(C)c(-n3cc(C)c(CN4CC(O)C4)c3)n2)cc(OC)c1OC] | 1-((4-methyl-1-(5-methyl-2-(3,4,5-trimethoxyphenylamino)pyrimidin-4-yl)-1H-pyrrol-3-yl)methyl)azetidin-3-ol; 9.44 (s, 1H), 8.35 (s, 1H), 7.30 (3, 1H), 7.26 (s, 1H), 7.19 (s, 2H), 5.26 (d, 6.3 Hz, 1H), 3.79 (s, 6H), 3.62 (s, 3H), 3.50-3.60 (m, 3H), 3.28 (s, 2H), 2.73-2.44 (m, 4H), 2.33 (s, 3H), 2.01 (s, 3H) | 440 |
| 92 | 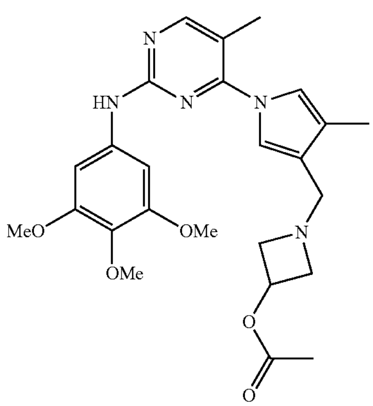 [SMILES: COc1cc(Nc2ncc(C)c(-n3cc(C)c(CN4CC(OC(C)=O)C4)c3)n2)cc(OC)c1OC] | 1-((4-methyl-1-(5-methyl-2-(3,4,5-trimethoxyphenylamino)pyrimidin-4-yl)-1H-pyrrol-3-yl)methyl)azetidin-3-yl acetate; 9.44 (s, 1H), 8.35 (s, 1H), 7.36 (s, 1H), 7.31 (s, 1H), 7.20 (s, 2H), 3.79 (s, 6H), 3.62 (s, 3H), 3.50-3.60 (m, 3H), 3.39 (s, 2H), 2.97-3.00 (m, 2H), 2.33 (s, 3H), 2.32 (s, 3H), 2.06 (s, 3H) | 482 |
| 93 | 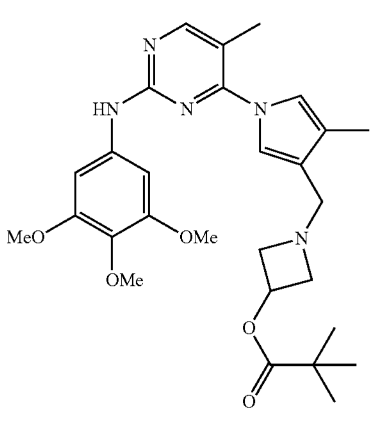 [SMILES: COc1cc(Nc2ncc(C)c(-n3cc(C)c(CN4CC(OC(=O)C(C)(C)C)C4)c3)n2)cc(OC)c1OC] | 1-((4-methyl-1-(5-methyl-2-(3,4,5-trimethoxyphenylamino)pyrimidin-4-yl)-1H-pyrrol-3-yl)methyl)azetidin-3-yl pivalate; 9.44 (s, 1H), 8.35 (s, 1H), 7.37 (s, 1H), 7.30 (s, 1H), 7.19 (s, 2H), 4.88-4.94 (m, 1H), 3.78 (s, 6H), 3.76 (m, 1H), 3.61 (s, 3H), 3.57-3.60 (m, 2H), 2.94-2.90 (m, 2H), 2.32 (s, 3H), 2.01 (s, 3H), 1.14 (s, 9H) | 524 |

TABLE 3-continued

Compounds of Formula I

| Compound No. | Structure | Compound Name; NMR (300 MHz, DMSO-d6) or | MS (ESI+) m/z |
|---|---|---|---|
| 94 | 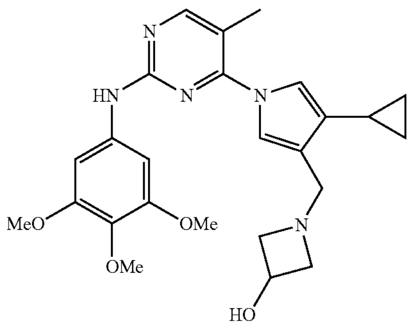 [SMILES: COc1cc(Nc2ncc(C)c(-n3cc(CN4CC(O)C4)c(C4CC4)c3)n2)cc(OC)c1OC] | 1-((4-cyclopropyl-1-(5-methyl-2-(3,4,5-trimethoxyphenylamino)pyrimidin-4-yl)-1H-pyrrol-3-yl)methyl)azetidin-3-ol; 9.43 (s, 1H), 8.34 (s, 1H), 7.30 (s, 1H), 7.17 (s, 2H), 7.10 (s, 1H), 5.32 (d, J = 6.3 Hz, 1H), 4.14-4.22 (m, 1H), 3.78 (s, 6H), 3.61 (s, 3H), 3.49-3.52 (m, 4H), 2.89-2.80 (m, 2H), 2.31 (s, 3H), 1.64-1.70 (m, 1H), 0.77-0.80 (m, 2H), 0.47-0.48 (m, 2H) | 466 |
| 95 | 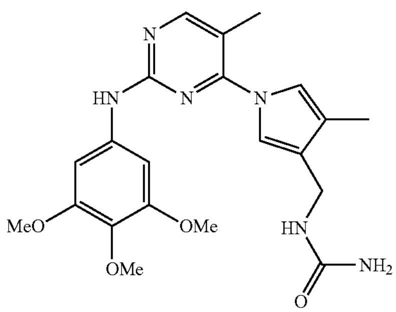 [SMILES: COc1cc(Nc2ncc(C)c(-n3cc(C)c(CNC(N)=O)c3)n2)cc(OC)c1OC] | 1-((4-methyl-1-(5-methyl-2-(3,4,5-trimethoxyphenylamino)pyrimidin-4-yl)-1H-pyrrol-3-yl)methyl)urea; 9.46 (s, 1H), 8.35 (s, 1H), 7.39 (s, 1H), 7.32 (s, 1H), 7.20 (s, 2H), 6.02-0.08 (m, 1H), 5.43 (s, 2H), 4.02 (d, J = 5,4 Hz, 2H), 3.77 (s, 6H), 3.61 (s, 3H), 2.32 (s, 3H), 2.02 (s, 3H) | 427 |
| 96 | 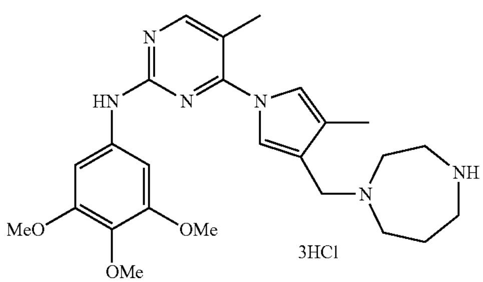 [SMILES: COc1cc(Nc2ncc(C)c(-n3cc(C)c(CN4CCCNCC4)c3)n2)cc(OC)c1OC] | 4-(3-((1,4-diazepan-1-yl)methyl)-4-methyl-1H-pyrrol-1-yl)-5-methyl-N-(3,4,5-trimethoxyphenyl)pyrimidin-2-amine trihydrochloride | 467 |
| 97 | 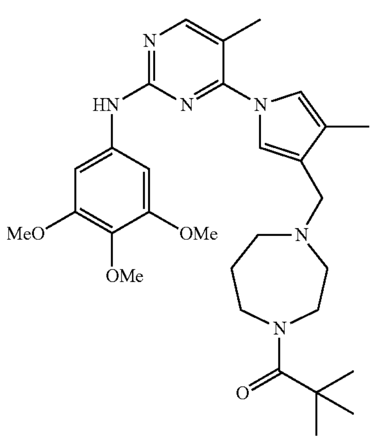 [SMILES: COc1cc(Nc2ncc(C)c(-n3cc(C)c(CN4CCCN(C(=O)C(C)(C)C)CC4)c3)n2)cc(OC)c1OC] | 2,2-dimethyl-1-(4-((4-methyl-1-(5-methyl-2-(3,4,5-trimethoxyphenylamino)pyrimidin-4-yl)-1H-pyrrol-3-yl)methyl)-1,4-diazepan-1-yl)propan-1-one; 9.44 (s, 1H), 8.35 (s, 1H), 7.38 (s, 1H), 7.31 (s, 1H), 7.19 (s, 2H), 3.77 (s, 6H), 3.61 (s, 3H), 3.49-3.52 (m, 6H), 2.73 (m, 2H), 2.33 (s, 3H), 2.04 (s, 3H), 1.76 (m, 2H), 1.18 (s, 9H) | 551 |

TABLE 3-continued

Compounds of Formula I

| Compound No. | Structure | Compound Name; NMR (300 MHz, DMSO-d6) or | MS (ESI+) m/z |
|---|---|---|---|
| 98 | 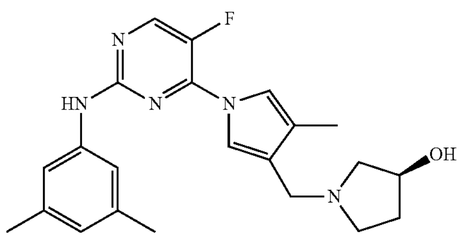 [SMILES: Cc1cc(C)cc(Nc2ncc(F)c(-n3cc(C)c(CN4CC[C@H](O)C4)c3)n2)c1] | (S)-1-((1-(2-(3,5-dimethylphenyl-amino)-5-fluoropyrimidin-4-yl)-4-methyl-1H-pyrrol-3-yl)methyl)pyrrolidin-3-ol | 396 |
| 99 | 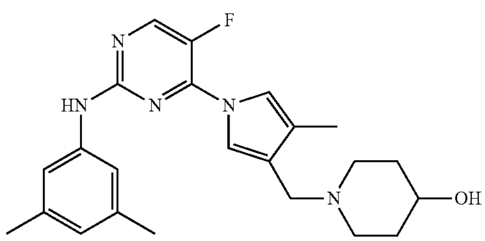 [SMILES: Cc1cc(C)cc(Nc2ncc(F)c(-n3cc(C)c(CN4CCC(O)CC4)c3)n2)c1] | 1-((1-(2-(3,5-dimethylphenyl-amino)-5-fluoropyrimidin-4-yl)-4-methyl-1H-pyrrol-3-yl)methyl)piperidin-4-ol | 410 |
| 100 | 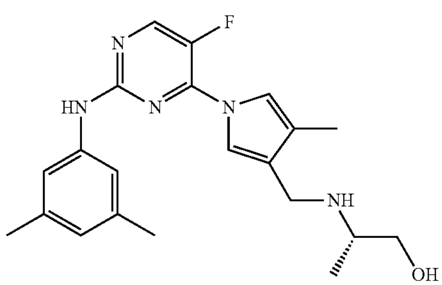 [SMILES: Cc1cc(C)cc(Nc2ncc(F)c(-n3cc(C)c(CN[C@@H](C)CO)c3)n2)c1] | (S)-2-((1-(2-(3,5-dimethylphenyl-amino)-5-fluoropyrimidin-4-yl)-4-methyl-1H-pyrrol-3-yl)methyl-amino)propan-1-ol | 384 |
| 101 | 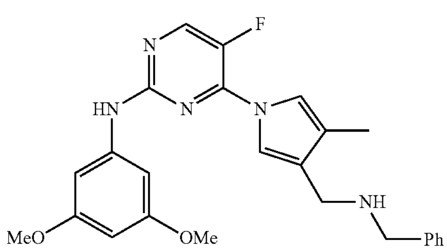 [SMILES: COc1cc(Nc2ncc(F)c(-n3cc(C)c(CNCc4ccccc4)c3)n2)cc(OC)c1] | 4-(3-((benzylamino)methyl)-4-methyl-1H-pyrrol-1-yl)-N-(3,5-dimethoxyphenyl)-5-fluoro-pyrimidin-2-amine | 448 |
| 102 | 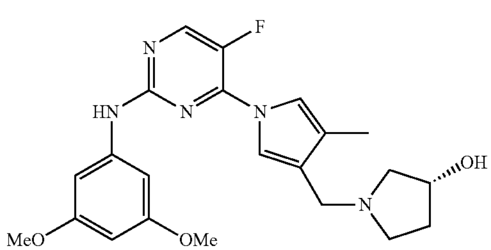 [SMILES: COc1cc(Nc2ncc(F)c(-n3cc(C)c(CN4CC[C@@H](O)C4)c3)n2)cc(OC)c1] | (R)-1-((1-(2-(3,5-dimethoxyphenyl-amino)-5-fluoropyrimidin-4-yl)-4-methyl-1H-pyrrol-3-yl)methyl)pyrrolidin-3-ol | 428 |

TABLE 3-continued

Compounds of Formula I

| Compound No. | Structure | Compound Name; NMR (300 MHz, DMSO-d6) or | MS (ESI+) m/z |
|---|---|---|---|
| 103 | 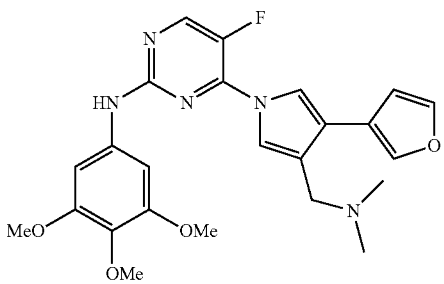 [SMILES: COc1cc(Nc2ncc(F)c(-n3cc(CN(C)C)c(-c4ccoc4)c3)n2)cc(OC)c1OC] | 4-(3-((dimethylamino)methyl)-4-(furan-3-yl)-1H-pyrrol-1-yl)-5-fluoro-N-(3,4,5-trimethoxyphenyl)pyrimidin-2-amine; 9.68 (s, 1H), 8.62 (d, J = 4.5 Hz, 1H), 7.94 (s, 1H), 7.80 (s, 1H), 7.70 (s, 1H), 7.62 (s, 1H), 7.14 (s, 2H), 6.80 (s, 1H), 3.79 (s, 6H), 3.63 (s, 3H), 3.34 (s, 2H), 2.19 (s, 6H) | 468 |
| 104 | 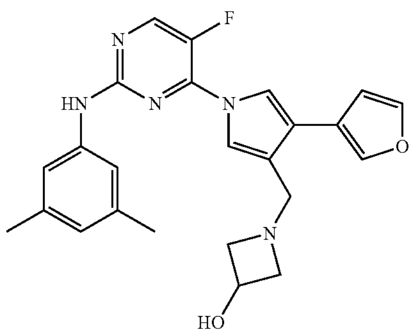 [SMILES: Cc1cc(C)cc(Nc2ncc(F)c(-n3cc(CN4CC(O)C4)c(-c4ccoc4)c3)n2)c1] | 1-((1-(2-(3,5-dimethylphenylamino)-5-fluoropyrimidin-4-yl)-4-(furan-3-yl)-1H-pyrrol-3-yl)methyl)azetidin-3-ol; 9.67 (s, 1H), 8.60 (d, J = 4.5 Hz, 1H), 7.94 (s, 1H), 7.77 (s, 1H), 7.72 (s, 1H), 7.58 (s, 1H), 7.37 (s, 2H), 6.79 (s, 1H), 6.65 (s, 1H), 5.35 (d, J = 6.0 Hz, 1H), 4.19 (q, J = 6.3 Hz, 1H), 3.57-3.58 (m, 4H), 2.85 (s, 2H), 2.28 (s, 6H) | 434 |
| 105 | 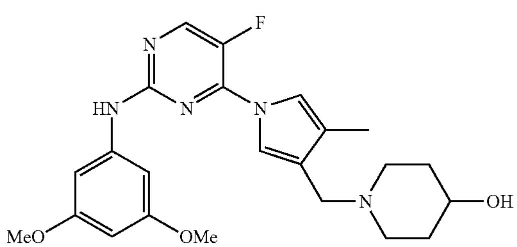 [SMILES: COc1cc(Nc2ncc(F)c(-n3cc(C)c(CN4CCC(O)CC4)c3)n2)cc(OC)c1] | 1-((1-(2-(3,5-dimethoxyphenylamino)-5-fluoropyrimidin-4-yl)-4-methyl-1H-pyrrol-3-yl)methyl)piperidin-4-ol | 442 |
| 106 | 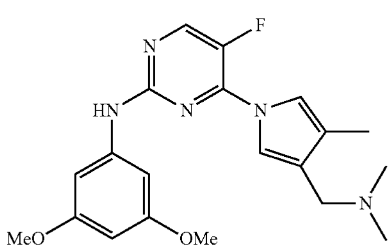 [SMILES: COc1cc(Nc2ncc(F)c(-n3cc(C)c(CN(C)C)c3)n2)cc(OC)c1] | N-(3,5-dimethoxyphenyl)-4-(3-((dimethylamino)methyl)-4-methyl-1H-pyrrol-1-yl)-5-fluoropyrimidin-2-amine | 386 |
| 107 | 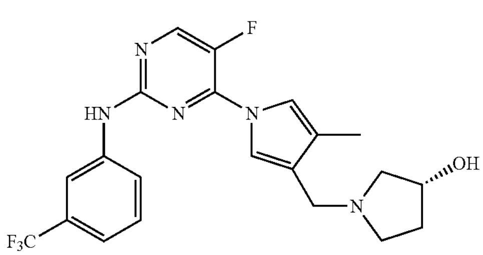 [SMILES: Cc1cn(-c2nc(Nc3cccc(C(F)(F)F)c3)ncc2F)cc1CN1CC[C@@H](O)C1] | (R)-1-((1-(5-fluoro-2-(3-(trifluoromethyl)phenylamino)pyrimidin-4-yl)-4-methyl-1H-pyrrol-3-yl)methyl)pyrrolidin-3-ol | 436 |

TABLE 3-continued

Compounds of Formula I

| Compound No. | Structure | Compound Name; NMR (300 MHz, DMSO-d6) or | MS (ESI+) m/z |
|---|---|---|---|
| 108 | 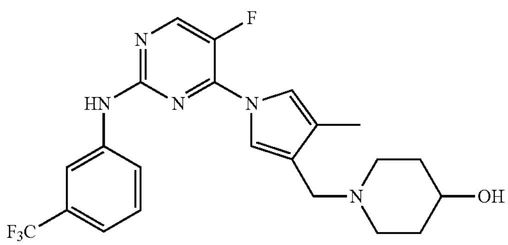 [SMILES: Cc1cn(-c2nc(Nc3cccc(C(F)(F)F)c3)ncc2F)cc1CN1CCC(O)CC1] | 1-((1-(5-fluoro-2-(3-(trifluoro-methyl)phenylamino)pyrimidin-4-yl)-4-methyl-1H-pyrrol-3-yl)methyl)piperidin-4-ol | 450 |
| 109 | 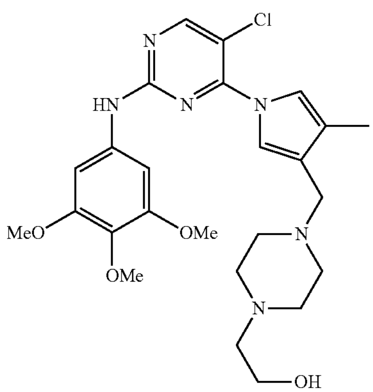 [SMILES: COc1cc(Nc2ncc(Cl)c(-n3cc(C)c(CN4CCN(CCO)CC4)c3)n2)cc(OC)c1OC] | 2-(4-((1-(5-chloro-2-(3,4,5-trimethoxyphenylamino)pyrimidin-4-yl)-4-methyl-1H-pyrrol-3-yl)methyl)piperazin-1-yl)ethanol; 9.80 (s, 1H), 8.54 (s, 1H), 7.56 (s, 1H), 7.52 (s, 1H), 7.13 (s, 2H), 3.78 (s, 9H), 3.62 (s, 2H), 3.56 (m, 2H), 3.45-3.34 (m, 6H), 3.26 (m, 4H), 2.08 (s, 3H) | 518 |
| 110 | 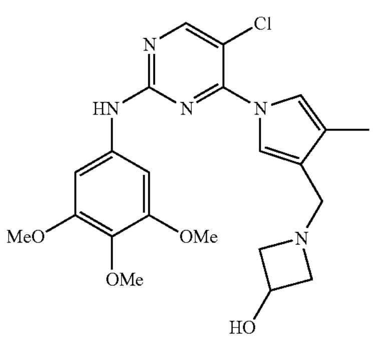 [SMILES: COc1cc(Nc2ncc(Cl)c(-n3cc(C)c(CN4CC(O)C4)c3)n2)cc(OC)c1OC] | 1-((1-(5-chloro-2-(3,4,5-trimethoxyphenylamino)pyrimidin-4-yl)-4-methyl-1H-pyrrol-3-yl)methyl)azetidin-3-ol; 9.85 (s, 1H), 8.58 (s, 1H), 7.70 (s, 1H), 7.51 (s, 1H), 7.13(s, 2H), 3.78 (s, 9H), 3.62 (s, 2H), 3.55-3.50 (m, 1H), 3.27-3.23 (m, 4H), 2.04 (s, 3H) | 460 |
| 111 | 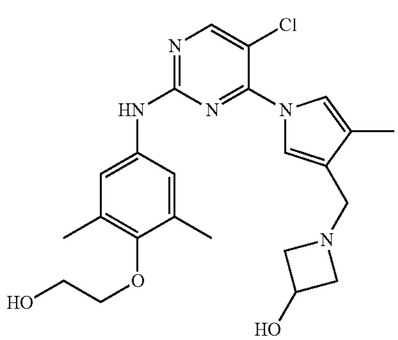 [SMILES: Cc1cn(-c2nc(Nc3cc(C)c(OCCO)c(C)c3)ncc2Cl)cc1CN1CC(O)C1] | 1-((1-(5-chloro-2-(4-(2-hydroxyethoxy)-3,5-dimethylphenylamino)pyrimidin-4-yl)-4-methyl-1H-pyrrol-3-yl)methyl)azetidin-3-ol; 9.68 (s, 1H), 8.51 (s, 1H), 7.55 (s, 1H), 7.48 (s, 1H), 7.33 (s, 2H), 5.41 (s, 1H), 4.86 (s, 1H), 4.22 (m, 1H), 3.74 (t, J = 3.9 Hz, 2H), 3.70 (s, 2H), 3.61 (t, J = 3.9 Hz,, 2H), 3.51 (s, 2H), 2.89 (s, 1H), 2.23 (s, 6H), 2.02 (s, 3H) | 358 |

TABLE 3-continued

Compounds of Formula I

| Compound No. | Structure | Compound Name; NMR (300 MHz, DMSO-d6) or | MS (ESI+) m/z |
|---|---|---|---|
| 112 | 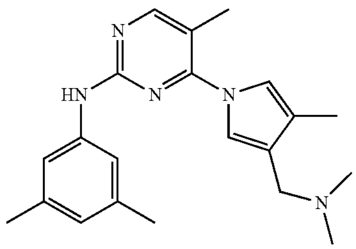 | 4-(3-((dimethylamino)methyl)-4-methyl-1H-pyrrol-1-yl)-N-(3,5-dimethylphenyl)-5-methylpyrimidin-2-amine | 350 |
| 113 | 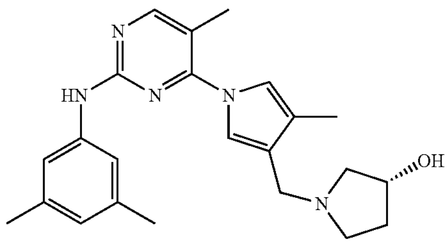 [SMILES: Cc1cc(C)cc(Nc2ncc(C)c(-n3cc(C)c(CN4CC[C@@H](O)C4)c3)n2)c1] | 4-(3-((dimethylamino)methyl)-4-methyl-1H-pyrrol-1-yl)-N-(3,5-dimethylphenyl)-5-methylpyrimidin-2-amine | 392 |
| 114 | 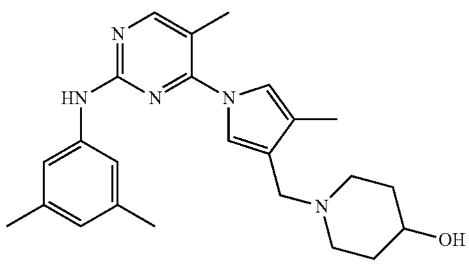 [SMILES: Cc1cc(C)cc(Nc2ncc(C)c(-n3cc(C)c(CN4CCC(O)CC4)c3)n2)c1] | 1-((1-(2-(3,5-dimethylphenylamino)-5-methylpyrimidin-4-yl)-4-methyl-1H-pyrrol-3-yl)methyl)piperidin-4-ol | 406 |
| 115 | 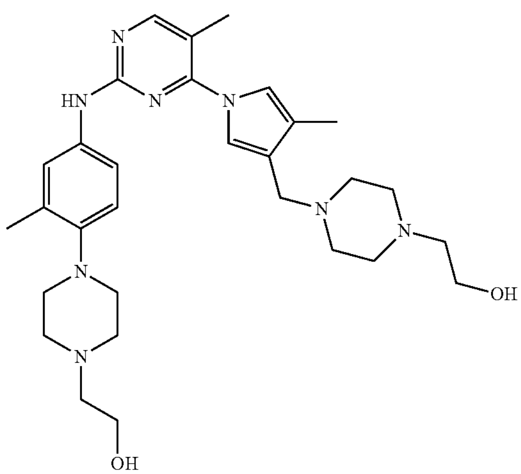 [SMILES: Cc1cn(-c2nc(Nc3ccc(N4CCN(CCO)CC4)c(C)c3)ncc2C)cc1CN1CCN(CCO)CC1] | 2-(4-((1-(2-(4-(4-(2-hydroxyethyl)piperazin-1-yl)-3-methylphenyl-amino)-5-methylpyrimidin-4-yl)-4-methyl-1H-pyrrol-3-yl)methyl)piperazin-1-yl)ethanol | 548 |
| 116 | 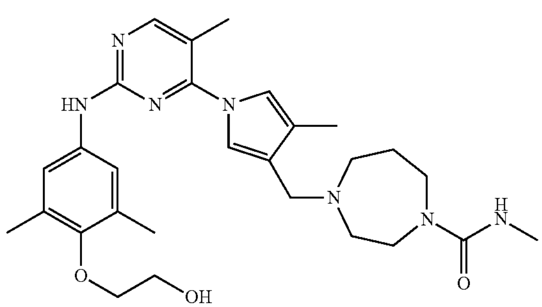 | 4-((1-(2-(4-(2-hydroxyethoxy)-3,5-dimethylphenylamino)-5-methyl-pyrimidin-4-yl)-4-methyl-1H-pyrrol-3-yl)methyl)-N-methyl-1,4-diazepane-1-carboxamide | 522 |

TABLE 3-continued

Compounds of Formula I

| Compound No. | Structure | Compound Name; NMR (300 MHz, DMSO-d6) or | MS (ESI+) m/z |
|---|---|---|---|
| 117 | 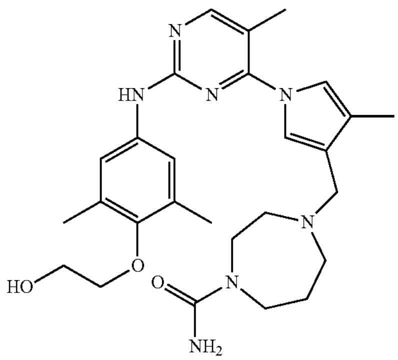 [SMILES: Cc1cn(-c2nc(Nc3cc(C)c(OCCO)c(C)c3)ncc2C)cc1CN1CCCN(C(N)=O)CC1] | 4-((1-(2-(4-(2-hydroxyethoxy)-3,5-dimethylphenylamino)-5-methylpyrimidin-4-yl)-4-methyl-1H-pyrrol-3-yl)methyl)-1,4-diazepane-1-carboxamide; 9.30 (s, 1H), 8.31 (s, 1H), 7.38 (s, 3H), 7.28 (s, 1H), 5.73 (d, J = 6.3 Hz, 2H), 4.86 (t, J = 5.7 Hz, 2H), 3.72-3.73 (m, 8H), 2.58-2.50 (m, 2H), 2.32 (s, 3H), 2.22 (s, 6H), 2.06 (s, 3H), 1.74-1.65 (m, 2H) | 508 |
| 118 | 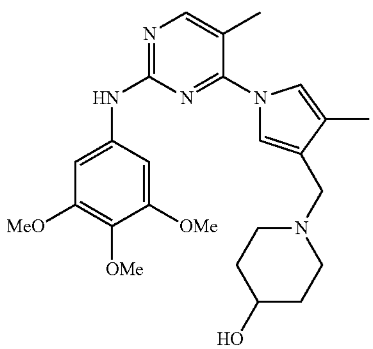 [SMILES: COc1cc(Nc2ncc(C)c(-n3cc(C)c(CN4CCC(O)CC4)c3)n2)cc(OC)c1OC] | 1-((4-methyl-1-(5-methyl-2-(3,4,5-trimethoxyphenylamino)pyrimidin-4-yl)-1H-pyrrol-3-yl)methyl) piperidin-4-ol | 468 |
| 119 | 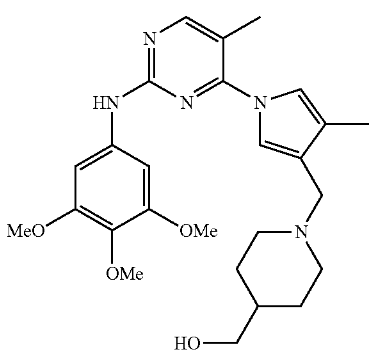 [SMILES: COc1cc(Nc2ncc(C)c(-n3cc(C)c(CN4CCC(CO)CC4)c3)n2)cc(OC)c1OC] | (1-((4-methyl-1-(5-methyl-2-(3,4,5-trimethoxyphenylamino)pyrimidin-4-yl)-1H-pyrrol-3-yl)methyl)piperidin-4-yl)methanol; 9.44 (s, 1H), 8.35 (s, 1H), 7.38 (s, 1H), 7.31 (s, 1H), 7.19 (s, 2H), 4.40 (d, J = 4.8 Hz, 1H), 3.78 (s, 6H), 3.61 (s, 3H), 3.35-3.31 (m, 4H), 3.25 (t, J = 5.4 Hz, 2H), 2.92-2.83 (m, 2H), 2.33 (s, 3H), 2.04 (s, 3H), 1.65-1.60 (m, 2H), 1.34 (m, 1H). 1.16-1.08 (m, 2H) | 482 |
| 120 | 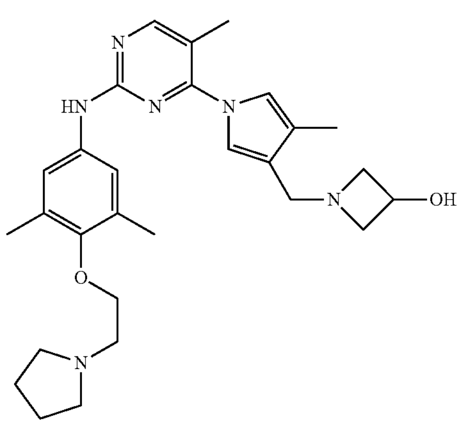 [SMILES: Cc1cn(-c2nc(Nc3cc(C)c(OCCN4CCCC4)c(C)c3)ncc2C)cc1CN1CC(O)C1] | 1-((1-(2-(3,5-dimethyl-4-(2-(pyrrolidin-1-yl)ethoxy)phenyl-amino)-5-methylpyrimidin-4-yl)-4-methyl-1H-pyrrol-3-yl)methyl) azetidin-3-ol | 491 |

TABLE 3-continued

Compounds of Formula I

| Compound No. | Structure | Compound Name; NMR (300 MHz, DMSO-d6) or | MS (ESI+) m/z |
|---|---|---|---|
| 121 | 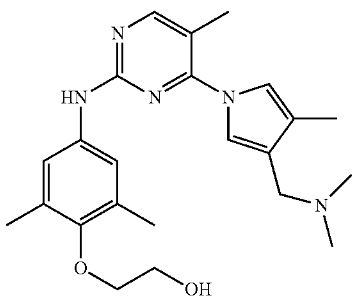 | 2-(4-(4-(3-((dimethylamino)methyl)-4-methyl-1H-pyrrol-1-yl)-5-methylpyrimidin-2-ylamino)-2,6-dimethylphenoxy)ethanol; 9.74 (s, 1H), 9.40 (s, 1H), 8.39 (s, 1H), 7.67 (s, 1H), 7.36 (s, 2H), 4.14 (t, J = 4.8 Hz, 2H), 3.73 (s, 2H), 2.76-2.74 (d, J = 4.8 Hz, 2H), 2.38-2.32 (m, 6H), 2.19 (s, 3H), 2.16 (s, 6H), 2.03 (s, 3H) | 410 |
| 122 | 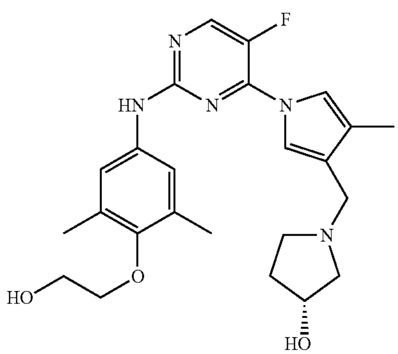 [SMILES: Cc1cn(-c2nc(Nc3cc(C)c(OCCO)c(C)c3)ncc2F)cc1CN1CC[C@@H](O)C1] | (R)-1-((1-(5-fluoro-2-(4-(2-hydroxyethoxy)-3,5-dimethylphenylamino)pyrimidin-4-yl)-4-methyl-1H-pyrrol-3-yl)methyl)pyrrolidin-3-ol; 9.49 (s, 1H), 8.52 (d, J = 4.5 Hz, 1H), 7.47 (s, 1H), 7.34 (three s, 3H), 4.86 (br s, 1H), 4.70-4.68 (m, 1H), 4.20 (br s, 1H), 3.74-3.68 (m, 6H), 3.28-3.25 (m, 2H), 2.73-2.68 (m, 2H), 2.23 (s, 6H), 2.05 (s, 3H), 2.01-1.98 (m, 1H), 1.57 (s, 1H) | 456 |
| 123 | 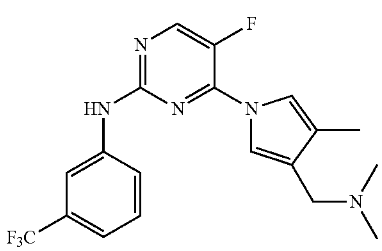 [SMILES: Cc1cn(-c2nc(Nc3cccc(C(F)(F)F)c3)ncc2F)cc1CN(C)C] | 4-(3-((dimethylamino)methyl)-4-methyl-1H-pyrrol-1-yl)-5-fluoro-N-(3-trifluoromethyl)phenyl)pyrimidin-2-amine | 394 |
| 124 | 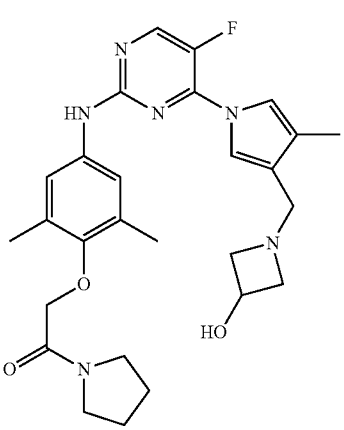 | 2-(4-(5-fluoro-4-(3-((3-hydroxyazetidin-1-yl)methyl)-4-methyl-1H-pyrrol-1-yl)pyrimidin-2-ylamino)-2,6-dimethylphenoxy)-1-(pyrrolidin-1-yl)ethanone; 9.51 (s, 1H), 8.52 (d, J = 4.5 Hz, 1H), 7.43 (s, 1H), 7.35 (s, 3H), 5.32 (br s, 1H), 4.36 (s, 2H), 4.19 (br s, 1H), 3.51-3.55 (m, 4H), 2.74-2.79 (m, 2H), 2.23 (s, 6H), 2.18-2.19 (m, 2H), 2.02 (s, 3H), 1.73-1.92 (m, 4H) | 509 |

TABLE 3-continued

Compounds of Formula I

| Compound No. | Structure | Compound Name; NMR (300 MHz, DMSO-d6) or | MS (ESI+) m/z |
|---|---|---|---|
| 125 | 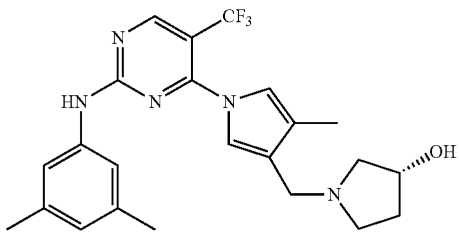 | (R)-1-((1-(2-(3,5-dimethylphenyl-amino)-5-(trifluoromethyl)pyrimidin-4-yl)-4-methyl-1H-pyrrol-3-yl)methyl)pyrrolidin-3-ol | 446 |
| 126 | 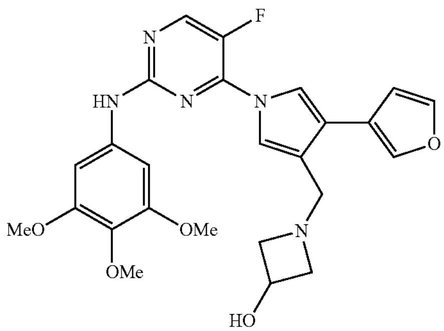 [SMILES: COc1cc(Nc2ncc(F)c(-n3cc(CN4CC(O)C4)c(-c4ccoc4)c3)n2)cc(OC)c1OC] | 1-((1-(5-fluoro-2-(3,4,5-trimethoxy-phenylamino)pyrimidin-4-yl)-4-(furan-3-yl)-1H-pyrrol-3-yl)methyl)azetidin-3-ol | 496 |
| 127 | 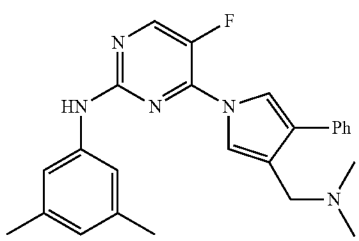 | 4-(3-((dimethylamino)methyl)-4-phenyl-1H-pyrrol-1-yl)-N-(3,5-dimethylphenyl)-5-fluoropyrimidin-2-amine | 416 |
| 128 | 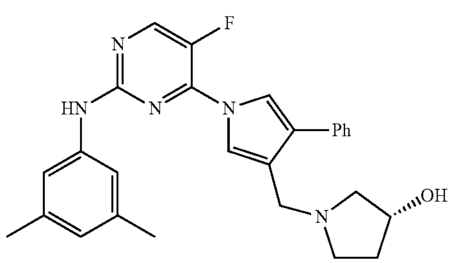 [SMILES: Cc1cc(C)cc(Nc2ncc(F)c(-n3cc(CN4CC[C@@H](O)C4)c(-c4ccccc4)c3)n2)c1] | (R)-1-((1-(2-(3,5-dimethylphenyl-amino)-5-fluoropyrimidin-4-yl)-4-phenyl-1H-pyrrol-3-yl)methyl)pyrrolidin-3-ol | 458 |
| 129 | 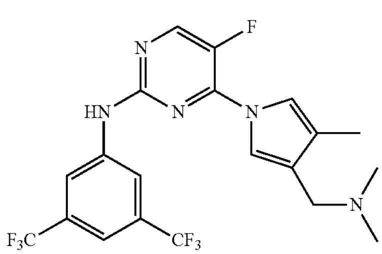 [SMILES: Cc1cn(-c2nc(Nc3cc(C(F)(F)F)cc(C(F)(F)F)c3)ncc2F)cc1CN(C)C] | N-(3,5-bis(trifluoromethyl)phenyl)-4-(3-((dimethylamino)methyl)-4-methyl-1H-pyrrol-1-yl)-5-fluoro-pyrimidin-2-amine | 462 |

TABLE 3-continued

Compounds of Formula I

| Compound No. | Structure | Compound Name; NMR (300 MHz, DMSO-d6) or | MS (ESI+) m/z |
|---|---|---|---|
| 130 | 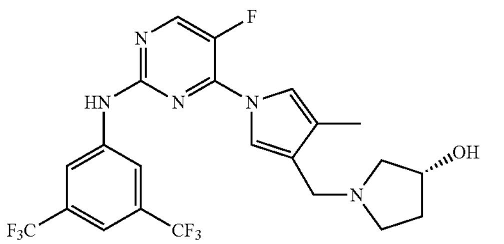 [SMILES: Cc1cn(-c2nc(Nc3cc(C(F)(F)F)cc(C(F)(F)F)c3)ncc2F)cc1CN1CC[C@@H](O)C1] | (R)-1-((1-(2-(3,5-bis(trifluoromethyl)phenylamino)-5-fluoropyrimidin-4-yl)-4-methyl-1H-pyrrol-3-yl)methyl)pyrrolidin-3-ol | 504 |
| 131 | 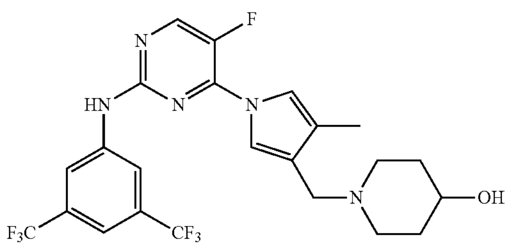 | 1-((1-(2-(3,5-bis(trifluoromethyl)phenylamino)-5-fluoropyrimidin-4-yl)-4-methyl-1H-pyrrol-3-yl)methyl)piperidin-4-ol | 518 |
| 132 | 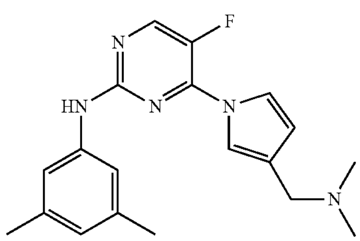 | 4-(3-((dimethylamino)methyl)-1H-pyrrol-1-yl)-N-(3,5-dimethylphenyl)-5-fluoropyrimidin-2-amine | 340 |
| 133 | 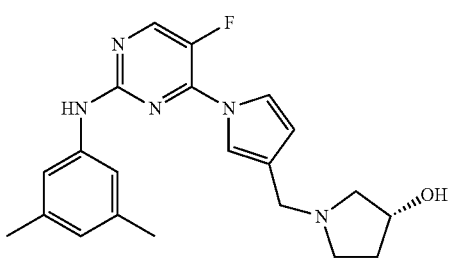 [SMILES: Cc1cc(C)cc(Nc2ncc(F)c(-n3ccc(CN4CC[C@@H](O)C4)c3)n2)c1] | (R)-1-((1-(2-(3,5-dimethylphenylamino)-5-fluoropyrimidin-4-yl)-1H-pyrrol-3-yl)methyl)pyrrolidin-3-ol | 382 |
| 134 | 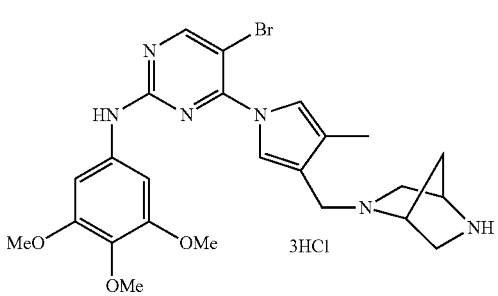 [SMILES: COc1cc(Nc2ncc(Br)c(-n3cc(C)c(CN4CC5CC4CN5)c3)n2)cc(OC)c1OC] | 4-(3-(2,5-diazabicyclo[2.2.1]heptan-2-ylmethyl)-4-methyl-1H-pyrrol-1-yl)-5-bromo-N-(3,4,5-trimethoxyphenyl)pyrimidin-2-amine trihydrochloride | 529 |

TABLE 3-continued

Compounds of Formula I

| Compound No. | Structure | Compound Name; NMR (300 MHz, DMSO-d6) or | MS (ESI+) m/z |
|---|---|---|---|
| 135 | 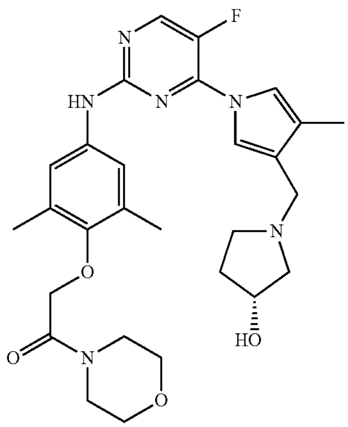 | (R)-2-(4-(5-fluoro-4-(3-((3-hydroxy-pyrrolidin-1-yl)methyl)-4-methyl-1H-pyrrol-1-yl)pyrimidin-2-yl amino)-2,6-dimethylphenoxy)-1-morpholinoethanone | 539 |
| 136 | 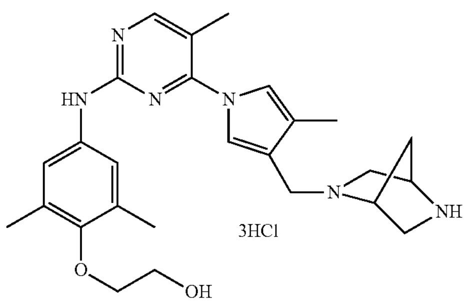 [SMILES: Cc1cn(-c2nc(Nc3cc(C)c(OCCO)c(C)c3)ncc2C)cc1CN1CC2CC1CN2] | 2-(4-(4-(3-(2,5-diazabicyclo[2.2.1]heptan-2-ylmethyl)-4-methyl-1H-pyrrol-1-yl)-5-methylpyrimidin-2-ylamino)-2,6-dimethylphenoxy)ethanol trihydrochloride | 463 |
| 137 | 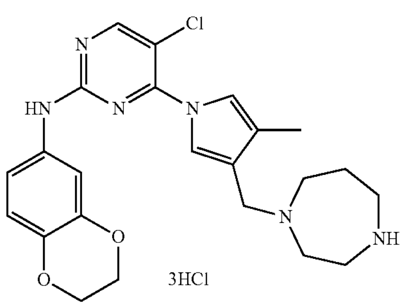 [SMILES: Cc1cn(-c2nc(Nc3ccc4c(c3)OCCO4)ncc2Cl)cc1CN1CCCNCC1] | 4-(3-((1,4-diazepan-1-yl)methyl)-4-methyl-1H-pyrrol-1-yl)-5-chloro-N-(2,3-dihydrobenzo[b][1,4]dioxin-6-yl)pyrimidin-2-amine | 455 |
| 138 | 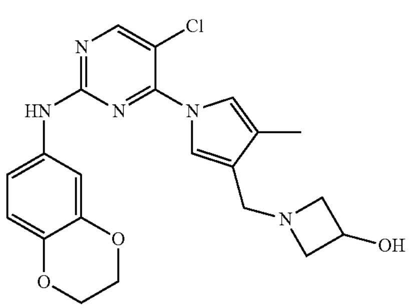 [SMILES: Cc1cn(-c2nc(Nc3ccc4c(c3)OCCO4)ncc2Cl)cc1CN1CC(O)C1] | 1-((1-(5-chloro-2-(2,3-dihydrobenzo[b][1,4]dioxin-6-ylamino)pyrimidin-4-yl)-4-methyl-1H-pyrrol-3-yl)methyl)azetidin-3-ol | 428 |

TABLE 3-continued

Compounds of Formula I

| Compound No. | Structure | Compound Name; NMR (300 MHz, DMSO-d6) or | MS (ESI+) m/z |
|---|---|---|---|
| 139 | 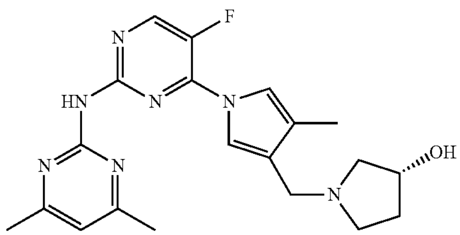 [SMILES: Cc1cc(C)nc(Nc2ncc(F)c(-n3cc(C)c(CN4CC[C@@H](O)C4)c3)n2)n1] | (R)-1-((1-(2-(4,6-dimethylpyrimidin-2-ylamino)-5-fluoropyrimidin)-4-yl)-4-methyl-1H-pyrrol-3-yl)methyl)pyrrolidin-3-ol | 398 |

BIOLOGICAL ASSAYS

1. Kinase Inhibition Assay

Compounds of the present invention were tested for their capacity to inhibit a kinase panel which includes, but are not limited to, spleen tyrosine kinase (SYK), zeta-chain-associated protein kinase 70 (ZAP70), PTK2B protein tyrosine kinase 2 (PYK2), focal adhesion kinase (FAK), provirus integration of maloney kinase 1 (PIM1), rearranged during transfection kinase (RET), Fms-like tyrosine kinase 3 (FLT3), Janus kinase 2 (JAK2), and leucine-rich repeat kinase 2 (LRRK2).

FLT3 is a member of the type III receptor tyrosine kinase (RTK) family. The ligand for FLT3 is expressed by the marrow stromal cells and other cells and synergizes with other growth factors to stimulate proliferation of stem cells, progenitor cells, dendritic cells, and natural killer cells. FLT3 has been implicated in hematopoietic disorders which are pre-malignant disorders including myeloproliferative disorders, such as thrombocythemia, essential thrombocytosis (ET), angiogenic myeloid metaplasia, myelofibrosis (MF), myelofibrosis with myeloid metaplasia (MMM), chronic idiopathic myelofibrosis (IMF), and polycythemia vera (PV), the cytopenias, and pre-malignant myelodysplastic syndromes. Hematological malignancies include leukemias, lymphomas (non-Hodgkin's lymphoma), Hodgkin's disease (also called Hodgkin's lymphoma), and myeloma-for instance, acute lymphocytic leukemia (ALL), acute myeloid leukemia (AML), acute promyelocytic leukemia (APL), chronic lymphocytic leukemia (CLL), chronic myeloid leukemia (CML), chronic neutrophilic leukemia (CNL), acute undifferentiated leukemia (AUL), anaplastic large-cell lymphoma (ALCL), prolymphocytic leukemia (PML), juvenile myelomonocyctic leukemia (JMML), adult T-cell ALL, AML with trilineage myelodysplasia (AML/TMDS), mixed lineage leukemia (MLL), myelodysplastic syndromes (MDSs), myeloproliferative disorders (MPD), multiple myeloma, (MM) and myeloid sarcoma.

RET is the receptor for members of the glial cell line derived neurotrophic factor (GDNF) family of extracellular signalling molecules (GFL's). RET signal transduction is central to the development of normal kidneys and the enteric nervous system. RET loss of function mutations are associated with the development of Hirschsprung's disease, while gain of function mutaions are associated with development of various types of cancer, including medullar thyroid carcinoma and multiple endocrine neoplasias type II and III.

Spleen tyrosine kinase (SYK) is a member of the SYK family of tyrosines kinases which are non-receptor cytoplasmic tyrosine kinases sharing a characteristic dual SH2 domain separated by a linker domain. SYK plays a role in transmitting signals from a variety of cell surface receptors including CD74, Fc Receptor, and integrins. Abnormal function of SYK has been implicated in instances of hematopoeitic malignancies. Several transforming viruses, such as Epstein Barr virus, bovine leukemia virus, and mouse mammary tumor virus, are known to contain "Immunoreceptor Tyrosine Activation Motifs" (ITAMs) that lead to activation of SYK.

ZAP70 is an enzyme that belongs to the protein tyrosine kinase family, and it plays a role in thymocyte development, T-cell development, and lymphocyte activation. ZAP70 is phosphorylated on tyrosine residues upon T-cell antigen receptor (TCR) stimulation and functions in the initial step of TCR-mediated signal transduction in combination with the Src family kinases, Lck and Fyn. Mutations in this gene cause selective T-cell defect, a severe combined immunodeficiency disease characterized by a selective absence of CD8-positive T-cells.

PYK2 is a cytoplasmic protein tyrosine kinase involved in calcium-induced regulation of ion channels and activation of the map kinase signaling pathway. The encoded protein may represent an important signaling intermediate between neuropeptide-activated receptors or neurotransmitters that increase calcium flux and the downstream signals that regulate neuronal activity. The encoded protein undergoes rapid tyrosine phosphorylation and activation in response to increases in the intracellular calcium concentration, nicotinic acetylcholine receptor activation, membrane depolarization, or protein kinase C activation. Its activation is highly correlated with the stimulation of c-Jun N-terminal kinase activity. PYK2 is implicated in diseases such as osteoporesis, arthritis, myeloid leukemia, hypo-osmolality, sarcoma, blast crisis, glioma, erythroleukemia, and cancer.

FAK (encoded by the gene PTK2) is a non-receptor tyrosine kinase that integrates signals from integrins and growth factor receptor. FAK plays a role in the regulation of cell survival, growth, spreading, migration and invasion and is regulated and activated by phosphorylation on multiple tyrosine residues. Overexpression of FAK mRNA and/or protein has been implicated in cancers of the breast, colon, thyroid, and prostate. Phosphorylation of FAK is increased in malignant tissues.

JAK1 is a member of the protein-tyrosine kinase (PTK) family and characterized by the presence of a second phosphotransferase-related domain immediately N-terminal to the PTK domain. JAK1 is involved in the interferon-alpha/beta and -gamma signal transduction pathways. The reciprocal interdependence between JAK1 and TYK2 activities in the interferon-alpha pathway, and between JAK1 and JAK2 in the interferon-gamma pathway may reflect a requirement for these kinases in the correct assembly of interferon receptor complexes.

JAK2 has been implicated in signaling by members of the type II cytokine receptor family (e.g. interferon receptors), the GM-CSF receptor family (IL-3R, IL-5R and GM-CSF-R), the gp130 receptor family (e.g. IL-6R), and the single chain receptors (e.g. Epo-R, Tpo-R, GH-R, PRL-R). JAK2 gene fusions with the TEL(ETV6) (TEL-JAK2) and PCM1 genes have been associated with leukemia. Further, mutations in JAK2 have been implicated in polycythemia vera, essential thrombocythemia, and other myeloproliferative disorders. This mutation, a change of valine to phenylalanine at the 617 position, renderd hematopoietic cells more sensitive to growth factors such as erythropoietin and thrombopoietin.

JAK3 is a tyrosine kinase of the Janus family. JAK3 is predominantly expressed in immune cells and transduces a signal in response to activation via tyrosine phosphorylation by interleukin receptors. Mutations that abrogate JAK 3 function cause an autosomal severe combined immunodeficiency disease (SCID). Mice that do not express JAK3 have T-cells and B-cells that fail to respond to various cytokines. Since JAK3 expression is restricted mostly to hematopoietic cells, its role in cytokine signaling is thought to be more restricted than other JAKs. JAK3 is involved in signal transduction by receptors that employ the common gamma chain (γC) of the type I cytokine receptor family (e.g. IL-2R, IL-4R, IL-7R, IL-9R, IL-15R, and IL-21R).

Provirus Integration of Maloney Kinase (PIM-Kinase) was identified as one of the frequent proto-oncogenes capable of being transcriptionally activated by Maloney retrovirus integration event in mice, causing lymphomas in affected mice. PIM 1, 2 and 3 are serine/threonine kinases normally function in survival and proliferation of hematopoietic cells in response to growth factors and cytokines. Transgenic mice overexpressing PIM1 or PIM2 show increased incidence of T-cell lymphomas, while overexpression in conjunction with c-myc is associated with incidence of B-cell. Aberrent PIM expression has been reported in many human malignancies including prostate cancer, hepatocellular carcinoma, and pancreatic cancer. PIM kinases are involved in the early differentiation process of Helper T-cells, which coordinate the immunological response in autoimmune diseases, allergic reaction and tissue transplant rejection. In addition to a potential role in cancer treatment and myeloproliferative diseases, an inhibitor of PIM can be useful to control expansion of immune cells in other pathologic condition such as autoimmune diseases, allergic reactions and in organ transplantation rejection syndroms.

Methods
Inhibition of SYK, ZAP70, PYK2, FAK, PIM1, RET, FLT3, JAK2 and LRRK2 Kinase Activity Compounds of the invention were initially diluted to 10 mM in 100% DMSO (CALBIOCHEM™) for storage and made into kinase buffer solution to create a compound concentration ranging from 1 uM and 10 uM. Serial dilutions of compounds of the invention were dispensed into a 96-well plate (GREINER BIOSCIENCES™) at 6 µL each. Purified full-length human SYK, ZAP70, PIM1, PYK2 and truncated human FAK, RET, FLT3, JAK2, and LRRK2 (CARNA BIOSCIENCES™) were diluted in kinase buffer and added to the compound solutions and pre-incubated for 30 minutes at room temperature (1 hour for PYK2). Next, ATP (TEKNOVA™) and substrate solution (suggested manufacture substrates of PerkinElmer™, for example, Ulight™-TK peptide for SYK, Ulight™-PolyGT for ZAP70, FAK, and PYK2, and Ulight™-CREBtide for PIM1 (PERKINELMER™)) was added (12 uL each) to the wells containing the compound solution and enzyme. The reaction mixture was incubated for 1 hour (2 hours for PYK2). Following the incubation, the stop solution made with EDTA, water, and Lance detection buffer (PERKINELMER™) was added (12µL each) to stop phosphorylation. Following the addition of the stop solution and 5 minutes of shaking, the detection solution containing the Europium-labeled antibody (suggested manufacture substrates of PerkinElmer™, for example, PT66 for SYK, ZAP70, PYK2, and FAK, and Anti-Creb for PIM1), water, and Lance detection buffer was added (12 µL each) to the reaction mixture and incubated again for 50 minutes. Substrate phosphorylation was a function of the 665 nm emission measured following the addition of the detection solution and 50 minutes of incubation. The IC50 value of test compound was calculated at Gradpad Prism 5 unless specified otherwise.

Results

Compounds of Formula (I) exhibited useful pharmacological properties. As used herein, zero % inhibition indicates no inhibition on the kinase activity (e.g., as seen in control treated with no inhibitor), whereas 100% inhibition indicates complete inhibition of the kinase activity.

Compounds of Formula (I) exhibited various levels of inhibition of the protein kinases on the panel. Certain compounds exhibited percentage inhibition of greater than 80% against one or more of the kinase at 1 µM concentration as shown in Table 2.

For example, Compound 21 of Formula (I), namely, (4-methyl-1-(5-methyl-2-(3,4,5-trimethoxyphenylamino)pyrimidin-4-yl)-1H-pyrrol-3-yl)methanol, was shown to inhibit the kinase activity of SYK (96.4%), Zap70 (54.6%), PYK2 (78.2%), FAK (70.7%) and PIM1 (71.2%), LRRK2 (93%) at a concentration of 1 µM and that of FLT3 (IC50, 1.9 nM), RET (IC50, 50 nM), K1T (137 nM) and JAK2 (IC50 7.7 nM; see Table 2). Table 2 illustrates the percentage/molar inhibition of SYK, ZAP70, PYK2, FAK, PIM1, RET, FLT3, JAK2 and LRRK2 by the representative compounds of Formula (I). Two known kinase inhibitors, R406 and staurosporine, were used as positive controls.

TABLE 2

Inhibition of Various Kinases

| Compound no. | SYK | ZAP70 | PYK2 | FAK | PIM1 |
|---|---|---|---|---|---|
| 14 | 82.7% | 41.3% | 30.6% | 36.9% | 21.9% |
| 16 | 80.7% | 31.9% | 84.9% | 34.1% | n.d. |
| 21 | 96.4% | 54.6% | 78.2% | 70.7% | 71.2% |
| 38 | 41.8% | 19.3% | 18% | 17.7% | 3.7% |
| 41 | 99.3% | n.d. | 30.7% | 13.9% | n.d. |
| 46 | 5.9 nM | n.d. | n.d. | n.d. | n.d. |
| 52 | 3.5 nM | n.d. | n.d. | n.d. | n.d. |
| R406 | 96.8% | 58.5% | 74.3% | 46.5% | n.d. |

| | RET | FLT3 | JAK2 | LRRK2 |
|---|---|---|---|---|
| 21 | 50 nM | 1.9 nM | 7.7 nM | 93% |
| 24 | 40.4 nM | 6.8 nM | 1.6 nM | n.d. |
| 29 | 42% | 53% | n.d. | 31.4% |
| 32 | 51.3 nM | n.d. | 40% | 44.3% |
| 40 | 10.2 nM | 0.17 nM | 3.7 nM | 275 nM |
| 91 | 5.2 nM | 0.4 nM | 36.5 nM | 424.1 nM |
| 93 | 76.1 nM | 11.7 nM | 219.3 nM | n.d. |
| 96 | 10.1 nM | 0.53 nM | 3.9 nM | n.d. |
| 97 | 35.8 nM | 3.6 nM | 65.1 nM | n.d. |
| 121 | 2.3 nM | 1.7 nM | 2.5 nM | n.d. |
| Staurosporine | 2.2 nM | 0.2 nM | 0.3 nM | 7.8 nM |

* n.d., not determined

2. Tumor Necrosis Factor (TNF)-α Release Assay

Compounds of the present invention are tested for their effects on TNF-α release in human acute monocytic leukimia cell line (THP-1) to illustrate potential efficacy at the cellular level. TNF-α is a cytokine involved in systemic inflammation and is a member of a group of cytokines that stimulate the acute phase reaction. The primary role of TNF-α is in the regulation of immune cells. TNF-α is known to induce apoptotic cell death and inflammation and to inhibit early tumorigenesis and viral replication. Dysregulation and, in particular, overproduction of TNF-α have been implicated in a variety of human diseases, autoimmune disease, inflammation, arthritis and cancer.

Production or release of TNF-α is controlled by type of stimulus to which the cell responds. SYK activity is involved in mediating TNF-α production. When stimulated by IgG, cells increase TNF-α production in a SYK dependent manner (i.e., the SYK dependent pathway). However, when stimulated by lipopolysaccharide (LPS), they produce TNF-α in a SYK independent manner.

Methods

Compounds of the invention were tested for their TNF-α release effect on THP-1 cells. For SYK dependent TNF-α release assay (i.e., via IgG stimulation), THP-1 cells derived from human monocytic cells were obtained from the American Type Culture Collection (ATCC, Manassas, Va.). This cell line was maintained with an Roswell Park Memorial Institute (RPMI) medium (GIBCO™) containing 10 fetal bovine serum (FBS; GIBCO™) and 0.05 mM 2-mercaptoethanol. The THP-1 cells were seeded at $1 \times 10^5$ cells/100 μL/well into human IgG (10 μg/well, INVITROGENT™)-coated 96 well culture plate, and serially diluted compound was then added. After an 18-hour incubation period at 37° C., supernatants were collected for the determination of the TNF-α level by enzyme-linked immunosorbent assay (ELISA), and the remaining cells were subjected to an MTT (yellow tetrazolium salt) assay to determine the cytotoxic effects of compound.

For SYK independent TNF-α release assay (i.e., via lipopolysaccharide (LPS)-stimulation), THP-1 cells derived from human monocytic cells were obtained from the American Type Culture Collection (ATCC, Manassas, Va.). This cell line was maintained with an RPMI medium (GIBCO™) containing 10 fetal bovine serum (FBS, GIBCO™) and 0.05 mM 2-mercaptoethanol. The THP-1 cells were seeded at $1 \times 10^5$ cells/100 μL/well into 96-well culture plates, and treated with lipopolysaccharide (1 μg/ml), and serially diluted compound was then added. After an 18-hour incubation period at 37° C., supernatants were collected for the determination of the TNF-α level by ELISA, and the remaining cells were subjected to an MTT assay to determine the cytotoxic effects.

Results

Compounds of Formula (I) exhibited useful pharmacological properties. As used herein, control used without the presence of an inhibitor indicates zero inhibition of TNF-α release.

Certain compounds of Formula (I) exhibited a percentage inhibition of greater than 50% at 0.3 μM concentration in a SYK dependent manner (e.g., IgG stimulation). Specifically, at 0.3 μM concentration, Compounds Nos. 82, 132, and 133 of the present invention exhibited a percentage inhibition greater that those exhibited by R406, a widely known kinase inhibitor, in SYK dependent TNF-α release assay (i.e., IgG stimulated release).

For example, Compound No. 133 of Formula (I), (R)-1-(1-(2-(3,5-dimethylphenylamino)-5-fluoropyrimidin-4-yl)-1H-pyrrol-3-yl)methyl)pyrrolidin-3-ol, showed a greater percentage inhibition of TNF-α release at a concentration of 0.3 μM as compared with those exhibited by R406. The percentage inhibition data of the representative compounds of Formula (I) of the present invention is shown in Table 3.

TABLE 3

| | TNF-α Release Inhibition | | | |
|---|---|---|---|---|
| | IgG stimulation | | LPS stimulation | |
| Compound no. | At 0.3 μM | At 1 μM | At 0.3 μM | At 1 μM |
| 77 | 35.3% | 69.5% | 42.2% | 36.0% |
| 80 | 51.5% | 91.1% | 8.2% | 12.5% |
| 82 | 49.2% | 91.4% | 18.1% | 21.5% |
| 132 | 85.9% | 94.5% | 3.1% | 8.2% |
| 133 | 86.3% | 99.4% | 13.8% | 14.2% |
| R406 | 49.9% | 87.4% | n.d. | n.d. |
| Dexamethasone | n.d. | n.d. | n.d. | 68.4% |

3. Cell Viability Assay: RET Inhibition

Compounds of the invention were tested for their effects on cell viability in various human cancer cell lines such as MTC-TT to illustrate efficacy of the invention.

The RET proto-oncogene encodes a receptor tyrosine kinase for members of the glial cell line-derived neurotrophic factor family of extracellular signaling molecules. RET loss of function mutations are associated with Hirschsprung's disease, while gain of function mutations are implicated in the development of various types of human cancer, including medullary thyroid carcinoma, multiple endocrine neoplasias type 2A (MEN2A) and 2B (MEN2B), phaeochromocytoma and parathyroid hyperplasia.

Methods

To address RET dependent cell viability, the medullary thyroid carcinoma cell line, MTC-TT representing MEN2A was utilized to test compounds of the present invention. MTC-TT were cultured at RPMI containing 15 bovine calf serum (Hyclon™ of Thermo™) and supplemented with 2 mM L-Glutamine The cells were grown at a density of $5 \times 10^4$ cells/100 μL/well in duplicate in 96-well plates for one day and treated with different concentrations of test compound. Cell viability for MTC-TT two days after drug treatment was measured by Cell Titer 96 Aqueous One Solution Reagent (Promega™) according to the manufacture instructions.

Results

As used herein, control used without the presence of an inhibitor indicates 50 inhibition concentration (IC50) of cell viability.

Compounds of Formula (I) exhibited an inhibition range greater than 100 nM at IC50 concentration. Specially, Compounds 40 and 121 exhibited an inhibition level greater than those exhibited by Vandetinib and Sunitinib, widely known kinase inhibitors, in RET induced cancer cell line.

For example, Compound 121 of Formula (I), 2-(4-(4-(3-((dimethylamino)methyl)-4-methyl-1H-pyrrol-1-yl)-5-methylpyrimidin-2-ylamino)-2,6-dimethylphenoxy)ethanol, (see table 4) exhibited >2 time higher inhibition in IC50 measurement than those appeared by Vandetanib (AstraZeneca™) and Sunitinib (Pfizer™), which are an antagonist of the vascular endothelial growth factor receptor (VEGFR) and the epidermal growth factor receptor (EGFR). The IC50 inhibition data of the representative compounds of Formula (I) of the present invention is shown in Table 4.

TABLE 4

Cell Viability

| Compound no. | MTC-TT (IC50 nM) | Compound no. | MTC-TT (IC50 nM) |
|---|---|---|---|
| 40 | 78.4 | Vandetanib | 81.6 |
| 121 | 34.6 | Sunitinib | 116.7 |

4. Cell Viability Assay: Inhibition of FLT3-ITD-Positive Cells

Compounds of the invention were tested for their effects on inhibition of FLT3-ITD in human acute leukemia cell line (MV4-11). FLT3 is primarily expressed in immature hematopoietic progenitor as well as in mature myeloid cells. It belongs to type III receptor tyrosine kinase (RTK) family including KIT, FMS, and PDGFR. It is activated by binding to FL, which leads to increased kinase activity and activation of downstream signaling pathway including STATS, Ras, and PI3Kinase.

The FLT3-ITD (Internal Tandem Duplication) mutations in the juxtamembrane domain are the most frequently observed molecular defect in acute myelogenous leukemia (AML). FLT3-ITD induces ligand-independent dimerization, autophosphorylation and constitutive activation, and is able to transform hematopoietic cells. Clinically, FLT3-ITD is known to increased leukocytosis, increased blast count, increased relapse rate, decreased disease-free survival, and poor overall survival. Therefore, FLT3-ITD is an attractive molecular target for AML therapy.

Methods

Compounds of the invention were tested for cell viability effect on MV4-11 cells. For cell viability assay, MV4-11 cells expressing human FLT3-ITD were obtained from the American Type Culture Collection (ATCC, Manassas, Va.). This cell line was maintained with an Roswell Park Memorial Institute (RPMI) medium (HyClone™) containing 10 bovine calf serum (BCS; Hyclone™) supplemented iron. The MV4-11 cells were seeded at $2\times10^4$ cells in 96-well culture plates, and serially diluted compound was then added. After a 72-hour incubation period at 37° C., cell viability was measured using the ATPLite 1 step assay (Perkin-Elmer™) that is based on the quantification of ATP from viable cells. CellTiter Aqueous assay (Promega™) was also performed in parallel as an orthogonal assay. $IC_{50}$ values were calculated using nonlinear regression and defined as the concentration needed for a 50 reduction in luminescence or absorbance treated versus untreated control cells (Prism™ Software).

Results

Compounds of Formula (I) exhibited an inhibition of greater than 10 nM at IC50 concentration. Specially, Compounds 91 and 93 exhibited an inhibition level greater than those exhibited by Vandetinib and Sunitinib in FLT3 ITD induced cancer cell line.

For example, Compound 93, 1-((4-methyl-1-(5-methyl-2-(3,4,5-trimethoxyphenylamino)pyrimidin-4-yl)-1H-pyrrol-3-yl)methyl)azetidin-3-yl pivalate, exhibited more than 6 time higher inhibition in IC50 than those of Sunitinib (Pfizer) and PKC-412 (Novartis), widely known antagonists of the vascular endothelial growth factor receptor (VEGFR) and the epidermal growth factor receptor (EGFR). The IC50 inhibition data of the representative compounds of Formula (I) (e.g., Compound 91, 93, 96 and 97) are shown in Table 5.

TABLE 5

Viability of FLT3-ITD Induced Cancer Cell Line

| Compound no. | MV-4-11 (IC50 nM) | Compound no. | MV-4-11 (IC50 nM) |
|---|---|---|---|
| 91 | 1.5 | 97 | 79.2 |
| 93 | 0.6 | Sunitinib | 3.8 |
| 96 | 12.5 | PKC-412 | 11.7 |

5. Cell Viability Assay: JAK2 Inhibition

Compounds of the invention are tested for their effects on JAK2 inhibition in human erythroleukemic cell line (HEL) to illustrate potential efficacy at the cellular level. The Janus-associated kinase (JAK) family, comprised of four different protein tyrosine kinases JAK1, JAK2, JAK3, and TYK2, plays an important role in cellular survival, proliferation, and differentiation. V617F, a unique mutation in the JAK2 gene (a valine-to-phenylalanine substitution) results in constitutive kinase activity and promotes deregulated hematopoiesis. JAK2 V617F is frequently detected in myeloproliferative disorders (MPDs), a group of clonal hematopoietic stem cell disorders that include polycythemia vera (PV), essential thrombocythemia (ET), and idiopathic myelofibrosis (IMF), all of which have the potential to transform to acute myeloid leukemia. JAK2 V617F is constitutively phosphorylated and able to activate downstream signaling in the absence of cytokine stimulation.

JAK2 is also a key mediator of signaling, downstream of a variety of cytokine and growth factor receptors. In particular, JAK2 phosphorylate the signal transducers and activators of transcription (STAT) family of proteins. Once phosphorylated, STATs dimerize and translocate to the nucleus where they bind DNA and regulate expression of target genes. JAK2/STAT signaling has been implicated in driving both cell cycle regulation and anti-apoptotic pathways.

Methods

Compounds of the present invention were tested for their effects on viability of HEL cells. For cell viability assay, HEL cells expressing human JAK2 V617F were obtained from the American Type Culture Collection (ATCC, Manassas, Va.). This cell line was maintained with Roswell Park Memorial Institute (RPMI) medium (HyClone™) containing 10 bovine calf serum (BCS; Hyclone™) supplemented iron. The HEL cells were seeded at $2\times10^4$ cells in 96 well culture plates, and serially diluted compound was then added. After a 72-hour incubation period at 37° C., viability of cells was measured using the ATPLite 1 step assay (Perkin-Elmer™) that is based on the quantification of ATP from viable cells. CellTiter Aqueous assay (Promega™) was also performed in parallel as an orthogonal assay. $IC_{50}$ values were calculated using nonlinear regression and defined as the concentration needed for a 50 reduction in luminescence or absorbance treated versus untreated control cells (Prism™ Software).

Results

Compounds of Formula (I) exhibited an inhibition of greater than 10 nM at IC50 concentration. Specifically, compounds 21 and 24 exhibited an inhibition level greater than those exhibited by Sorafenib (Bayer), a known kinase inhibitor of Raf, VEGFR and PDGFR in cancer cell lines.

For example, Compound 21, (4-methyl-1-(5-methyl-2-(3,4,5-trimethoxyphenylamino)pyrimidin-4-yl)-1H-pyrrol-3-yl)methanol, (see table 6, compound 139) exhibited about 10 time higher inhibition in 1050 measurement than those by Sorafenib (Bayer). The IC50 inhibition data of the representative compounds of Formula (I) is shown in Table 6.

TABLE 6

| Cell Viability: JAK2 kinase Inhibition | | | |
|---|---|---|---|
| Compound no. | HEL (IC50 nM) | Compound no. | HEL (IC50 nM) |
| 21 | 144 | Sorafenib | >1000 |
| 24 | 229 | | |

6. In Vitro Kinase Inhibition

Up to 518 different kinases have been identified in humans. To determine the scope of inhibitory effects of a representative compound of Formula (I) on known kinases, Compound 82 was tested against 104 commercially available kinases (Ambit Biosciences™). 104 kinases included ABL1 (E255K)-phosphorylated, ABL1(T315I)-phosphorylated, ABL1-phosphorylated, ACVR1B, ADCK3, AKT1, AKT2, ALK, AURKA, AURKB, AXL, BMPR2, BRAF, BRAF (V600E), BTK, CDK11, CDK2, CDK3, CDK7, CDK9, CHEK1, CSF1R, CSNK1D, CSNK1G2, DCAMKL1, DYRK1B, EGFR, EGFR(L858R), EPHA2, ERBB2, ERBB4, ERK1, FAK, FGFR2, FGFR3, FLT1, FLT3, FLT4, GSK3B, IGF1R, IKK-α, IKK-β, INSR, JAK2(JH1domain-catalytic), JAK3 (JH1 domain-catalytic), JNK 1, JNK2, JNK3, KIT, KIT(D816V), KIT(V559D,T6701), LKB1, LRRK2, LRRK2(G2019S), MAP3K4, MAPKAPK2, MARKS, MEK1, MEK2, MET, MKNK1, MKNK2, MLK1, MTOR, p38-alpha, p38-beta, PAK1, PAK2, PAK-4, PCTK1, PDGFRA, PDGFRB, PDPK1, PIK3C2B, PIK3CA, PIK3CG, PIM1, PIM2, PIM3, PKAC-alpha, PLK1, PLK3, PLK4, PRKCE, PYK2, RAF1, RET, R10K2, ROCK2, RSK2, SNARK, SRC, SRPK3, SYK, TAK1, TGFBR1, TIE2, TRKA, TSSK1B, TYK2(JH1domain-catalytic), ULK2, VEGFR2, YANK3 and ZAP70.

Results

Inhibition activity of Compound 82 was reported as percent control where lower numbers indicate stronger activities. Table 7 summarizes 20 different kinases whose activity was significantly inhibited by the presence of Compound 82, (R)-1-((1-(2-(3,5-dimethylphenyl amino)-5-fluoropyrimidin-4-yl)-4-methyl-1H-pyrrol-3-yl)methyl)pyrrolidin-3-ol. Conventionally, the percent control of less than 35 is deemed to be significant inhibition of kinase activity as the numeric value 35 is frequently used as a threshold.

TABLE 7

| Kinase Inhibition Profile of the Percent Control Less than 35% | | | |
|---|---|---|---|
| Kinase | % inhibition | Kinase | % inhibition |
| ABL1(T315I) | 35 | MLK1 | 22 |
| AURKB | 31 | PDGFRB | 1.8 |
| AXL | 31 | PLK3 | 11 |
| FLT3 | 1.1 | RET | 32 |
| JAK2 | 3 | SNARK | 4.2 |
| JAK3 | 5.4 | SRPK3 | 25 |
| KIT | 26 | SYK | 1 |
| KIT(D816V) | 0.45 | TAK1 | 22 |
| KIT(V559D,T6701) | 28 | TYK2 | 21 |
| MKNK2 | 34 | ZAP70 | 34 |

While this invention has been particularly shown and described to example embodiments thereof, it will be understood by those skilled in the art that various changes in form and details may be made therein without departing from the scope of the invention encompassed by the appended claims.

What is claimed is:

1. A compound of Formula (I):

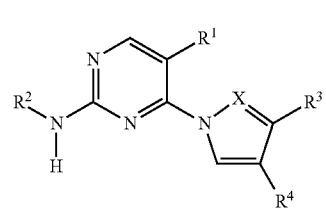

Formula I wherein:

X is CH or N;

$R^1$ is selected from H, halo, CN, $C_1$-$C_{10}$ alkyl or halo($C_1$-$C_4$)alkyl, wherein $C_1$-$C_{10}$ alkyl, or halo($C_1$-$C_4$)alkyl is optionally substituted;

$R^2$ is aryl, cycloalkyl, arylalkyl, or heterocyclyl, wherein the aryl, cycloalkyl, arylalkyl, or heterocyclyl is optionally and independently substituted at one or more carbon atoms with 1-4 $R^5$ or $R^{5a}$ groups; and wherein aryl and heterocyclyl having one or more nitrogen atoms is optionally and independently substituted at one or more nitrogen atoms with 1-4 $R^6$ or $R^{6a}$ groups;

$R^3$ is independently halo, CN, or $R^7$; and $R^4$ is selected from $(CH_2)_n OH$, $(CH_2)_n NR^{11}R^{12}$, $C(O)NHR^7$, $C(O)NR^{11}R^{12}$, $C(O)R^7$, $C(O)NR^7R^7$, $C(O)NR^7R^8$, $(CH_2)_n NR^7R^7$, $(CH_2)_n NR^7R^8$, $(CH_2)_n CN$, $(CH_2)_n SR^7$, $(CH_2)_n S(O)_n R^7$, or $(CH_2)_n S(O)_n NR^7R^7$, wherein each n is independently 1 or 2;

wherein:

Each $R^5$ is independently selected from halo, $CF_3$, $SR^7$, $OR^7$, $OC(O)R^7$, $O(CH_2)_n NR^7R^7$, $O(CH_2)_n NR^{11}R^{12}$, $O(CH_2)_n R^7$, $O(CH_2)_n C(O)NR^{11}R^{12}$, $O(CH_2)_n C(O)NR^7R^7$, $NR^7R^7$, $NR^7R^8$, $NHC(O)NH_2$, $C(O)OR^7$, $NO_2$, $CN$, $C(O)R^7$, $OSO_2CH_3$, $S(O)_n R^7$, $S(O)_n NR^7R^7$, $NR^7C(O)NR^7R^7$, $NR^7C(O)R^7$, $NR^7C(O)OR^7$, $NR^7S(O)_n R^7$, or $NR^{11}R^{12}$, wherein each n is independently 1 or 2;

Each $R^{5a}$ is independently selected from amino, halo, hydroxy, $C_1$-$C_{10}$ alkyl, $C_2$-$C_{10}$alkenyl, $C_3$-$C_{10}$ alkynyl, $C_3$-$C_{12}$cycloalkyl, $C_5$-$C_{10}$cycloalkenyl, alkoxy, haloalkyl, aryl, heteroaryl, or heterocyclyl, wherein the $C_1$-$C_{10}$ alkyl, $C_2$-$C_{10}$alkenyl, $C_3$-$C_{10}$alkynyl, $C_3$-$C_{12}$cycloalkyl, $C_5$-$C_{10}$cycloalkenyl, alkoxy, haloalkyl, aryl, heteroaryl, or heterocyclyl is optionally and independently substituted with 1 to 3 groups selected from halo, hydroxy, alkyl, $R^9$, or $R^{10}$;

Each $R^6$ is independently $R^7$, $C(O)CH_2CN$, $C(O)R^7$, $C(O)OR^7$, $CO_2(C_1$-$C_6$alkyl), $C(O)NR^7R^7$, $SO_2NR^7R^7$, or $SO_2R^7$;

Each $R^{6a}$ is independently hydroxy, $C_1$-$C_{10}$ alkyl, $C_2$-$C_{10}$ alkenyl, $C_3$-$C_{10}$ alkynyl, $C_3$-$C_{12}$ cycloalkyl, $C_5$-$C_{10}$ cycloalkenyl, haloalkyl, wherein each $R^{6a}$ group is optionally and independently substituted with 1-3 groups selected from hydroxy, aryl, alkyl, halo, $R^9$, or $R^{10}$;

Each $R^7$ is independently H, $C_1$-$C_{10}$alkyl, $C_2$-$C_{10}$alkenyl, $C_3$-$C_{10}$alkynyl, $C_3$-$C_{12}$ cycloalkyl, $C_5$-$C_{12}$cycloalkenyl, aryl, aryl($C_1$-$C_4$)alkyl, haloalkyl, heteroaryl, or heterocyclyl, wherein the $C_1$-$C_{10}$alkyl, $C_2$-$C_{10}$alkenyl, $C_3$-$C_{10}$alkynyl, $C_3$-$C_{12}$ cycloalkyl, $C_5$-$C_{12}$cycloalkenyl, aryl, aryl($C_1$-$C_4$) alkyl, haloalkyl, heteroaryl, or heterocyclyl is optionally and independently substituted with 1-4 groups selected from aryl, cycloalkyl, heteroaryl, heterocyclyl, alkyl, halo, amino, hydroxy, $R^9$, or $R^{10}$;

Each $R^8$ is independently $C(O)R^7$, $C(O)OR^7$, $C(O)NR^7R^7$, or $S(O)_nR^7$, wherein n is 1 or 2;

Each $R^9$ is independently $CF_3$, $SR^7$, $OR^7$, $NR^7R^7$, $NR^{11}R^{12}$, $C(O)NR^7R^7$, $C(O)NR^{11}R^{12}$, $S(O)_nNR^7R^7$, or $S(O)_nR^7$, wherein each n is independently 1 or 2;

Each $R^{10}$ is $C(O)O(C_1-C_6)$alkyl, or halo$(C_1-C_4)$alkyl; and $R^{11}$ and $R^{12}$, taken together with the nitrogen atom to which they are bonded form:
  i) a 3-8 membered saturated or partially saturated ring having no heteroatom other than the nitrogen atom to which $R^{11}$ and $R^{12}$ are bonded, wherein said 3-8 membered saturated or partially saturated ring is optionally and independently substituted with 1-4 groups selected from $R^5$ or $R^{5a}$ at one or more substitutable carbon atoms;
  ii) a 5-8 membered saturated or partially saturated ring having 1-3 heteroatoms, in addition to the nitrogen atom to which $R^{11}$ and $R^{12}$ are bonded, wherein said 1-3 heteroatoms are independently selected from nitrogen, oxygen, sulfur, sulfone or sulfoxide, and wherein said 5-8 membered saturated or partially saturated ring having 1-3 heteroatoms is optionally and independently substituted with 1-4 groups selected from $R^5$ or $R^{5a}$ at one or more substitutable carbon atoms and at one or more substitutable nitrogen atoms with $R^6$ or $R^{6a}$;
  iii) a 9-10 membered saturated or partially saturated bicyclic ring having no heteroatom other than the nitrogen atom to which $R^{11}$ and $R^{12}$ are bonded, wherein said 9-10 membered saturated or partially saturated bicyclic ring having no heteroatom is optionally substituted with 1-4 groups independently selected from $R^5$ or $R^{5a}$ at one or more substitutable carbon atoms;
  iv) a 9-10 membered saturated or partially saturated bicyclic ring having 1-5 heteroatoms, in addition to the nitrogen atom to which $R^{11}$ and $R^{12}$ are bonded, wherein said heteroatoms are independently selected from nitrogen, oxygen, sulfur, sulfoxide, sulfone, carboxamide or sulfoxamide; or
  v) a 6-14 membered saturated or partially saturated bridged ring having 1-3 heteroatoms in addition to the nitrogen atom to which $R^{11}$ and $R^{12}$ are bonded, wherein said 1-3 heteroatoms are independently selected from nitrogen, oxygen, sulfur, sulfone, or sulfoxide, and wherein said 6-14 membered saturated or partially saturated bridged ring having 1-3 heteroatoms is optionally and independently substituted with 1-4 groups selected from $R^5$ or $R^{5a}$ at one or more substitutable carbon atoms and at one or more substitutable nitrogen atoms with $R^6$ or $R^{6a}$;

or a pharmaceutically acceptable salt thereof.

2. The compound of claim 1, wherein $R^2$ is an aryl selected from: a 5-6 membered monocyclic aryl group having 0-3 heteroatoms independently selected from nitrogen, oxygen, or sulfur; an 8-10 membered bicyclic aryl group having 0-5 heteroatoms independently selected from nitrogen, oxygen, sulfur, sulfoxide, or sulfone; an 8-10 membered partially saturated bicyclic aryl group having 0-5 heteroatoms independently selected from nitrogen, oxygen, sulfur, sulfoxide, or sulfone; or an 8-10 membered partially saturated bicyclic aryl group having a carboxamide or sulfoxamide.

3. The compound of claim 2, wherein $R^2$ is a 5-6 membered monocyclic aryl having 0-3 heteroatoms independently selected from nitrogen, oxygen, or sulfur optionally and independently substituted with 1-4 $R^5$ or $R^{5a}$ groups.

4. The compound of claim 3, wherein the 5-6 membered monocyclic aryl is phenyl or pyrimidinyl optionally and independently substituted with 1, 2, or 3 groups selected from methyl, ethyl, phenyl, isoprophyl, methoxy, hydroxyethoxy, $CF_3$, $OC_6H_5$, $OCH_2CH_2NR^{11}R^{12}$, $OCH_2CH_2NR^7R^7$, $OCH_2C_6H_5$, $OCH_2C(O)NR^{11}R^{12}$, $OCH_2C(O)NR^7R^7$, $OSO_2CH_3$, $SO_2CH_3$, $SO_2NHCH_3$, or $NR^{11}R^{12}$.

5. The compound of claim 1, wherein $R^4$ is $(CH_2)_nNR^{11}R^{12}$, and $R^{11}$ and $R^{12}$, taken together with the nitrogen atom to which they are bonded form:
  i) a 3-8 membered saturated or partially saturated ring having no heteroatom other than the nitrogen atom to which $R^{11}$ and $R^{12}$ are bonded, wherein said 3-8 membered saturated or partially saturated ring is optionally and independently substituted with 1-4 groups selected from $R^5$ or $R^{5a}$ at one or more substitutable carbon atoms;
  ii) a 5-8 membered saturated or partially saturated ring having 1-3 heteroatoms, in addition to the nitrogen atom to which $R^{11}$ and $R^{12}$ are bonded, wherein said 1-3 heteroatoms are independently selected from nitrogen, oxygen, sulfur, sulfone or sulfoxide, and wherein said 5-8 membered saturated or partially saturated ring having 1-3 heteroatoms is optionally and independently substituted with 1-4 groups selected from $R^5$ or $R^{5a}$ at one or more substitutable carbon atoms and at one or more substitutable nitrogen atoms with $R^6$ or $R^{6a}$;
  iii) a 9-10 membered saturated or partially saturated bicyclic ring having no heteroatom other than the nitrogen atom to which $R^{11}$ and $R^{12}$ are bonded, wherein said 9-10 membered saturated or partially saturated bicyclic ring having no heteroatom is optionally substituted with 1-4 groups independently selected from $R^5$ or $R^{5a}$ at one or more substitutable carbon atoms;
  iv) a 9-10 membered saturated or partially saturated bicyclic ring having 1-5 heteroatoms, in addition to the nitrogen atom to which $R^{11}$ and $R^{12}$ are bonded, wherein said heteroatoms are independently selected from nitrogen, oxygen, sulfur, sulfoxide, sulfone, carboxamide or sulfoxamide; or
  v) a 6-14 membered saturated or partially saturated bridged ring having 1-3 heteroatoms in addition to the nitrogen atom to which $R^{11}$ and $R^{12}$ are bonded, wherein said 1-3 heteroatoms are independently selected from nitrogen, oxygen, sulfur, sulfone, or sulfoxide, and wherein said 6-14 membered saturated or partially saturated bridged ring having 1-3 heteroatoms is optionally and independently substituted with 1-4 groups selected from $R^5$ or $R^{5a}$ at one or more substitutable carbon atoms and at one or more substitutable nitrogen atoms with $R^6$ or $R^{6a}$.

6. The compound of claim 5, wherein $R^{11}$ and $R^{12}$, taken together with the nitrogen atom to which they are bonded form a 3-8 membered saturated or partially saturated ring having no heteroatom other than the nitrogen atom to which $R^{11}$ and $R^{12}$ are bonded, wherein said 3-8 membered ring is optionally and independently substituted with 1-4 groups selected from $R^5$ or $R^{5a}$ at one or more substitutable carbon atoms.

7. The compound of claim 6, wherein the 3-8 membered saturated or partially saturated ring is a 4-6 membered ring selected from azetidinyl, pyrrolidinyl, or piperidinyl optionally and independently substituted with 1-2 groups selected from hydroxy, halo, $OC(O)R^7$, $CH_2OH$, $CH_2CH_2OH$, $NH_2$, $NR^7R^7$, $NHC(O)NHR^7$, $NHSO_2R^7$, $C(O)OR^7$, or $C(O)NHR^7$ at one or more substitutable carbon atoms.

8. A compound selected from:
methyl 1-(5-methyl-2-(3,4,5-trimethoxyphenylamino)pyrimidin-4-yl)-1H-pyrrole-3-carboxylate;
ethyl 1-(2-(3,5-dimethylphenylamino)pyrimidin-4-yl)-3-methyl-1H-pyrazole-4-carboxylate;
1-(2-(3,5-dimethylphenylamino)pyrimidin-4-yl)-3-methyl-1H-pyrazole-4-carboxylic acid;
(1-(2-(3,5-dimethylphenylamino)-5-fluoropyrimidin-4-yl)-3-methyl-1H-pyrazol-4-yl)methanol;
(1-(2-(3,5-dimethylphenylamino)pyrimidin-4-yl)-3-methyl-1H-pyrazol-4-yl)methanol;
(1-(2-(3,5-dimethylphenylamino)-5-fluoropyrimidin-4-yl)-1H-pyrazol-4-yl)methanol;
(1-(2-(3,5-dimethoxyphenylamino)-5-fluoro pyrimidin-4-yl)-1H-pyrazol-4-yl)methanol;
(1-(2-(3,5-dimethoxyphenylamino)-5-fluoropyrimidin-4-yl)-3-methyl-1H-pyrazol-4-yl)methanol;
(1-(2-(3,5-dimethyl phenylamino)pyrimidin-4-yl)-1H-pyrrol-3-yl)methanol;
(1-(2-(2,3-dihydro-1H-inden-5-ylamino)pyrimidin-4-yl)-1H-pyrrol-3-yl)methanol;
(1-(2-(3,5-dimethyl-4-(2-(pyrrolidin-1-yl)ethoxy)phenylamino)pyrimidin-4-yl)-4-methyl-1H-pyrrol-3-yl)methanol;
(1-(2-(3,5-dimethyl-4-phenoxyphenylamino)pyrimidin-4-yl)-4-methyl-1H-pyrrol-3-yl)methanol;
(1-(2-(3,5-dimethylphenylamino)-5-fluoropyrimidin-4-yl)-1H-pyrrol-3-yl)methanol;
(1-(2-(3,5-dimethylphenylamino)-5-fluoropyrimidin-4-yl)-4-methyl-1H-pyrrol-3-yl)methanol;
2-(4-(5-fluoro-4-(3-(hydroxymethyl)-4-methyl-1H-pyrrol-1-yl)pyrimidin-2-ylamino)-2,6-dimethylphenoxy)ethanol;
(1-(2-(3,5-dimethoxyphenylamino)-5-fluoropyrimidin-4-yl)-4-methyl-1H-pyrrol-3-yl)methanol;
(1-(2-(3,5-bis(trifluoromethyl)phenylamino)-5-fluoropyrimidin-4-yl)-4-methyl-1H-pyrrol-3-yl)methanol;
(1-(5-fluoro-2-(naphthalene-2-ylamino)pyrimidin-4-yl)-4-methyl-1H-pyrrol-3-yl)methanol;
(1-(5-chloro-2-(3,4,5-trimethoxyphenylamino)pyrimidin-4-yl)-4-methyl-1H-pyrrol-3-yl)methanol;
(4-cyclopropyl-1-(5-methyl-2-(3,4,5-trimethoxyphenylamino)pyrimidin-4-yl)-1H-pyrrol-3-yl)methanol;
(4-methyl-1-(5-methyl-2-(3,4,5-trimethoxyphenylamino)pyrimidin-4-yl)-1H-pyrrol-3-yl)methanol;
2-(4-(4-(3-(hydroxyl methyl)-4-methyl-1H-pyrrol-1-yl)-5-methyl pyrimidin-2-ylamino)-2,6-dimethoxyphenoxy)ethanol;
2-(4-(4-(4-(3-(hydroxylmethyl)-4-methyl-1H-pyrrol-1-yl)-5-methyl pyrimidin-2-ylamino)-2-methylphenyl)piperazin-1-yl)ethanol;
(S)-1-(4-(4-(3-(hydroxylmethyl)-4-methyl-1H-pyrrol-1-yl)-5-methyl pyrimidin-2-ylamino)-2-methylphenyl)pyrrolidin-3-ol;
(1-(5-fluoro-2-(4-(methylsulfonyl)phenylamino)pyrimidin-4-yl)-4-methyl-1H-pyrrol-3-yl)methanol;
(1-(2-(3,5-dimethylphenylamino)-5-(trifluoromethyl)pyrimidin-4-yl)-4-methyl-1H-pyrrol-3-yl)methanol;
(1-(2-(3,5-dimethylphenylamino)-5-fluoropyrimidin-4-yl)-4-phenyl-1H-pyrrol-3-yl)methanol;
(1-(5-fluoro-2-(3,4,5-trimethoxyphenylamino)pyrimidin-4-yl)-4-(furan-3-yl)-1H-pyrrol-3-yl)methanol;
1-(2-(3,5-dimethylphenylamino)pyrimidin-4-yl)-N-(2-hydroxyethyl)-N,3-dimethyl-1H-pyrazole-4-carboxamide;
1-(2-(3,5-dimethylphenylamino)pyrimidin-4-yl)-N,N-bis(2-hydroxyethyl)-3-methyl-1H-pyrazole-4-carboxamide;
(S)-(1-(2-(3,5-dimethylphenylamino)pyrimidin-4-yl)-3-methyl-1H-pyrazol-4-yl)(3-hydroxypyrrolidin-1-yl)methanone;
(R)-(1-(2-(3,5-dimethylphenylamino)pyrimidin-4-yl)-3-methyl-1H-pyrazol-4-yl)(3-hydroxypyrrolidin-1-yl)methanone;
N-(2-aminoethyl)-1-(2-(3,5-dimethylphenylamino)pyrimidin-4-yl)-3-(trifluoromethyl)-1H-pyrazole-4-carboxamide;
1-(2-(3,5-dimethoxyphenylamino)-5-fluoropyrimidin-4-yl)-N-(3,5-dimethyl phenyl)-1H-pyrazole-4-carboxamide;
(1-(2-(3,5-dimethoxyphenylamino)-5-fluoropyrimidin-4-yl)-1H-pyrazol-4-yl)(piperidin-1-yl)methanone;
(S)-1-(2-(3,5-dimethoxyphenylamino)-5-fluoropyrimidin-4-yl)-N-(1-hydroxy propan-2-yl)-3-methyl-1H-pyrazole-4-carboxamide;
N-benzyl-1-(2-(3,5-dimethoxyphenylamino)-5-fluoropyrimidin-4-yl)-1H-pyrazole-4-carboxamide;
(R)-(1-(2-(3,5-dimethylphenylamino)-5-fluoropyrimidin-4-yl)-3-methyl-1H-pyrazol-4-yl)(3-hydroxypyrrolidin-1-yl)methanone;
2-((1-(2-(3,5-dimethylphenylamino)-5-fluoropyrimidin-4-yl)-3-methyl-1H-pyrazol-4-yl)methylamino)ethanol;
2-(4-((4-methyl-1-(5-methyl-2-(3,4,5-trimethoxyphenylamino)pyrimidin-4-yl)-1H-pyrrol-3-yl)methyl)piperazin-1-yl)ethanol;
(R)-1-((1-(2-(3,5-dimethylphenylamino)pyrimidin-4-yl)-4-methyl-1H-pyrrol-3-yl)methyl)pyrrolidin-3-ol;
1-((4-cyclopropyl-1-(2-(3,5-dimethylphenylamino)pyrimidin-4-yl)-1H-pyrrol-3-yl)methyl)azetidin-3-ol;
4-(4-((benzylamino)methyl)-3-methyl-1H-pyrazol-1-yl)-N-(3,5-dimethylphenyl)pyrimidin-2-amine;
4-(4-(3-((3-hydroxyazetidin-1-yl)methyl)-4-methyl-1H-pyrrol-1-yl)pyrimidin-2-ylamino)-2,6-dimethylphenyl methanesulfonate;
(R)-4-(4-(3-((3-hydroxypyrrolidin-1-yl)methyl)-4-methyl-1H-pyrrol-1-yl)pyrimidin-2-ylamino)-N,2-dimethylbenzenesulfonamide;
(R)-1-((1-(2-(3,5-dimethyl-4-(2-(pyrrolidin-1-yl)ethoxy)phenyl amino)pyrimidin-4-yl)-3-methyl-1H-pyrazol-4-yl)methyl)pyrrolidin-3-ol;
(S)-1-((1-(2-(3,5-dimethylphenylamino)pyrimidin-4-yl)-4-methyl-1H-pyrrol-3-yl)methyl)pyrrolidine-3-carboxylic acid;
(R)-1-((1-(2-(3,5-dimethyl-4-phenoxyphenylamino)pyrimidin-4-yl)-4-methyl-1H-pyrrol-3-yl)methyl)pyrrolidin-3-ol;
(R)-1-(1-((1-(2-(3,5-dimethylphenylamino)pyrimidin-4-yl)-4-methyl-1H-pyrrol-3-yl)methyl)pyrrolidin-3-yl)urea;
1-((4-methyl-1-(2-(2-methylbiphenyl-4-ylamino)pyrimidin-4-yl)-1H-pyrrol-3-yl)methyl)azetidin-3-ol;
1-((1-(2-(2,3-dihydro-1H-inden-5-ylamino)pyrimidin-4-yl)-4-methyl-1H-pyrrol-3-yl)methyl)azetidin-3-ol1-((4-methyl-1-(2-(1-methyl-1H-indol-5-ylamino)pyrimidin-4-yl)-1H-pyrrol-3-yl)methyl)azetidin-3-ol;
(R)-1-((4-methyl-1-(2-(1-methyl-1H-indo-5-ylamino)pyrimidin-4-yl)-1H-pyrrol-3-yl)methyl) pyrrolidin-3-ol;
4-(3-((4,4-difluoropiperidin-1-yl)methyl)-4-methyl-1H-pyrrol-1-yl)-N-(3,5-dimethylphenyl)pyrimidin-2-amine;

(R)-2-(4-(4-(4-((3-hydroxypyrrolidin-1-yl)methyl)-3-methyl-1H-pyrazol-1-yl)pyrimidin-2-ylamino)-2,6-dimethylphenoxy)-1-morpholinoethanone;

2-(4-(4-(4-((3-hydroxyazetidin-1-yl)methyl)-3-methyl-1H-pyrazol-1-yl)pyrimidin-2-ylamino)-2,6-dimethylphenoxy)-1-morpholinoethanone;

N-(3,5-dimethylphenyl)-5-fluoro-4-(3-methyl-4-(pyrrolidin-1-ylmethyl)-1H-pyrazol-1-yl)pyrimidin-2-amine;

N-(3,5-dimethylphenyl)-5-fluoro-4-(3-methyl-4-(pyrrolidin-1-ylmethyl)-1H-pyrazol-1-yl)pyrimidin-2-amine;

(S)-2-((1-(2-(3,5-dimethylphenylamino)-5-fluoropyrimidin-4-yl)-3-methyl-1H-pyrazol-4-yl)methyl amino) propan-1-ol;

4-(4-((cyclopropylamino)methyl)-3-methyl-1H-pyrazol-1-yl)-N-(3,5-dimethylphenyl)-5-fluoropyrimidin-2-amine;

4-(4-((cyclohexylamino)methyl)-3-methyl-pyrazol-1-yl)-N-(3,5-dimethylphenyl)-5-fluoropyrimidin-2-amine;

N-(3,5-dimethylphenyl)-5-fluoro-4-(3-methyl-4-(piperidin-1-ylmethyl)-1H-1-pyrazol-1-yl)pyrimidin-2-amine;

N-(3,5-dimethylphenyl)-5-fluoro-4-(3-methyl-4-(morpholinomethyl)-1H-pyrazol-1-yl)pyrimidin-2-amine;

N-(3,5-dimethylphenyl)-5-fluoro-4-(3-methyl-4-((phenylamino)methyl)-1H-pyrazol-1-yl)pyrimidin-2-amine;

4-(4-((3,4-dihydroisoquinolin-2(1H)-yl)methyl)-3-methyl-1H-pyrazol-1-yl)-N-(3,5-dimethyl phenyl)-5-fluoropyrimidin-2-amine;

4-(4-((benzyl(methyl)amino)methyl)-3-methyl-1H-pyrazol-1-yl)-N-(3,5-dimethylphenyl)-5-fluoro pyrimidin-2-amine;

$N^1$-((1-(2-(3,5-dimethylphenylamino)-5-fluoropyrimidin-4-yl)-3-methyl-1H-pyrazol-4-yl)methyl)ethane-1,2-diamine;

N-(3,5-dimethylphenyl)-5-fluoro-4-(4-((4-fluorophenethylamino)methyl)-3-methyl-1-pyrazol-1-yl)pyrimidin-2-amine;

N-(3,5-dimethylphenyl)-5-fluoro-4-(3-methyl-4-((pyridin-4-ylmethylamino)methyl)-1H-pyrazol-1-yl)pyrimidin-2-amine;

(S)-1-((1-(2-(3,5-dimethylphenylamino)-5-fluoropyrimidin-4-yl)-3-methyl-1H-pyrazol-4-yl)methyl)pyrrolidin-3-ol;

(R)-1-((1-(2-(3,5-dimethylphenylamino)-5-fluoropyrimidin-4-yl)-3-methyl-1H-pyrazol-4-yl)methyl)pyrrolidin-3-ol;

1-((1-(2-(3,5-dimethylphenylamino)-5-fluoropyrimidin-4-yl)-3-methyl-1H-1-pyrazol-4-yl)methyl)piperidin-4-ol;

N-(3,5-dimethylphenyl)-5-fluoro-4-(3-methyl-4-(piperidin-1-ylmethyl)-1H-pyrrol-1-yl)pyrimidin-2-amine;

1-((3-methyl-1-(5-methyl-2-(3,4,5-trimethoxyphenylamino)pyrimidin-4-yl)-1H-pyrazol-4-yl)methyl)azetidin-3-ol;

2-((1-(2-(3,5-dimethylphenylamino)-5-fluoropyrimidin-4-yl)-3-methyl-1H-pyrazol-4-yl)methyl amino)ethanol;

4-(4-((benzylamino)methyl)-3-methyl-1H-pyrazol-1-yl)-N-(3,5-dimethylphenyl)-5-fluoropyrimidin-2-amine;

N-(3,5-dimethylphenyl)-5-fluoro-4-(3-methyl-4-((4-methylpiperazin-1-yl)methyl)-1H-pyrazol-1-yl)pyrimidin-2-amine;

4-(4-((dimethylamino)methyl)-3-methyl-1H-pyrazol-1-yl)-N-(3,5-dimethylphenyl)-5-fluoropyrimidin-2-amine;

N-(3,5-dimethylphenyl)-5-fluoro-4-(3-methyl-4-((piperidin-4-ylamino) methyl)-1H-pyrazol-1-yl)pyrimidin-2-amine trihydrochloride;

N-(3,5-dimethylphenyl)-5-fluoro-4-(3-(3-sulfonylpyrrolidin-1-ylmethyl)-1H-pyrrol-1-yl)pyrimidin-2-amine;

4-(3-((dimethylamino)methyl)-4-methyl-1H-pyrrol-1-yl)-N-(3,5-dimethylphenyl)-5-fluoropyrimidin-2-amine;

N-(3,5-dimethylphenyl)-5-fluoro-4-(3-methyl-4-(morpholinomethyl)-1H-pyrrol-1-yl)pyrimidin-2-amine;

(R)-1-((1-(2-(3,5-dimethylphenylamino)-5-fluoropyrimidin-4-yl)-4-methyl-1H-pyrrol-3-yl)methyl) pyrrolidin-3-ol;

1-((1-(2-(3,4-dimethylphenylamino)-5-fluoropyrimidin-4-yl)-4-methyl-1H-pyrrol-3-yl)methyl)azetidin-3-ol;

(R)-2-(4-(5-fluoro-4-(3-((3-hydroxypyrrolidin-1-yl)methyl)-4-methyl-1H-pyrrol-1-yl)pyrimidin-2-ylamino)-2,6-dimethylphenoxy)-1-morpholinoethanone;

3-(4-((4-methyl-1-(5-methyl-2-(3,4,5-trimethoxyphenylamino)pyrimidin-4-yl)-1H-pyrrol-3-yl)methyl)piperazin-1-yl)-3-oxopropanenitrile;

(R)-4-(3-((3-aminopyrrolidin-1-yl)methyl)-4-methyl-1H-pyrrol-1-yl)-N-(3,5-dimethylphenyl)-5-fluoropyrimidin-2-amine;

1-((1-(5-fluoro-2-(naphthalen-2-ylamino)pyrimidin-4-yl)-4-methyl-1H-pyrrol-3-yl)methyl)azetidin-3-ol;

1-((1-(2-(4-(benzyloxy)-3,5-dimethoxyphenylamino)-5-methylpyrimidin-4-yl)-1H-pyrrol-3-yl)methyl)azetidin-3-ol;

(R)-4-(5-fluoro-4-(3-((3-hydroxypyrrolidin-1-yl)methyl)-4-methyl-1H-pyrrol-1-yl)pyrimidin-2-ylamino)-2,6-dimethylphenyl methanesulfonate;

(R)-1-((1-(5-fluoro-2-(4-(2-hydroxyethoxy)-3,5-dimethylphenylamino)pyrimidin-4-yl)-4-methyl-1H-pyrrol-3-yl)methyl)pyrrolidin-3-ol;

1-((4-methyl-1-(5-methyl-2-(3,4,5-trimethoxyphenylamino)pyrimidin-4-yl)-1H-pyrrol-3-yl)methyl)azetidin-3-ol;

1-((4-methyl-1-(5-methyl-2-(3,4,5-trimethoxyphenylamino)pyrimidin-4-yl)-1H-pyrrol-3-yl)methyl)azetidin-3-yl acetate;

1-((4-methyl-1-(5-methyl-2-(3,4,5-trimethoxyphenylamino)pyrimidin-4-yl)-1H-pyrrol-3-yl)methyl)azetidin-3-yl pivalate;

1-((4-cyclopropyl-1-(5-methyl-2-(3,4,5-trimethoxyphenylamino)pyrimidin-4-yl)-1H-pyrrol-3-yl)methyl)azetidin-3-ol;

1-((4-methyl-1-(5-methyl-2-(3,4,5-trimethoxyphenylamino)pyrimidin-4-yl)-1H-pyrrol-3-yl)methypurea;

4-(3-((1,4-diazepan-1-yl)methyl)-4-methyl-1H-pyrrol-1-yl)-5-methyl-N-(3,4,5-trimethoxyphenyl)pyrimidin-2-amine trihydrochloride;

(S)-1-((1-(2-(3,5-dimethylphenylamino)-5-fluoropyrimidin-4-yl)-4-methyl-1H-pyrrol-3-yl)methyl) pyrrolidin-3-ol;

2,2-dimethyl-1-(4-((4-methyl-1-(5-methyl-2-(3,4,5-trimethoxyphenylamino)pyrimidin-4-yl)-1H-pyrrol-3-yl)methyl)-1,4-diazepan-1-yl)propan-1-one;

(S)-1-((1-(2-(3,5-dimethylphenylamino)-5-fluoropyrimidin-4-yl)-4-methyl-1H-pyrrol-3-yl)methyl)pyrrolidin-3-ol;

1-((1-(2-(3,5-dimethylphenylamino)-5-fluoropyrimidin-4-yl)-4-methyl-1H-pyrrol-3-yl)methyl)piperidin-4-ol;

(S)-2-((1-(2-(3,5-dimethylphenylamino)-5-fluoropyrimidin-4-yl)-4-methyl-1H-pyrrol-3-yl)methylamino)propan-1-ol;

4-(3-((benzylamino)methyl)-4-methyl-1H-pyrrol-1-yl)-N-(3,5-dimethoxyphenyl)-5-fluoro pyrimidin-2-amine;

(R)-1-((1-(2-(3,5-dimethoxyphenylamino)-5-fluoropyrimidin-4-yl)-4-methyl-1H-pyrrol-3-yl)methyl)pyrrolidin-3-ol;

4-(3-((dimethylamino)methyl)-4-(furan-3-yl)-1H-pyrrol-1-yl)-5-fluoro-N-(3,4,5-trimethoxyphenyl)pyrimidin-2-amine;

1-((1-(2-(3,5-dimethoxyphenylamino)-5-fluoropyrimidin-4-yl)-4-methyl-1H-pyrrol-3-yl)methyl) piperidin-4-ol;

N-(3,5-dimethoxyphenyl)-4-(3-((dimethylamino)methyl)-4-methyl-1H-pyrrol-1-yl)-5-fluoropyrimidin-2-amine;

(R)-1-((1-(5-fluoro-2-(3-(trifluoromethyl)phenylamino) pyrimidin-4-yl)-4-methyl-1H-pyrrol-3-yl)methyl)pyrrolidin-3-ol;

1-((1-(5-fluoro-2-(3-(trifluoromethyl)phenylamino)pyrimidin-4-yl)-4-methyl-1H-pyrrol-3-yl) methyl)piperidin-4-ol;

2-(4-((1-(5-chloro-2-(3,4,5-trimethoxyphenylamino)pyrimidin-4-yl)-4-methyl-1H-pyrrol-3-yl)methyl)piperazin-1-yl)ethanol;

1-((1-(5-chloro-2-(3,4,5-trimethoxyphenylamino)pyrimidin-4-yl)-4-methyl-1H-pyrrol-3-yl)methypazetidin-3-ol;

1-((1-(5-chloro-2-(4-(2-hydroxyethoxy)-3,5-dimethylphenylamino)pyrimidin-4-yl)-4-methyl-1H-pyrrol-3-yl)methypazetidin-3-ol;

4-(3-((dimethylamino)methyl)-4-methyl-1H-pyrrol-1-yl)-N-(3,5-dimethylphenyl)-5-methylpyrimidin-2-amine;

4-(3-((dimethylamino)methyl)-4-methyl-1H-pyrrol-1-yl)-N-(3,5-dimethylphenyl)-5-methylpyrimidin-2-amine;

1-((1-(2-(3,5-dimethylphenylamino)-5-methylpyrimidin-4-yl)-4-methyl-1H-pyrrol-3-yl)methyl)piperidin-4-ol;

2-(4-((1-(2-(4-(4-(2-hydroxyethyl)piperazin-1-yl)-3-methylphenylamino)-5-methylpyrimidin-4-yl)-4-methyl-1H-pyrrol-3-yl)methyl)piperazin-1-ypethanol;

4-((1-(2-(4-(2-hydroxyethoxy)-3,5-dimethylphenylamino)-5-methylpyrimidin-4-yl)-4-methyl-1H-pyrrol-3-yl)methyl)-N-methyl-1,4-diazepane-1-carboxamide;

4-((1-(2-(4-(2-hydroxyethoxy)-3,5-dimethylphenylamino)-5-methylpyrimidin-4-yl)-4-methyl-1H-pyrrol-3-yl)methyl)-1,4-diazepane-1-carboxamide;

1-((4-methyl-1-(5-methyl-2-(3,4,5-trimethoxyphenylamino)pyrimidin-4-yl)-1H-pyrrol-3-yl)methyl)piperidin-4-ol;

(1-((4-methyl-1-(5-methyl-2-(3,4,5-trimethoxyphenylamino)pyrimidin-4-yl)-1H-pyrrol-3-yl)methyl)piperidin-4-yl)methanol;

1-((1-(2-(3,5-dimethyl-4-(2(pyrrolidin-1-ypethoxy)phenylamino)-5-methylpyrimidin-4-yl)-4-methyl-1H-pyrrol-3-yl)methyl) azetidin-3-ol;

2-(4-(4-(3-((dimethylamino)methyl)-4-methyl-1H-pyrrol-1-yl)-5-methylpyrimidin-2-ylamino)-2,6-dimethylphenoxy)ethanol;

(R)-1-((1-(5-fluoro-2-(4-(2-hydroxyethoxy)-3,5-dimethylphenylamino)pyrimidin-4-yl)-4-methyl-1H-pyrrol-3-yl)methyl)pyrrolidin-3-ol;

4-(3-((dimethylamino)methyl)-4-methyl-1H-pyrrol-1-yl)-5-fluoro-N-(3-(trifluoromethyl)phenyl) pyrimidin-2-amine;

2-(4-(5-fluoro-4-(3-((3-hydroxyazetidin-1-yl)methyl)-4-methyl-1H-pyrrol-1-yl)pyrimidin-2-ylamino)-2,6-dimethylphenoxy)-1-(pyrrolidin-1-yl)ethanone;

(R)-1-((1-(2-(3,5-dimethylphenyl amino)-5-(trifluoromethyl) pyrimidin-4-yl)-4-methyl-1H-pyrrol-3-yl)methyl)pyrrolidin-3-ol;

1-((1-(5-fluoro-2-(3,4,5-trimethoxyphenylamino)pyrimidin-4-yl)-4-(furan-3-yl)-1H-pyrrol-3-yl)methypazetidin-3-ol;

4-(3-((dimethylamino)methyl)-4-phenyl-1H-pyrrol-1-yl)-N-(3,5-dimethylphenyl)-5-fluoropyrimidin-2-amine;

(R)-1-((1-(2-(3,5-dimethylphenylamino)-5-fluoropyrimidin-4-yl)-4-phenyl-1H-pyrrol-3-yl)methyl)pyrrolidin-3-ol;

N-(3,5-bis(trifluoromethyl)phenyl)-4-(3-((dimethylamino)methyl)-4-methyl-1H-pyrrol-1-yl)-5-fluoropyrimidin-2-amine;

(R)-1-((1-(2-(3,5-bis(trifluoromethyl)phenylamino)-5-fluoropyrimidin-4-yl)-4-methyl-1H-pyrrol-3-yl)methyl)pyrrolidin-3-ol;

1-((1-(2-(3,5-bis(trifluoromethyl)phenylamino)-5-fluoropyrimidin-4-yl)-4-methyl-1H-pyrrol-3-yl)methyl)piperidin-4-ol;

4-(3-((dimethylamino)methyl)-1H-pyrrol-1-yl)-N-(3,5-dimethylphenyl)-5-fluoropyrimidin-2-amine;

(R)-1-((1-(2-(3,5-dimethylphenylamino)-5-fluoropyrimidin-4-yl)-1H-pyrrol-3-yl)methyl)pyrrolidin-3-ol;

4-(3-(2,5-diazabicyclo[2.2.1]heptan-2-ylmethyl)-4-methyl-1H-pyrrol-1-yl)-5-bromo-N-(3,4,5-trimethoxyphenyl)pyrimidin-2-amine trihydrochloride;

(R)-2-(4-(5-fluoro-4-(3-((3-hydroxypyrrolidin-1-yl)methyl)-4-methyl-1H-pyrrol-1-yl)pyrimidin-2-ylamino)-2,6-dimethylphenoxy)-1-morpholinoethanone;

2-(4-(4-(3-(2,5-diazabicyclo[2.2.1]heptan-2-ylmethyl)-4-methyl-1H-pyrrol-1-yl)-5-methylpyrimidin-2-ylamino)-2,6-dimethylphenoxy)ethanol trihydrochloride;

4-(3-((1,4-diazepan-1-yl)methyl)-4-methyl-1H-pyrrol-1-yl)-5-chloro-N-(2,3-dihydrobenzo[b][1,4]dioxin-6-yl) pyrimidin-2-amine;

1-((1-(5-chloro-2-(2,3-dihydrobenzo[b][1,4]dioxin-6-ylamino)pyrimidin-4-yl)-4-methyl-1H-pyrrol-3-yl)methyl)azetidin-3-ol; or (R)-1-((1-(2-(4,6-dimethylpyrimidin-2-ylamino)-5-fluoropyrimidin-4-yl)-4-methyl-1H-pyrrol-3-yl)methyl) pyrrolidin-3-ol.

9. A pharmaceutical formulation comprising a compound of claim 1 in combination with a pharmaceutically acceptable carrier, diluent or excipient.

10. The compound of claim 1, wherein X is CH.

* * * * *